(12) United States Patent
Castaigne et al.

(10) Patent No.: US 9,914,754 B2
(45) Date of Patent: Mar. 13, 2018

(54) **CONJUGATES OF NEUROTENSIN OR NEUROTENSIN

(56) References Cited

U.S. PATENT DOCUMENTS

| | | |
|---|---|---|
| 6,660,525 B2 | 12/2003 | Martin et al. |
| 6,689,582 B1 | 2/2004 | Davies et al. |
| 6,713,454 B1 | 3/2004 | Ekwuribe et al. |
| 6,906,033 B2 | 6/2005 | White et al. |
| 6,929,919 B2 * | 8/2005 | St. George-Hyslop et al. .......................... 435/7.1 |
| 6,930,090 B2 | 8/2005 | Ekwuribe et al. |
| 7,019,123 B2 | 3/2006 | Tamburini et al. |
| 7,049,058 B2 | 5/2006 | Singh |
| 7,067,632 B2 | 6/2006 | Elliott |
| 7,101,844 B2 | 9/2006 | Kim et al. |
| 7,115,707 B2 | 10/2006 | Ben-Sasson et al. |
| 7,153,946 B2 | 12/2006 | McChesney et al. |
| 7,192,921 B2 | 3/2007 | Laakkonen et al. |
| 7,208,174 B2 | 4/2007 | Huwyler et al. |
| 7,214,657 B2 | 5/2007 | Kream |
| 7,319,090 B2 | 1/2008 | Katz |
| 7,557,182 B2 | 7/2009 | Beliveau et al. |
| 7,569,544 B2 | 8/2009 | Zankel et al. |
| 7,700,554 B2 | 4/2010 | Beliveau et al. |
| 7,902,156 B2 | 3/2011 | Beliveau et al. |
| 8,530,429 B2 | 9/2013 | Robbins et al. |
| 8,569,323 B2 | 10/2013 | Ren et al. |
| 8,828,925 B2 | 9/2014 | Demeule et al. |
| 9,173,891 B2 | 11/2015 | Castaigne et al. |
| 2003/0129186 A1 | 7/2003 | Beliveau et al. |
| 2003/0170891 A1 | 9/2003 | McSwiggen |
| 2004/0077540 A1 | 4/2004 | Quay |
| 2004/0087499 A1 | 5/2004 | Laakkonen et al. |
| 2004/0101904 A1 | 5/2004 | Pardridge et al. |
| 2004/0102369 A1 | 5/2004 | Wu et al. |
| 2004/0146549 A1 | 7/2004 | Ben-Sasson et al. |
| 2004/0162284 A1 * | 8/2004 | Harris et al. .................. 514/221 |
| 2004/0220132 A1 | 11/2004 | Kaemmerer |
| 2005/0026823 A1 | 2/2005 | Zankel et al. |
| 2005/0042227 A1 | 2/2005 | Zankel et al. |
| 2005/0058702 A1 | 3/2005 | Ben-Sasson et al. |
| 2005/0100986 A1 | 5/2005 | Verma et al. |
| 2005/0107325 A1 | 5/2005 | Manoharan et al. |
| 2005/0178395 A1 | 8/2005 | Hunter et al. |
| 2005/0183731 A1 | 8/2005 | Hunter et al. |
| 2006/0019347 A1 | 1/2006 | Cho et al. |
| 2006/0029609 A1 | 2/2006 | Zankel et al. |
| 2006/0182684 A1 | 8/2006 | Beliveau |
| 2006/0189515 A1 | 8/2006 | Beliveau et al. |
| 2006/0251713 A1 | 11/2006 | Ben-Sasson et al. |
| 2007/0031844 A1 | 2/2007 | Khvorova et al. |
| 2007/0149444 A1 | 6/2007 | Laakkonen et al. |
| 2007/0167365 A1 | 7/2007 | Beliveau et al. |
| 2007/0172462 A1 | 7/2007 | Bohn et al. |
| 2007/0197460 A1 | 8/2007 | Fougerolles et al. |
| 2007/0207958 A1 | 9/2007 | Bridon et al. |
| 2008/0014143 A1 | 1/2008 | Ruoslahti et al. |
| 2008/0199436 A1 | 8/2008 | Sawada |
| 2008/0213185 A1 | 9/2008 | Hong et al. |
| 2008/0299039 A1 | 12/2008 | Beliveau et al. |
| 2009/0016959 A1 | 1/2009 | Beliveau et al. |
| 2009/0021883 A1 | 1/2009 | Delida |
| 2009/0082277 A1 | 3/2009 | Beliveau et al. |
| 2009/0215883 A1 | 8/2009 | Bouzada et al. |
| 2009/0221477 A1 | 9/2009 | Artymiuk et al. |
| 2009/0246211 A1 | 10/2009 | Henri et al. |
| 2010/0209429 A1 | 8/2010 | Erlich et al. |
| 2010/0256055 A1 | 10/2010 | Castaigne et al. |
| 2010/0284921 A1 | 11/2010 | Gordon et al. |
| 2010/0297120 A1 | 11/2010 | Beliveau et al. |
| 2011/0039785 A1 | 2/2011 | Beliveau et al. |
| 2011/0059187 A1 | 3/2011 | Basu et al. |
| 2011/0171128 A1 | 7/2011 | Beliveau et al. |
| 2011/0218152 A1 | 9/2011 | Beliveau et al. |
| 2011/0305750 A1 | 12/2011 | Beliveau et al. |
| 2011/0318322 A1 | 12/2011 | Bossard |
| 2012/0015876 A1 | 1/2012 | Castaigne et al. |
| 2012/0156130 A1 | 6/2012 | Hettmann et al. |
| 2012/0245169 A1 | 9/2012 | Ren et al. |
| 2013/0022546 A1 | 1/2013 | Wall et al. |
| 2013/0029982 A1 | 1/2013 | Castro et al. |
| 2013/0029984 A1 | 1/2013 | Castro et al. |
| 2013/0034572 A1 | 2/2013 | Stanimirovic et al. |
| 2013/0035069 A1 | 2/2013 | Fisher |
| 2013/0045873 A1 | 2/2013 | Hood et al. |
| 2013/0150314 A1 | 6/2013 | Myers et al. |
| 2013/0177499 A1 | 7/2013 | Brahmbhatt et al. |
| 2013/0195761 A1 | 8/2013 | Pereira et al. |
| 2015/0037311 A1 | 2/2015 | Boivin et al. |

FOREIGN PATENT DOCUMENTS

| | | |
|---|---|---|
| CA | 2637893 | 7/2007 |
| CA | 2638034 | 7/2007 |
| CN | 101262890 A | 9/2008 |
| CN | 102406949 A | 4/2012 |
| CN | 102552928 A | 7/2012 |
| CN | 102614105 A | 8/2012 |
| DE | 19953696 | 5/2001 |
| EP | 0393431 | 10/1990 |
| EP | 0495049 B1 | 7/1992 |
| EP | 1982699 A1 | 10/2008 |
| EP | 2333074 A1 | 6/2011 |
| JP | 2007-509977 A | 4/2007 |
| RU | 2172323 C2 | 10/1999 |
| WO | WO 87/05702 | 9/1987 |
| WO | WO 96/31531 | 10/1996 |
| WO | WO 1996/35788 | 11/1996 |
| WO | WO-96/39160 A1 | 12/1996 |
| WO | WO 96/39183 | 12/1996 |
| WO | WO 96/40210 | 12/1996 |
| WO | WO 1997/33996 | 9/1997 |
| WO | WO 97/40854 | 11/1997 |
| WO | WO 00/01417 | 1/2000 |
| WO | WO 2000/71574 | 11/2000 |
| WO | WO 01/30319 | 5/2001 |
| WO | WO 02/33090 | 4/2002 |
| WO | WO-02/43765 A2 | 6/2002 |
| WO | WO-02/085923 A2 | 10/2002 |
| WO | WO 03/009815 | 2/2003 |
| WO | WO-03/102583 A1 | 12/2003 |
| WO | WO 2004/060403 | 7/2004 |
| WO | WO 2004/091623 | 10/2004 |
| WO | WO-2004/093897 A1 | 11/2004 |
| WO | WO-2004/108071 A2 | 12/2004 |
| WO | WO 2005/002515 | 1/2005 |
| WO | WO-2005/014625 A1 | 2/2005 |
| WO | WO-2005/021579 A2 | 3/2005 |
| WO | WO-2005/042029 A2 | 5/2005 |
| WO | WO-2006/009902 A2 | 1/2006 |
| WO | WO 2006/086870 | 8/2006 |
| WO | WO-2006/089290 A1 | 8/2006 |
| WO | WO-2006/108052 A2 | 10/2006 |
| WO | WO-2006/138343 A2 | 12/2006 |
| WO | WO 2007/009229 | 1/2007 |
| WO | WO 2007/020085 | 2/2007 |
| WO | WO 2007/030619 | 3/2007 |
| WO | WO-2007/035716 A2 | 3/2007 |
| WO | WO-2007/044323 A2 | 4/2007 |
| WO | WO-2007/070672 A2 | 6/2007 |
| WO | WO-2007/082978 A1 | 7/2007 |
| WO | WO-2007/082979 A1 | 7/2007 |
| WO | WO 2007/103515 | 9/2007 |
| WO | WO 2007/113172 | 10/2007 |
| WO | WO 2008/012629 | 1/2008 |
| WO | WO-2008/036682 A2 | 3/2008 |
| WO | WO 2008/046228 | 4/2008 |
| WO | WO 2008/069876 | 6/2008 |
| WO | WO-2008/116171 A1 | 9/2008 |
| WO | WO 2008/144919 | 12/2008 |
| WO | WO 2009/039188 | 3/2009 |
| WO | WO 2009/046220 | 4/2009 |
| WO | WO 2009/070597 | 6/2009 |
| WO | WO 2009/079790 | 7/2009 |
| WO | WO 2009/105671 | 8/2009 |
| WO | WO 2009/127072 | 10/2009 |
| WO | WO-2010/006239 A2 | 1/2010 |
| WO | WO 2010/043047 | 4/2010 |

(56) References Cited

FOREIGN PATENT DOCUMENTS

| | | |
|---|---|---|
| WO | WO 2010/043049 | 4/2010 |
| WO | WO 2010/063122 | 6/2010 |
| WO | WO 2010/063123 | 6/2010 |
| WO | WO 2010/063124 | 6/2010 |
| WO | WO 2010/069074 | 6/2010 |
| WO | WO 2010/121379 | 10/2010 |
| WO | WO 2010/142035 | 12/2010 |
| WO | WO 2011/000095 | 1/2011 |
| WO | WO-2011/008823 A2 | 1/2011 |
| WO | WO 2011/041897 | 4/2011 |
| WO | WO-2011/063507 A1 | 6/2011 |
| WO | WO-2011/112635 A1 | 9/2011 |
| WO | WO 2011/153642 | 12/2011 |
| WO | WO 2012/000118 | 1/2012 |
| WO | WO-2012/006239 A1 | 1/2012 |
| WO | WO 2012/037687 | 3/2012 |
| WO | WO-2012/064973 A2 | 5/2012 |
| WO | WO-2012/068531 A2 | 5/2012 |
| WO | WO-2012/097000 A1 | 7/2012 |
| WO | WO-2012/118376 A1 | 9/2012 |
| WO | WO-2012/135025 A2 | 10/2012 |
| WO | WO-2012/138694 A2 | 10/2012 |
| WO | WO-2012/153286 A1 | 11/2012 |
| WO | WO-2012/162807 A1 | 12/2012 |
| WO | WO-2013/004716 A1 | 1/2013 |
| WO | WO-2013/012915 A1 | 1/2013 |
| WO | WO-2013/023184 A1 | 2/2013 |
| WO | WO-2013/032591 A1 | 3/2013 |
| WO | WO-2013/049332 A1 | 4/2013 |
| WO | WO-2013/056096 A1 | 4/2013 |
| WO | WO-2013/063468 A1 | 5/2013 |
| WO | WO-2013/071272 A1 | 5/2013 |
| WO | WO-2013/078564 A2 | 6/2013 |
| WO | WO-2013/090861 A1 | 6/2013 |
| WO | WO-2013/120107 A1 | 8/2013 |
| WO | WO-2013/131032 A1 | 9/2013 |
| WO | WO-2013/151774 A1 | 10/2013 |
| WO | WO-2013/162757 A1 | 10/2013 |
| WO | WO-2013/185235 A1 | 12/2013 |
| WO | WO-2014/026283 A1 | 2/2014 |
| WO | WO-2014/026286 A1 | 2/2014 |
| WO | WO-2014/071531 A1 | 5/2014 |
| WO | WO-2014/082184 A1 | 6/2014 |
| WO | WO-2014/194428 A1 | 12/2014 |
| WO | WO-2014/194429 A1 | 12/2014 |

OTHER PUBLICATIONS

Bork, "Powers and Pitfalls in Sequence Analysis: The 70% Hurdle," *Genome Res.* 10:398-400 (2000).
Bork et al., "Go Hunting in Sequence Databases But Watch Out for the Traps," *Trends Genet.* 12:425-427 (1996).
Brenner, "Errors in Genome Annotation," *Trends Genet.* 15:132-133 (1999).
Castex et al., "2-Pyrrolinodoxorubicin and Its Peptide-vectorized Form Bypass Multidrug Resistance," *Anticancer Drugs.* 15:609-617 (2004).
Coon et al., "Solutol HS 15, Nontoxic Polyoxyethylene Esters of 12-hydroxystearic Acid, Reverses Multidrug Resistance," *Cancer Res.* 51:897-902 (1991).
D'Onofrio et al., "Glycomimetics as Decorating Motifs for Oligonucleotides: Solid-phase Synthesis, Stability, and Hybridization Properties of Carbopeptoid-oligonucleotide Conjugates," *Bioconjug Chem.* 16:1299-1309 (2005).
Dagenais et al., "Development of an In Situ Mouse Brain Perfusion Model and Its Application to mdr1a P-glycoprotein-deficient Mice," *J Cereb Blood Flow Metab.* 20:381-386 (2000).
Deane et al., "LRP/Amyloid β-Peptide Interaction Mediates Differential Brain Efflux of Aβ Isoforms," *Neuron.* 43:333-344 (2004).
Dehouck et al., "A New Function for the LDL Receptor: Transcytosis of LDL Across the Blood-Brain Barrier," *J Cell Biol.* 138:877-889 (1997).
Dehouck et al., "An Easier, Reproducible, and Mass-production Method to Study the Blood-brain Barrier in Vitro," *J Neurochem.* 54:1798-1801 (1990).
Dehouck et al., "Drug Transfer Across the Blood-Brain Barrier: Correlation Between In Vitro and In Vivo Models," *J Neurochem.* 58:1790-1797 (1992).
Demeule et al., "High Transcytosis of Melanotransferrin (P97) Across the Blood-Brain Barrier," *J Neurochem.* 83:924-933 (2002).
Demeule et al., "Identification and Design of Peptides As a New Drug Delivery System for the Brain," *J Pharmacol Exp Ther.* 324:1064-1072 (2008).
Demeule et al., "Isolation of Endothelial Cells from Brain, Lung, and Kidney: Expression of the Multidrug Resistance P-Glycoprotein Isoforms," *Biochem Biophys Res Commun.* 281:827-834 (2001).
Doerks et al., "Protein Annotation: Detective Work for Function Prediction," *Trends Genet.* 14:248-250 (1998).
Fillebeen et al., "Receptor-Mediated Transcytosis of Lactoferrin Through the Blood-Brain Barrier," *J Biol Chem.* 274:7011-7017 (1999).
Fromm, "P-glycoprotein: A Defense Mechanism Limiting Oral Bioavailability and CNS Accumulation of Drugs," *Int J Clin Pharmacol Ther.* 38:69-74 (2000).
Gelmon, "The Taxoids: Paclitaxel and Docetaxel," *Lancet.* 344:1267-1272 (1994).
Gewirtz, "A Critical Evaluation of the Mechanisms of Action Proposed for the Antitumor Effects of the Anthracycline Antibiotics Adriamycin and Daunorubicin," *Biochem Pharmacol.* 57:727-741 (1999).
Grabb et al., "Neoplastic and Pharmacological Influence on the Permeability of an in vitro Blood-Brain Barrier," *J Neurosurg.* 82:1053-1058 (1995).
Guillot et al., "Angiotensin Peptide Regulation of Bovine Brain Microvessel Endothelial Cell Monolayer Permeability," *J Cardiovasc Pharmacol.* 18:212-218 (1991).
Gumbleton et al., "Progress and Limitations in the Use of In Vitro Cell Cultures to Serve as a Permeability Screen for the Blood-Brain Barrier," *J Pharm Sci.* 90:1681-1698 (2001).
Hawkins et al., "The Blood-Brain Barrier/Neurovascular Unit in Health and Disease," *Pharmacol Rev.* 57:173-185 (2005).
Hussain et al., "The Mammalian Low-Density Lipoprotein Receptor Family," *Annu Rev Nutr.* 19:141-172 (1999).
Ito et al., "Functional Characterization of the Brain-to-Blood Efflux Clearance of Human Amyloid-β Peptide (1-40) Across the Rat Blood-Brain Barrier," *Neurosci Res.* 56:246-252 (2006).
Ke et al., "Gene Delivery Targeted to the Brain Using an Angiopep-conjugated Polyethyleneglycol-modified Polyamidoamine Dendrimer," *Biomaterials.* 30:6976-6985 (2009).
Kiernan, "Fluorescent-Labelled Aprotinin: A New Reagent for the Histochemical Detection of Acid Mucosubstances," *Histochemie.* 34: 77-84 (1973).
Kobayashi et al., "The Protease Inhibitor Bikunin, a Novel Anti-Metastatic Agent," *Biol Chem.* 384:749-754 (2003).
Koo et al., "Differential Expression of Amyloid Precursor Protein mRNAs in Cases of Alzheimer's Disease and in Aged Nonhuman Primates," *Neuron.* 2:97-104 (1990).
Kounnas et al, "LDL Receptor-related Protein, a Multifunctional ApoE Receptor, Binds Secreted Beta-amyloid Precursor Protein and Mediates Its Degradation," *Cell.* 82:331-340 (1995).
Koziara et al., "In Situ Blood-brain Barrier Transport of Nanoparticles," *Pharm Res.* 20:1772-1778 (2003).
Kreuter et al., "Apolipoprotein-Mediated Transport of Nanoparticle-Bound Drugs Across the Blood-Brain Barrier," *J Drug Target.* 10:317-325 (2002).
Kreuter et al., "Direct Evidence that Polysorbate-80-coated Poly(Butylcyanoacrylate) Nanoparticles Deliver Drugs to the CNS Via Specific Mechanisms Requiring Prior Binding of Drug to the Nanoparticles," *Pharm Res.* 20:409-416 (2003).
Kreuter, "Nanoparticulate Carriers for Drug Delivery to the Brain," *Nanoparticles as Drug Carriers*, Torchilin VP, Imperial College Press, London pp. 527-547 (2006).

(56) References Cited

OTHER PUBLICATIONS

Laccabue et al., "A Novel Taxane Active against an Orthotopically Growing Human Glioma Xenograft," *Cancer.* 92:3085-3092 (2001).

Lai et al., "The Critical Component to Establish in vitro BBB Model: Pericyte," *Brain Res Rev.* 50:258-265 (2005).

Larionova et al., "Carbohydrate-Containing Derivatives of the Trypsin-Kallikrein Inhibitor Aprotinin from Bovine Organs II. Inhibitor Coupled to the (Carboxymethyl)dextran Derivatives of D-Galactose," *Biol Chem Hoppe-Seyler.* 366:743-748 (1985).

Larsson, "Megalin, an Endocytocic Receptor With Signalling Potential," *Acta Universitatis Upsaliensis Uppsala* 1-60 (2006).

Ma et al., "Cationic Charge-Dependent Hepatic Delivery of Amidated Serum Albumin," *J Control Release.* 102:583-594 (2005).

Marinò et al., "Megalin-Mediated Transcytosis of Thyroglobulin by Thyroid Cells is a Calmodulin-Dependent Process," *Thyroid.* 10:461-469 (2000).

Marinò et al., "Transcytosis of Retinol-Binding Protein Across Renal Proximal Tubule Cells After Megalin (gp 330)-Mediated Endocytosis," *J Am Soc Nephrol.* 12:637-648 (2001).

Martel et al., "Transport of Apolipoproteins E and J at the Blood-Brain Barrier Relevance to Alzheimer's disease," *S.T.P. Pharma Sciences.* 7:28-36 (1997).

Mazel et al., "Doxorubicin-peptide Conjugates Overcome Multidrug Resistance," *Anticancer Drugs.* 12:107-116 (2001).

McCarty, "Cell Biology of the Neurovascular Unit: Implications for Drug Delivery Across the Blood-Brain Barrier," *Assay Drug Dev Technol.* 3:89-95 (2005).

Moestrup et al., "Evidence that Epithelial Glycoprotein 330/Megalin Mediates Uptake of Polybasic Drugs," *J.Clin. Invest.* 96:1404-1413 (1995).

Moore et al., "The Role of Flexible Tethers in Multiple Ligand-receptor Bond Formation Between Curved Surfaces," *Biophys J.* 91:1675-1687 (2006).

Muratovska et al., "Conjugate for Efficient Delivery of Short Interfering RNA (siRNA) Into Mammalian Cells," *FEBS Lett.* 558:63-68 (2004).

Ngo et al., "Computational Complexity; Protein Structure Prediction, and the Levinthal Paradox," *The Protein Folding Problem and Tertiary Structure Prediction* Merz, Jr. and Le Grand, Eds. 491-495 (1994).

Niola et al., "A Plasmid-encoded VEGD siRNA Reduces Glioblastoma Angiogenesis and Its Combination with Interleukin-4 Blocks Tumor Growth in a Xenograft Mouse Model," *Cancer Biol Ther.* 5:174-179 (2006).

Orlando et al., "Identification of the Second Cluster of Ligand-Binding Repeats in Megalin as a Site for Receptor-Ligand Interactions," *Proc Natl Acad Sci.* 94:2368-2373 (1997).

Pan et al., "Efficient Transfer of Receptor-Associated Protein (RAP) Across the Blood-Brain Barrier," *J Cell Sci.* 117:5071-5078 (2004).

Pardridge, "Blood-Brain Barrier Biology and Methodology," *J Neurovirol.* 5:556-569 (1999).

Pardridge, "CNS Drug Design Based on Principles of Blood-Brain Barrier Transport," *J Neurochem.* 70:1781-1792 (1998).

Pardridge, "Drug Targeting to the Brain," *Pharm Res.* 24:1733-1744 (2007).

Peri et al., "D-Glucose as a Regioselectively Addressable Scaffold for Combinatorial Chemistry on Solid Phase," *J Carbohydr Chem.* 22:57-71 (2003).

Prince et al., "Lipoprotein Receptor Binding, Cellular Uptake, and Lysosomal Delivery of Fusions Between the Receptor-Associated protein (RAP) and α-L-Iduronidase or Acid α-Glucosidase," *J Biol Chem.* 279:35037-35046 (2004).

Qu et al., "Carbohydrate-based Micelle Clusters Which Enhance Hydrophobic Drug Bioavailability by Up to 1 Order of Magnitude," *Biomacromolecules.* 7:3452-3459 (2006).

Ramakrishnan, "The Role of P-glycoprotein in the Blood-Brain Barrier," *Einstein Q J Biol Med.* 19:160-165 (2003).

Rawat et al., "Lipid Carriers: A Versatile Delivery Vehicle for Proteins and Peptides," *Yakugaku Zasshi.* 128:269-280 (2008).

Régina et al., "Antitumour Activity of ANG1005, a Conjugate Between Paclitaxel and the New Brain Delivery Vector Angiopep-2," *Br J Pharmacol.* 155:185-197 (2008).

Régina et al., "Differences in Multidrug Resistance Phenotype and Matrix Metalloproteinases Activity Between Endothelial Cells from Normal Brain and Glioma," *J Neurochem.* 84:316-324 (2003).

Scherrmann, "Drug Delivery to Brain Via the Blood-Brain Barrier," *Vascul Pharmacol.* 38:349-354 (2002).

Schinkel, "P-Glycoprotein, A Gatekeeper in the Blood-Brain Barrier," *Adv Drug Deliv Rev.* 36:179-194 (1999).

Seidel et al., "Effects of Trasylol on the Blood-Brain Barrier in Rats," *Naunyn Schmiedebergs Arch Pharmacol.* 284:R73 (1974).

Shibata et al., "Clearance of Alzheimer's Amyloid-$\beta_{1-40}$ Peptide From Brain by LDL Receptor-Related Protein-1 at the Blood-Brain Barrier," *J Clin Invest.* 106:1489-1499 (2000).

Shiiki et al., "Brain Insulin Impairs Amyloid-$\beta$(1-40) Clearance From the Brain," *J Neurosci.* 24:9632-9637 (2004).

Shimura et al., "Transport Mechanism of a New Behaviorally Highly Potent Adrenocorticotropic Hormone (ACTH) Analog, Ebiratide, through the Blood-Brain Barrier," *J Pharmacol Exp Ther.* 258:459-465 (1991).

Skolnick et al., "From Genes to Protein Structure and Function: Novel Applications of Computational Approaches in the Genomic Era," *Trends Biotechnol.* 18:34-39 (2000).

Smith, "Brain Perfusion Systems for Studies of Drug Uptake and Metabolism in the Central Nervous System," *Pharm Biotechnol.* 285-307 (1996).

Smith et al., "The Challenges of Genome Sequence Annotation or 'The Devil is in the Details'," *Nat Biotechnol.* 15:1222-1223 (1997).

Steiniger et al., "Chemotherapy of Glioblastoma in Rats Using Doxorubicin-loaded Nanoparticles," *Int J Cancer.* 109:759-767 (2004).

Tamai et al., "Structure-Internalization Relationship for Absorptive-Mediated Endocytosis of Basic Peptides at the Blood-Brain Barrier," *J Pharmacol Exp Ther.* 280:410-415 (1997).

Temsamani et al., "Vector-Mediated Drug Delivery to the Brain," *Expert Opin Biol Ther.* 1:773-782 (2001).

Terasaki et al., "New Approaches to in vitro Models of Blood-Brain Barrier Drug Transport," *Drug Discov Today.* 8:944-954 (2003).

Triguero et al., "Capillary Depletion Method for Quantification of Blood-Brain Barrier Transport of Circulating Peptides and Plasma Proteins," *J Neurochem.* 54:1882-1888 (1990).

Turner et al., "RNA Targeting With Peptide Conjugates of Oligonucleotides, siRNA and PNA," *Blood Cells Mol Dis.* 38:1-7 (2007).

Veronese et al., "PEGylation, Successful Approach to Drug Delivery," *Drug Discov Today.* 10:1451-1458 (2005).

Wang et al., "DNA/dendrimer Complexes Mediate Gene Transfer into Murine Cardiac Transplants ex Vivo," *Mol Ther.* 2:602-608 (2000).

Wells, "Additivity of Mutational Effects in Proteins," *Biochemistry.* 29:8509-8517 (1990).

Witt et al., "Peptide Drug Modifications to Enhance Bioavailability and Blood-Brain Barrier Permeability," *Peptides.* 22:2329-2343 (2001).

Xu et al., "In Vitro and In Vivo Evaluation of Actively Targetable Nanoparticles for Paclitaxel Delivery," *Int J Pharm.* 288:361-368 (2005).

Yepes et al., "Tissue-Type Plasminogen Activator Induces Opening of the Blood-Brain Barrier Via the LDL Receptor-Related Protein," *J Clin Invest.* 112:1533-1540 (2003).

Zhang et al., "Intravenous RNA Interference Gene Therapy Targeting the Human Epidermal Growth Factor Receptor Prolongs Survival in Intracranial Brain Cancer," *Clin Cancer Res.* 10:3667-3677 (2004).

Zhang et al., "Silencing the Epidermal Growth Factor Receptor Gene with RNAi may be Developed as a Potential Therapy for Non Small Cell Lung Cancer," *Genet Vaccines Ther.* 3 (2005).

Zhang et al., "siRNA-containing Liposomes Modified with Polyarginine Effectively Silence the Targeted Gene," *J Control Release.* 112:229-239 (2006).

(56) References Cited

OTHER PUBLICATIONS

Zlokovic et al., "Glycoprotein 330/Megalin: Probable Role in Receptor-mediated Transport of Apolipoprotein J Alone and in a Complex With Alzheimer Disease Amyloid β at the Blood-Brain and Blood-Cerebrospinal Fluid Barriers," *Proc Natl Acad Sci U S A*. 93:4229-4234 (1996).
U.S. Appl. No. 12/601,803, filed Nov. 24, 2009, Beliveau et al.
U.S. Appl. No. 12/632,557, filed Dec. 7, 2009, Castaigne et al.
Arpicco et al., "New Coupling Reagents for the Preparation of Disulfide Cross-Linked Conjugates with Increased Stability," *Bioconjugate Chem*. 8:327-337 (1997).
Banks, "Leptin Transport Across the Blood-Brain Barrier: Implications for the Cause and Treatment of Obesity," *Curr. Pharm. Des*. 7:125-133 (2001).
Banks, "The Blood-Brain Barrier as a Cause of Obesity," *Curr. Pharm. Des*. 14:1606-1614 (2008).
Bicamumpaka et al., "In Vitro Cytotoxicity of Paclitaxel-Transferrin Conjugate on H69 Cells," *Oncol. Rep*. 5:1381-1383 (1998).
Demeule et al., "Drug Transport to the Brain: Key Roles for the Efflux Pump P-Glycoprotein in the Blood-Brain Barrier," *Vascul. Pharmacol*. 38:339-348 (2002).
Dooley et al., "An All D-amino Acid Opioid Peptide with Central Analgesic Activity from a Combinatorial Library," *Science* 266: 2019-2022 (1994).
Eigenbrot et al., "X-Ray Structure of Glial Cell-Derived Neurotrophic Factor at 1.9 ÅResolution and Implications for Receptor Binding," *Nat. Struct. Biol*. 4:435-438 (1997).
Gabius et al., "Targeting of Neoglycoprotein-Drug Conjugates to Cultured Human Embryonal Carcinoma Cells,"*J. Cancer Res. Clin. Oncol*. 113:126-130 (1987).
Gottschalk et al., "Protein Self-Association in Solution: The Bovine Pancreatic Trypsin Inhibitor Decamer," *Biophys. J*. 84: 3941-3958 (2003).
Harkavyi et al., "Glucagon-Like Peptide 1 Receptor Stimulation Reverses Key Deficits in Distinct Rodent Models of Parkinson's Disease," *J. Neuroinflammation*. 5:19 (2008) (pp. 1-9).
Kalra, "Central Leptin Insufficiency Syndrome: An Interactive Etiology for Obesity, Metabolic and Neural Diseases and for Designing New Therapeutic Interventions," *Peptides* 29:127-138 (2008).
Karyekar et al., "*Zonula occludens* Toxin Increases the Permeability of Molecular Weight Markers and Chemotherapeutic Agents Across the Bovine Brain Microvessel Endothelial Cells," *J. Pharm. Sci*. 92:414-423 (2003).
Kirsch et al., "Anti-Angiogenic Treatment Strategies for Malignant Brain Tumors," *J. Neurooncol*. 50:149-163 (2000).
Lewis et al., "Maleimidocysteineamido-DOTA Derivatives: New Reagents for Radiometal Chelate Conjugation to Antibody Sulfhydryl Groups Undergo pH-Dependent Cleavage Reactions," *Bioconjugate Chem*. 9:72-86 (1998).
Saito et al., "Drug Delivery Strategy Utilizing Conjugation Via Reversible Disulfide Linkages: Role and Site of Cellular Reducing Activities," *Adv. Drug. Deliv. Rev*. 55:199-215 (2003).
Samson et al., "Gene Therapy for Diabetes: Metabolic Effects of Helper-Dependent Adenoviral Exendin 4 Expression in a Diet-Induced Obesity Mouse Model," *Mol. Ther*. 16:1805-1812 (2008) (pp. 1-18).
Uekita et al., "Cytoplasmic Tail-Dependent Internalization of Membrane-Type 1 Matrix Metalloproteinase is Important for its Invasion-Promoting Activity," *J. Cell. Biol*. 155:1345-1356 (2001).
Uekita et al., "Membrane-Type 1 Matrix Metalloproteinase Cytoplasmic Tail-Binding Protein-1 is a New Member of the Cupin Superfamily. A Possible Multifunctional Protein Acting as an Invasion Suppressor Down-Regulated in Tumors," *J. Biol. Chem*. 279:12734-12743 (2004).
Akhtar et al., "Nonviral Delivery of Synthetic siRNAs in Vivo," *J. Clin. Invest*. 117: 3623-3632 (2007).
Anonymous, "Blood-Brain Barrier Tackled," <http:www.ecancermedicalscience.com/news-insider-news.asp?itemId326> Oct. 22, 2008.
Bertrand et al., "Transport Characteristics of a Novel Peptide Platform for CNS Therapeutics," *J. Cell Mol. Med*. published online Oct. 10, 2009.
Boules et al., "Bioactive Analogs of Neurotensin: Focus on CNS Effects," *Peptides* 27: 2523-2533 (2006).
Chari, "Targeted Cancer Therapy: Conferring Specificity to Cytotoxic Drugs," *Acc. Chem. Res*. 41:98-107 (2008).
Che et al., "New Angiopep-Modified Doxorubicin (ANG1007) and Etoposide (ANG1009) Chemotherapeutics with Increased Brain Penetration," *J. Med. Chem*. 53: 2814-2824 (2010).
Demeule et al., "Involvement of the Low-Density Lipoprotein Receptor-Related Protein in the Transcytosis of the Brain Delivery Vector Angiopep-2," *J. Neurochem*. 106: 1534-1544 (2008).
Garsky et al., "The Synthesis of a Prodrug of Doxorubicin Designed to Provide Reduced Systemic Toxicity and Greater Target Efficacy," *J. Med. Chem*. 44: 4216-4224 (2001).
Huang et al., "Targeting Delivery of Paclitaxel into Tumor Cells via Somatostatin Receptor Endocytosis," *Chem. Biol*. 7: 453-461 (2000).
Kilic et al., "Intravenous TAT-GDNF is Protective after Focal Cerebral Ischemia in Mice," *Stroke* 34: 1304-1310 (2003).
Kumar et al., "Transvascular Delivery of Small Interfering RNA to the Central Nervous System," *Nature* 448: 39-43 (2007).
Rouselle et al., "New Advances in the Transport of Doxorubicin through the Blood-Brain Barrier by a Peptide Vector-Mediated Strategy," *Mol. Pharmacol*. 57: 679-686 (2000).
Takei et al., "A Small Interfering RNA Targeting Vascular Endothelial Growth Factor as Cancer Therapeutics," *Cancer Res*. 64: 3365-3370 (2004).
Trail et al., "Cure of Xenografted Human Carcinomas by BR96-Doxorubicin Immunoconjugates," *Science* 261:212-215 (1993).
U.S. Appl. No. 61/546,851, filed Oct. 13, 2011, Demeule et al.
Grimm et al., "Ten Year Biochemical Outcomes Following 125-IODINE Monotherapy for Early Stage Prostate Cncer." *Int H. Rad*. 48:146-147 (2000).
Kurzrock et al., "ANGI005: Results of a Phase I study in patients with advanced solid tumors and metastatic brain cancer" Poster B168, EORTC NCIACCR Annual Meeting, 2009.
Mathupala, "Delivery of Small-interfering RNA (siRNA) to the Brain," *Exp. Opin. Ther. Pat*. 19: 137-140, (2009).
Nyalendo et al., "Impaired Tyrosine Phosphorylation of Membrane type 1-Matrix Metalloproteinase Reduces Tumor Cell Proliferation in Three-Dimensional Matrices and Abrogates Tumor Growth in Mice," *Carcinogenesis* 29:1655-1664, (2008).
Sadeghi-aliabadi et al., "Solvent optimization on Taxol extraction from *Taxus baccata* L., using HPLC and LC-MS," *DARU* 17:192-198, (2009).
Schiff and Horwitz, "Taxol Stabilizes Microtubules in Mouse Fibroblast Cells," *Proc Natl Acad Sci USA* 77:1561-1565, (1980).
Tilstra et al., "Protein Transduction: Identification, Characterization and Optimization," *Biochem. Soc. Trans*. 35:811-815, (2007).
Zhang et al., "Tat-modified Leptin is more Accessible to Hypothalamus Through Brain-blood Barrier with a Significant Inhibition of Body-weight Gain in High-fat-diet Fed Mice," *Exp. Clin. Endocrin. Diabet*. 118:31-37 (2010).
International Search Report and Written Opinion for Application No. PCT/CA2009/001779, dated Mar. 10, 2010.
Author manuscript of Howes et al., "Rapid induction of therapeutic hypothermia using convective-immersion surface cooling: Safety, efficacy and outcomes," *Resuscitation* 81: 388-392 (2010).
Demule et al., "ANG2002: A new Angiochem-modified neurotensin with increased brain penetration and analgesic properties," *Program No. 374.11/QQ6 2010 Neuroscience Meeting Planner*, San Diego, CA: Society for Neuroscience (2010).
J.E. Lachowicz et al., "Analgesic properties of a novel brain-penetrant Angiopep-2-neurotensin derivative (ANG2002) for treating chronic pain," *Program No. 173.28/AA9 2012 Neuroscience Meeting Planner*, New Orleans, LA: Society for Neuroscience (2012).
Buvanendran et al., "Recent advances in nonopioid analgesics for acute pain management," *Techniques in Regional Anesthesia and Pain Management* 11: 19-26 (2007).

(56) References Cited

OTHER PUBLICATIONS

Williamson et al., "Expression and purification of recombinant neurotensin in *Escherichia coli*," Protein Expr. Purif. 19: 271-275 (2000).
Yano et al., "Simultaneous activation of two different receptor systems by enkephalin/neurotensin conjugates having spacer chains of various lengths," Eur. J. Pharm. Sci. 7: 41-48 (1998).
Extended European Search Report for EP Patent Application No. 09829934.0, dated Apr. 4, 2013 (13 pages).
Office Action for Japanese Patent Application No. 2011-538809, dated May 13, 2014 (7 pages).
U.S. Appl. No. 61/138,375, Beliveau et al.
Belkin et al., "Matrix-dependent proteolysis of surface transglutaminase by membrane-type metalloproteinase regulates cancer cell adhesion and locomotion," J Biol Chem. 276(21):18415-18422 (2001).
Boado et al., "GDNF fusion protein for targeted-drug delivery across the human blood-brain barrier," Biotechnol Bioeng. 100(2):387-96 (2008).
Brady et al., "Drug design. Refelections on a peptide." Nature. 368(6473):692-693 (1994).
Carell et al., "A novel procedure for the synthesis of libraries containing small organic molecules," Angew Chem Int Ed Engl. 33(20):2059-2061 (1994).
Carell et al., "A solution-phase screening procedure for the isolation of active compounds from a library of molecules," Angew Chem Int Ed Engl. 33(20):2061-2064 (1994).
Chen et al., "Synthesis of doxorubicin conjugates through hydrazone bonds to melanotransferrin P97," Synth Commun. 33(14):2377-2390 (2003).
Cho et al., "An unnatural biopolymer," Science. 261:1303-1305 (1993).
Chu et al., "Detection of soluble P-glycoprotein in culture media and extracellular fluids," Biochem Biophys Res Commun. 203(1):506-512 (1994).
Cui et al., "PAMAM-drug complex for delivering anticancer drug across blood-brain barrier in-vitro and in-vivo," Afr J Pharm Pharmocol. 3(5):227-233 (2009).
Cull et al., "Screening for receptor ligands using large libraries of peptides linked to the C terminus of the lac repressor," Proc Natl Acad Sci U S A. 89(5): 1865-1869 (1992).
D'Ortho et al., "Membrane-type matrix metalloproteinases 1 and 2 exhibit broad-spectrum proteolytic capacities comparable to many matrix metalloproteinases," Eur J Biochem. 250(3): 751-757 (1997).
Declaration of Michel Demeule in European Patent Application No. 11010125 dated Sep. 24, 2012 (4 pages).
DeWitt et al., "'Diversomers': an approach to nonpeptide, nonoligomeric chemical diversity," Proc Natl Acad Sci U S A. 90(15):6909-6913 (1993).
Erb et al., "Recursive deconvolution of combinatorial chemical libraries," Proc Natl Acad Sci U S A. 91(24):11422-11426 (1994).
Evans et al., "Design of nonpeptidal ligands for a peptide receptor: Cholecystokinin antagonists," J Med Chem. 30(7):1229-1239 (1987).
Fauchere et al., "Association with HeLa cells of campylobacter jejuni and campylobacter coli isolated from human feces," Infect Immun. 54(2):283-287 (1986).
Fioretti et al., "Aprotinin-like isoinhibitors in bovine organs," Biol Chem Hoppe Seyler. 369 Suppl:37-42 (1988).
Fodor et al., "Multiplexed biochemical assays with biological chips," Nature. 364(6437):555-556 (1993).
Gabathuler, "Approcaches to transport therapeutic drugs across the blood-brain barrier to treat brain diseases," Neurobiol Dis. 37(1):48-57 (2010).
Gallop et al., "Applications of combinatorial technologies to drug discovery. 1. Background and peptide combinatorial libraries," J Med Chem. 37(9):1233-1251 (1994).

Halab et al., "Design, synthesis, and conformational analysis of azacycloalkane amino acids as conformationally constrained probes for mimicry of peptide secondary structures," Biopolymers. 55(2):101-122 (2000).
Hanessian et al., "Synthesis of (4S)-hydroxymethyl-(2R)-(2-propyl)-butyrolactone: A quest for a practical route to an important hydroxyethylene isostere chiron," Tetrahedron. 53(18):6281-6294 (1997).
Hein et al., "Click chemistry, a powerful tool for pharmaceutical sciences," Pharm Res. 25(10):2216-2230 (2008).
Hijova, Matrix metalloproteinases: their biological functions and clinical implications, Bratisl Lek Listy. 106(3):127-132 (2005).
Hiraoka et al., "Matrix metalloproteinases regulate neovascularization by acting as pericellular fibrinolysins," Cell. 95(3):365-377 (1998).
Hong et al., "Coexpression of cyclooxygenase-2 and matrix metalloproteinases in human aortic atherosclerotic lesions," Yonsei Med J. 41(1):82-88 (2000).
Hotary et al., "Membrane type I matrix metalloproteinase usurps tumor growth control imposed by the three-dimensional extracellular matrix," Cell. 114(1):33-45 (2003).
Huang et al., "Production of bioactive human beta-defensin 5 and 6 in *Escherichia coli* by soluble fusion expression," Protein Expr Purif. 61(2):168-174 (2008).
Hudson et al., "Methionine enkephalin and isosteric analogues. I. Synthesis on a phenolic resin support," Int J Pept Protein Res. 14(3):177-185 (1979).
Imai et al., "Expression of membrane-type 1 matrix metalloproteinase and activation of progelatinase A in human osteoarthritic cartilage," Am J Pathol. 151(1):245-256 (1997).
Itoh et al., "MT1-MMP: a potent modifier of pericellular microenvironment," J Cell Physiol. 206(1):1-8 (2006).
Jameson et al., "A rationally designed CD4 analogue inhibits experimental allergic encephalomyelitis," Nature. 368(6473):744-746 (1994).
Kajita et al., "Membrane-type 1 matrix metalloproteinase cleaves CD44 and promotes cell migration" J Cell Biol. 153(5):893-904 (2001).
Kamps et al., "Uptake of long-circulating immunoliposomes, directed against colon adenocarcinoma cells, by liver metastases of colon cancer," J Drug Target. 8(4):235-245 (2000).
Kesari et al., "Phase II study of temozolomide, thalidomide, and celecoxib for newly diagnosed glioblastoma in adults," Neuro Oncol. 10(3):300-308 (2008).
Kirpotin et al., "Sterically stabilized anti-HER2 immunoliposomes: design and targeting to human breast cancer cells in vitro," Biochemistry. 36(1):66-75 (1997).
Konttinen et al., "Analysis of 16 different matrix metalloproteinases (MMP-1 to MMP-20) in the synovial membrane: different profiles in trauma and rheumatoid arthritis" Ann Rheum Dis. 58(11):691-7 (1999).
Kurzrock et al., "ANG1005, an Angiopep-2/paclitaxel conjugate: The first clinical trial in patients with advanced cancer and brain metastases: Preliminary safety and tolerability data," 20th EORTC-NCI-AACR Symposium on "Molecular Targets and Cancer Therapeutics", Euro J of Cancer. 6(12):133, Abstract 424 (2008).
Lam et al., A new type of synthetic peptide library for identifying ligand-binding activity, Nature. 354(6348):82-4 (1991).
Lam, "Application of combinatorial library methods in cancer research and drug discovery," Anticancer Drug Des. 12(3):145-67 (1997).
Langer, "New methods of drug delivery," Science. 249(4976):1527-33 (1990).
Mamot et al., "Epidermal growth factor receptor (EGFR)-targeted immunoliposomes mediate specific and efficient drug delivery to EGFR- and EGFRvIII-overexpressing tumor cells," Cancer Res. 63(12):3154-61 (2003).
Markman et al., "Phase II trial of weekly single-agent paclitaxel in platinum/paclitaxel-refractory ovarian cancer," J Clin Oncol. 20(9):2365-9 (2002).
Martinez-Fong et al., "Neurotensin-SPDP-poly-L-lysine conjugate: a nonviral vector for targeted gene delivery to neural cells," Molecular Brain Research 69:249-262 (1999).

(56) References Cited

OTHER PUBLICATIONS

Michaud et al., "Risks and benefits of taxanes in breast and ovarian cancer," Drug Saf. 23(5):401-28 (2000).
Moase et al., "Anti-MUC-1 immunoliposomal doxorubicin in the treatment of murine models of metastatic breast cancer," Biochim Biophys Acta. 1510(1-2):43-55 (2001).
Nakada et al., "Expression and tissue localization of membrane-type 1, 2, and 3 matrix metalloproteinases in human astrocytic tumors," Am J Pathol. 154(2):417-28 (1999).
Nam et al., "Sterically stabilized anti-G(M3), anti-Le(x) immunoliposomes: targeting to B16BL6, HRT-18 cancer cells," Oncol Res. 11(1):9-16 (1999).
Nyalendo et al., "Src-dependent phosphorylation of membrane type I matrix metalloproteinase on cytoplasmic tyrosine 573: role in endothelial and tumor cell migration," J Biol Chem. 282(21):15690-9 (2007).
Office Action for Chinese Patent Application No. 200980156242.7, dated Mar. 28, 2013 (13 pages).
Office Action for Russian Patent Application No. 2011125368, dated Sep. 27, 2013 (12 pages).
Pardridge et al. "Combined use of carboxyl-directed protein pegylation and vector-mediated blood-brain barrier drug delivery system optimizes brain uptake of brain-derived neurotrophic factor following intravenous administration," Pharm Res. 15(4):576-582 (1998).
Pardridge et al., "Selective transport of an anti-transferrin receptor antibody through the blood-brain barrier in vivo," J Pharmacol Exp Ther. 259(1):66-70 (1991).
Pardridge, "Vector-mediated drug delivery to the brain," Adv Drug Deliv Rev. 36(2-3):299-321 (1999).
Park et al., "Development of anti-p185HER2 immunoliposomes for cancer therapy," Proc Natl Acad Sci U S A. 92(5):1327-31 (1995).
Park et al., "Recombinant expression of biologically active rat leptin in *Escherichia coli*," Protein Expr Purif. 22(1):60-69 (2001).
Pathan et al. "CNS drug delivery systems: novel approaches," Recent Pat Drug Deliv Formul. 3(1):71-89 (2009).
Pei et al., "Transmembrane-deletion mutants of the membrane-type matrix metalloproteinase-1 process progelatinase A and express intrinsic matrix-degrading activity," J Biol Chem. 271(15):9135-9140 (1996).
Powell et al., "Peptide stability in drug development. II. Effect of single amino acid substitution and glycosylation on peptide reactivity in human serum," Pharm Res. 10(9):1268-73 (1993).
Rajavashisth et al., "Membrane type 1 matrix metalloproteinase expression in human atherosclerotic plaques: evidence for activation by proinflammatory mediators," Circulation. 99(24):3103-9 (1999).
Rizo et al. "Constrained peptides: models of bioactive peptides and protein substructures," Annu Rev Biochem. 61:387-418 (1992).
Rose et al., "Metastatic patterns in histologic variants of ovarian cancer. An autopsy study," Cancer. 64(7):1508-13 (1989).
Rudikoff et al., "Single amino acid substitution altering antigen-binding specificity," Proc Natl Acad Sci USA. 79:1979-83 (1982).
Sabeh et al. "Tumor cell traffic through the extracellular matrix is controlled by the membrane-anchored collagenase MT1-MMP," J Cell Biol. 167(4):769-81 (2004).
Sahm et al. "Receptor binding affinities and biological activities of linear and cyclic melanocortins in B16 murine melanoma cells expressing the native MC1 receptor," J Pharm Pharmacol. 48(2):197-200 (1996).
Scott et al. "Searching for peptide ligands with an epitope library," Science. 249(4967):386-90 (1990).
Seiden et al., "A phase II study of the MDR inhibitor biricodar (INCEL, VX-710) and paclitaxel in women with advanced ovarian cancer refractory to paclitaxel therapy," Gynecol Oncol. 86(3):302-10 (2002).
Shao et al., "Angiopep-2 modified PE-PEG based polymeric micelles for amphotericin B delivery targeted to the brain," J Control Release. 147(1):118-126 (2010).

Spatola et al., "Structure-activity relationships of enkephalins containing serially replaced thiomethylene amide bond surrogates," Life Sci. 38(14):1243-9 (1986).
Svenson et al., "Dendrimers in biomedical applications—reflections on the field," Adv Drug Deliv Rev. 57(15):2106-2129 (2005).
UniProtKB Entry P08183 (MDR1_HUMAN), "Multidrug resistance proteins 1(EC 3.6.3.44) (ATP-binding cassette DE subfamily B member 1) (P-glycoprotein 1) (CD243 antigen)," Sep. 18, 2013 (16 pages).
Vincent, "Neurotensin receptors: binding properties, transduction pathways, and structure," Cellular and Molecular Neurobiology 15(5):501-512 (1995).
Wang et al., "Polyamidoamine dendrimers with a modified Pentaerythritol core having high efficiency and low cytotoxicity as gene carriers," Biomacromolecules. 10(3):617-622 (2009).
Wang et al., "Synthesis and antinociceptive effects of endomorphin-1 analogs with C-terminal linked by oligoarginine," Peptides. 32(2):293-9 (2011).
Zhai et al. "Expression of membrane type 1 matrix metalloproteinase is associated with cervical carcinoma progression and invasion," Cancer Res. 65(15):6543-6550 (2005).
Zhang et al. "In vitro gene delivery using polyamidoamine dendrimers with a trimesyl core," Biomacromolecules. 6(1):341-350 (2005).
Back et al., "The effect of aprotinin on the harmine-induced tremor in lymphostatic encephalopathic and normal rats," Eur J Pharmacol. 32(02):365-9 (1975).
Castaigne et al., "425 POSTER ANG1005: Preliminary clinical safety and tolerability in patients with recurrent malignant glioma," Eur J Cancer. 6(12):133-134 (2008).
Demeule et al., "Conjugation of a brain-penetrant peptide with neurotensin provides antinociceptive properties," J Clin Invest. 124(3):1199-1213 (2014) (15 pages).
Egleton et al., "Development of neuropeptide drugs that cross the blood-brain barrier," NeuroRx 2(1):44-53 (2005).
Examination Report for Australian Patent Application No. 2009322043, dated Mar. 3, 2014 (4 pages).
Gabathuler et al., "117 POSTER ANG1005, Paclitaxel conjugated to the angiopep brain transport vector for the treatment of brain cancer: preclinical studies," Eur J Cancer. 6(12):38-9 (2008).
Gabathuler et al., "147 POSTER A new Taxol delivery system for the treatment of brain primary or metastatic tumors," Eur J Cancer. 4(12):47-8 (2006).
Gaillard et al., "Targeted delivery across the blood-brain barrier," Expert Opin Drug Deliv. 2(2):299-309 (2005).
Haspel et al., "System for cleavable Fc fusion proteins using tobacco etch virus (TEV) protease," Biotechniques. 30(1):60, 61, 64-66 (2001).
Huang et al., "Dual targeting effect of Angiopep-2-modified, DNA-loaded nanoparticles for glioma," Biomaterials. 32:6832-8 (2011).
Kurzrock et al., "424 POSTER ANG1005, an Angiopep-2/paclitaxel conjugate: the first clinical trial in patients with advanced cancer and brain metastases: Preliminary safety and tolerability data," Eur J Cancer. 6(12):133 (2008).
Moroz et al., "Long-circulated polymer-aprotinin conjugates," Poster Presentations P-IV Plasminogen Activator Inhibitors. Abstract 116. pp. 37 (1996) (Abstract Only).
Notice of Reasons for Rejection for Japanese Patent Application No. 2011-538809, dated May 13, 2014 (7 pages).
Office Action and its English translation for Chinese Patent Application No. 200980156242.7, dated Jan. 27, 2014 (13 pages).
Office Action for Canadian Application No. 2,745,524, dated Jan. 28, 2016 (6 pages).
Patel et al., "Getting into the brain: approaches to enhance brain drug delivery," CNS Drugs. 23(1):35-58 (2009).
Régina et al., "Antitumour activity of ANG1005, a conjugate between paclitaxel and the new brain delivery vector Angiopep-2," Br J Pharmacol. 155(2):185-97 (2008).
Shao et al., "Angiopep-2 modified PE-PEG based polymeric micelles for amphotericin B delivery targeted to the brain," J Control Release. 147(1):118-26 (2010).

(56) References Cited

OTHER PUBLICATIONS

Xin et al., "Angiopep-conjugated poly(ethylene glycol)-co-poly(epsilon-caprolactone) nanoparticles as dual-targeting drug delivery system for brain glioma," Biomaterials. 32(18):4293-305 (2011).

Xin et al., "The brain targeting mechanism of Angiopep-conjugated poly(ethylene glycol)-co-poly(epsilon-caprolactone) nanoparticles," Biomaterials. 33(5):1673-81 (2012).

Haspel et al., "System for cleavable Fc fusion proteins using tobacco etch virus (TEV) protease," Biotechniques. 30:60-66 (2001).

Office Action for Japanese Patent Application No. 2011-538809, dated May 13, 2014 (4 pages).

Moroz et al., "Long-circulated polymer-aprotinin conjugates," Poster Presentations P-IV Plasminogen Activator Inhibitors 37 (1996). Abstract 116.

Xin et al., "Angiopep-conjugated poly(ethylene glycol)-co-poly($\epsilon$-caprolactone) nanoparticles as dual-targeting drug delivery system for brain glioma," Biomaterials 32(18):4293-305 (2011).

\* cited by examiner

CONJUGATES OF NEUROTENSIN OR NEUROTENSIN ANALOGS AND USES THEREOF

CROSS-REFERENCE TO RELATED APPLICATIONS

This application claims the benefit of U.S. Provisional Application Nos. 61/225,486, filed Jul. 14, 2009; 61/181,144, filed May 26, 2009; and 61/200,947, filed Dec. 5, 2008, each of which is hereby incorporated by reference.

REFERENCE TO A SEQUENCE LISTING

A sequence listing is provided in this patent document as a .txt file entitled "50546.031005 Seq Listing_ST25.txt," created Feb. 23, 2010 (size 50.4 kB). The content of this file is hereby incorporated by reference.

BACKGROUND OF THE INVENTION

The invention relates to compounds including neurotensin, a neurotensin analog, or a neurotensin receptor agonist bound to a peptide vector and uses thereof. Neurotensin is 13 amino acid peptide possessing numerous biological activities. Injections of neurotensin in the central nervous system produce, among other effects, antipsychotic and hypothermic effects. Intravenous delivery of neurotensin, however, does not result in these effects, as the blood-brain barrier (BBB) effectively prevents peripheral neurotensin from reaching the receptors in the central nervous system (CNS) receptors.

Reduction of body temperature (hypothermia) provides one of the best forms of neuroprotection against brain damage resulting from injury (e.g., in subjects who have suffered from a nerve, brain, or spinal cord injury, or stroke). Prior to the present invention, methods for reducing body temperature have been inadequate. Physical means for reducing body temperature include the use of external methods (e.g., cooling blankets, cooling helmet, ice packs, and ice baths) as well as the use of internal methods (e.g., cooling probes, infusion of cold fluid). These techniques can be complex and expensive, and can lead to delays in the onset of hypothermia. Sustained maintenance of hypothermia may also be difficult using these methods. Finally, these methods can cause severe shivering, necessitating the need for co-medications such as paralytic agents or sedatives. Given the number of strokes (795,000), cardiac arrests of cardiac origin (325,000), severe traumatic head injuries (300,000), and open heart surgeries (694,000) each year in the United States where hypothermic treatment can be beneficial, there is a need for improved methods of inducing hypothermia.

In the development of a new therapy for brain pathologies, the BBB is considered a major obstacle for the potential use of drugs for treating disorders of the CNS. The global market for CNS drugs was $68 billion in 2006, which was roughly half that of global market for cardiovascular drugs, even though in the United States, nearly twice as many people suffer from CNS disorders as from cardiovascular diseases. The reason for this imbalance is, in part, that more than 98% of all potential CNS drugs do not cross the BBB. In addition, more than 99% of worldwide CNS drug development is devoted solely to CNS drug discovery, and less than 1% is directed to CNS drug delivery. This may explain the lack of therapeutic options available for major neurological diseases.

The brain is shielded against potentially toxic substances by the presence of two barrier systems: the BBB and the blood-cerebrospinal fluid barrier (BCSFB). The BBB is considered to be the major route for the uptake of serum ligands since its surface area is approximately 5000-fold greater than that of BCSFB. The brain endothelium, which constitutes the BBB, represents the major obstacle for the use of potential drugs against many disorders of the CNS. As a general rule, only small lipophilic molecules may pass across the BBB, i.e., from circulating systemic blood to brain. Many drugs that have a larger size or higher hydrophobicity show high efficacy in CNS targets but are not efficacious in animals as these drugs cannot effectively cross the BBB. Thus, peptide and protein therapeutics are generally excluded from transport from blood to brain, owing to the negligible permeability of the brain capillary endothelial wall to these drugs. Brain capillary endothelial cells (BCECs) are closely sealed by tight junctions, possess few fenestrae and few endocytic vesicles as compared to capillaries of other organs. BCECs are surrounded by extracellular matrix, astrocytes, pericytes, and microglial cells. The close association of endothelial cells with the astrocyte foot processes and the basement membrane of capillaries are important for the development and maintenance of the BBB properties that permit tight control of blood-brain exchange.

Thus, there exists a need for improved delivery of neurotensin to its target sites.

SUMMARY OF THE INVENTION

The peptide neurotensin has a number of clinical uses, including the ability to reduce body temperature. Many of these applications, however, require that the peptide cross the blood-brain barrier (BBB).

Neurotensin, by itself, is unable to cross the BBB. We have therefore synthesized compounds that include (a) a polypeptide therapeutic selected from the group consisting of neurotensin, a neurotensin analog (e.g., pELYENK-PRRPYIL-OH, where "pE" represents L-pyroglutamic acid (SEQ ID NO:117), human neurotensin(8-13) (NT(8-13)), Ac-Lys[D-Tyr$^{11}$]NT(8-13), Ac-Lys-NT(8-13), pE-Lys-NT(8-13), or a neurotensin receptor agonist and (b) a peptide vector capable of transporting the peptide therapeutic across the blood-brain barrier (BBB) or into particular cell types. These compounds are useful in treating any disorder where increased neurotensin activity is desired, particularly where transport of the polypeptide therapeutic across the BBB or into a particular cell type is desired. In one particular example, the compound includes neurotensin or a neurotensin fragment which may be used to reduce body temperature (e.g., in a patient who is in need of neuroprotection and/or has had a stroke, heart attack, nerve injury (e.g., spinal chord, head, or brain injury, such as a traumatic brain injury, or is having major surgery such as cardiac surgery or open heart surgery), to treat a patient suffering from a psychiatric disorder (e.g., schizophrenia, obsessive compulsive disorder, or Tourette's syndrome), or to treat a patient suffering from a metabolic disorder such as diabetes and obesity. In other cases, the compound may be able to either increase or reduce blood pressure in a patient. The compound may be capable of inducing hypothermia, upon either a single or upon an infusion for a period of at least 1, 2, 3, 4, 6, 8, 10, 12, 15, 18, 21, 24, 30, 36, or 48 hours following initial administration. The peptide vector is capable of transporting the polypeptide therapeutic either across the blood-brain barrier (BBB) or into a particular cell type (e.g., liver, lung, kidney, spleen, and muscle). Because the conjugates are targeted across the BBB or to particular cell types, therapeutic efficacy can be achieved using lower doses or less frequent dosing as compared to the unconjugated peptide therapeutic, thus reducing the severity of or incidence of side effects and/or increasing efficacy. The compound may also exhibit increased stability, improved pharmacokinetics, or reduced degradation in vivo, as compared to the unconjugated peptide therapeutic.

Accordingly, in a first aspect the invention features a compound having the formula:

A-X-B where A is a peptide vector capable of being transported across the blood-brain barrier (BBB) or into a particular cell type (e.g., liver, lung, kidney, spleen, and muscle), X is a linker, and B is a peptide therapeutic selected from the group consisting of neurotensin, a neurotensin analog (e.g., pELYENKPRRPYIL-OH, where pE is pyroglutamic acid (SEQ ID NO:117)), or a neurotensin receptor agonist (e.g., any of those described herein). The transport across the BBB or into the cell may be increased by at least 10%, 25%, 50%, 75%, 100%, 200%, 500%, 750%, 1000%, 1500%, 2000%, 5000%, or 10,000%. The compound may be substantially pure. The compound may be formulated with a pharmaceutically acceptable carrier (e.g., any described herein).

In certain embodiments, B includes or is a polypeptide substantially identical to human neurotensin or to a human neurotensin fragment (e.g., neurotensin(8-13) and neurotensin(9-13)). In certain embodiments, the glutamate at position 1 of neurotensin is substituted with pyroglutamic acid. In certain embodiments, the neurotensin analog is substantially identical to human neurotensin. In certain embodiments, B acts as an agonist to any of the neurotensin receptors (neurotensin receptor type 1 (NTR1), neurotensin receptor type 2 (NTR2), neurotensin receptor 3 (NTR3)). In certain embodiments, the neurotensin receptor agonist is selective (e.g., binds and/or activates to a degree at least 2, 5, 10, 50, 100, 500, 1000, 5000, 10,000, 50,000, or 100,000 greater) for one of NTR1, NTR2, or NTR3 over at least one of the other receptors.

In particular embodiments, the compound has the structure:

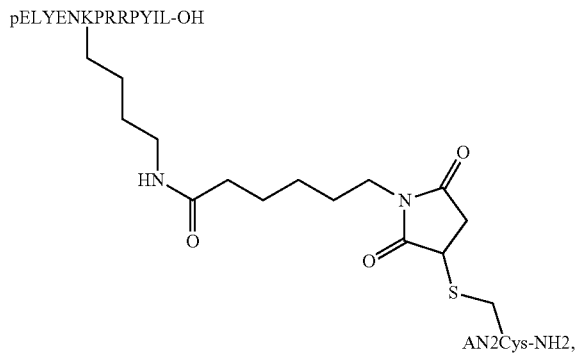

AN2Cys-NH2, where the —(CH$_2$)$_4$NH— moiety attached to the lysine of the pELYENKPRRPYIL (SEQ ID NO:117) sequence represents the side chain of that lysine, and the —CH$_2$S— moiety attached to the C-terminal cysteine of the AN2Cys sequence represents the side chain of that cysteine, and AN2 represents the sequence of Angiopep-2 (SEQ ID NO:97).

In another aspect, the invention features methods of making the compound A-X-B. In one embodiment, the method includes conjugating the peptide vector (A) to a linker (X), and conjugating the peptide vector-linker (A-X) to a peptide therapeutic (B), thereby forming the compound A-X-B. In another embodiment, the method includes conjugating the peptide therapeutic (B) to a linker (X), and conjugating the peptide therapeutic/linker (X-B) to a peptide vector (A), thereby forming the compound A-X-B. In another embodiment, the method includes conjugating the peptide vector (A) to a peptide therapeutic (B), where either A or B optionally include a linker (X), to form the compound A-X-B.

In another aspect, the invention features a nucleic acid molecule that encodes the compound A-X-B, where the compound is a polypeptide. The nucleic acid molecule may be operably linked to a promoter and may be part of a nucleic acid vector. The vector may be in a cell, such as a prokaryotic cell (e.g., bacterial cell) or eukaryotic cell (e.g., yeast or mammalian cell, such as a human cell).

In another aspect, the invention features methods of making a compound of the formula A-X-B, where A-X-B is a polypeptide. In one embodiment, the method includes expressing a nucleic acid vector of the previous aspect in a cell to produce the polypeptide; and purifying the polypeptide.

In another aspect, the invention features a method of reducing a subject's body temperature. The method includes administering a compound of the first aspect in an amount sufficient to reduce the body temperature of the subject. The subject may be suffering from, or may have recently suffered from, a stroke, cerebral ischemia, cardiac ischemia, or a nerve injury such as a brain injury (e.g., a traumatic brain injury) or a spinal chord injury or may be in need of neuroprotection. The subject may be suffering from malignant hyperthermia or may be undergoing or about to undergo surgery (e.g., major surgery such as cardiac surgery).

In another aspect, the invention features a method of reducing pain or inducing analgesia by administering in a compound of the first aspect to a subject in need thereof. The subject may be suffering from an acute pain (e.g., selected from the group consisting of mechanical pain, heat pain, cold pain, ischemic pain, and chemical-induced pain). In other embodiments, the subject is suffering from peripheral or central neuropathic pain, inflammatory pain, migraine-related pain, headache-related pain, irritable bowel syndrome-related pain, fibromyalgia-related pain, arthritic pain, skeletal pain, joint pain, gastrointestinal pain, muscle pain, angina pain, facial pain, pelvic pain, claudication, postoperative pain, post traumatic pain, tension-type headache, obstetric pain, gynecological pain, or chemotherapy-induced pain.

In another aspect, the invention features a method of reducing pain sensitivity in a subject by administering a compound (e.g., an effective amount) of the first aspect to a subject.

In another aspect, the invention features a method of treating (e.g., prophylactically) a metabolic disorder in a subject. The method includes administering a compound of the first aspect of the invention to a subject in an amount sufficient to treat the metabolic disorder. The metabolic disorder may be diabetes (e.g., Type I or Type II), obesity, diabetes as a consequence of obesity, hyperglycemia, dyslipidemia, hypertriglyceridemia, syndrome X, insulin resistance, impaired glucose tolerance (IGT), diabetic dyslipidemia, hyperlipidemia, a cardiovascular disease, or hypertension. The subject may be overweight, obese, or bulimic.

In another aspect, the invention features a method of treating (e.g., prophylactically) a disorder selected from the group consisting of anxiety, obsessive-compulsive disorder, Tourette's syndrome, movement disorder, aggression, psychosis, seizures, panic attacks, hysteria, sleep disorders, Alzheimer's disease, and Parkinson's disease. The method includes administering a compound of the first aspect of the invention to a subject in an amount sufficient to treat or prevent the disorder. The psychosis may be schizophrenia.

In another aspect, the invention features a method of treating drug addiction or reducing drug abuse in a subject in need thereof. The drug may be a psychostimulant such as amphetamine, methamphetamine, 3,4-methylenedioxymethamphetamine, nicotine, cocaine, methylphenidate, or arecoline. In other embodiments, the drug is alcohol.

In another aspect, the invention features a method of modulating (e.g., increasing or decreasing) blood pressure in a subject (e.g., a subject suffering from either hypertension or hypotension).

In any of the methods involving administration of a compound to a subject, the amount sufficient may be less than 90%, 75%, 50%, 40%, 30%, 20%, 15%, 10%, 5%, 4%, 3%, 2%, 1%, or 0.1% of the amount required for an equivalent dose of the polypeptide therapeutic (e.g., any described herein) when not conjugated to the peptide vector. The amount sufficient may reduce a side effect as compared to administration of an effective amount of the polypeptide therapeutic when not conjugated to the peptide vector. The subject may be a mammal such as a human.

In any of the above aspects, the peptide vector may be a polypeptide substantially identical to any of the sequences set Table 1, or a fragment thereof. In certain embodiments, the peptide vector has a sequence of Angiopep-1 (SEQ ID NO:67), Angiopep-2 (SEQ ID NO:97), Angiopep-3 (SEQ ID NO:107), Angiopep-4-a (SEQ ID NO:108), Angiopep-4-b (SEQ ID NO:109), Angiopep-5 (SEQ ID NO:110), Angiopep-6 (SEQ ID NO:111), or Angiopep-7 (SEQ ID NO:112)). The peptide vector or conjugate may be efficiently transported into a particular cell type (e.g., any one, two, three, four, or five of liver, lung, kidney, spleen, and muscle) or may cross the mammalian BBB efficiently (e.g., Angiopep-1, -2, -3, -4a, -4b, -5, and -6). In another embodiment, the peptide vector or conjugate is able to enter a particular cell type (e.g., any one, two, three, four, or five of liver, lung, kidney, spleen, and muscle) but does not cross the BBB efficiently (e.g., a conjugate including Angiopep-7). The peptide vector may be of any length, for example, at least 6, 7, 8, 9, 10, 11, 12, 13, 14, 15, 16, 17, 18, 19, 20, 21, 25, 35, 50, 75, 100, 200, or 500 amino acids, or any range between these numbers. In certain embodiments, the peptide vector is 10 to 50 amino acids in length. The polypeptide may be produced by recombinant genetic technology or chemical synthesis.

TABLE 1

Exemplary Peptide Vectors

| SEQ ID NO: | Sequence |
|---|---|
| 1 | T F V Y G G C R A K R N N F K S A E D |
| 2 | T F Q Y G G C M G N G N N F V T E K E |
| 3 | P F F Y G G C G G N R N N F D T E E Y |
| 4 | S F Y Y G G C L G N K N N Y L R E E E |
| 5 | T F F Y G G C R A K R N N F K R A K Y |
| 6 | T F F Y G G C R G K R N N F K R A K Y |
| 7 | T F F Y G G C R A K K N N Y K R A K Y |
| 8 | T F F Y G G C R G K K N N F K R A K Y |
| 9 | T F Q Y G G C R A K R N N F K R A K Y |
| 10 | T F Q Y G G C R G K K N N F K R A K Y |
| 11 | T F F Y G G C L G K R N N F K R A K Y |
| 12 | T F F Y G G S L G K R N N F K R A K Y |
| 13 | P F F Y G G C G G K K N N F K R A K Y |
| 14 | T F F Y G G C R G K G N N Y K R A K Y |
| 15 | P F F Y G G C R G K R N N F L R A K Y |
| 16 | T F F Y G G C R G K R N N F K R E K Y |
| 17 | P F F Y G G C R A K K N N F K R A K E |
| 18 | T F F Y G G C R G K R N N F K R A K D |
| 19 | T F F Y G G C R A K R N N F D R A K Y |
| 20 | T F F Y G G C R G K K N N F K R A E Y |
| 21 | P F F Y G G C G A N R N N F K R A K Y |
| 22 | T F F Y G G C G G K K N N F K T A K Y |
| 23 | T F F Y G G C R G N R N N F L R A K Y |
| 24 | T F F Y G G C R G N R N N F K T A K Y |
| 25 | T F F Y G G S R G N R N N F K T A K Y |
| 26 | T F F Y G G C L G N G N N F K R A K Y |
| 27 | T F F Y G G C L G N R N N F L R A K Y |
| 28 | T F F Y G G C L G N R N N F K T A K Y |
| 29 | T F F Y G G C R G N G N N F K S A K Y |
| 30 | T F F Y G G C R G K K N N F D R E K Y |
| 31 | T F F Y G G C R G K R N N F L R E K E |
| 32 | T F F Y G G C R G K G N N F D R A K Y |
| 33 | T F F Y G G S R G K G N N F D R A K Y |
| 34 | T F F Y G G C R G N G N N F V T A K Y |
| 35 | P F F Y G G C G G K G N N Y V T A K Y |
| 36 | T F F Y G G C L G K G N N F L T A K Y |
| 37 | S F F Y G G C L G N K N N F L T A K Y |
| 38 | T F F Y G G C G G N K N N F V R E K Y |
| 39 | T F F Y G G C M G N K N N F V R E K Y |
| 40 | T F F Y G G S M G N K N N F V R E K Y |
| 41 | P F F Y G G C L G N R N N Y V R E K Y |

TABLE 1-continued

Exemplary Peptide Vectors

| SEQ ID NO: | Sequence |
|---|---|
| 42 | T F F Y G G C L G N R N N F V R E K Y |
| 43 | T F F Y G G C L G N K N N Y V R E K Y |
| 44 | T F F Y G G C G G N G N N F L T A K Y |
| 45 | T F F Y G G C R G N R N N F L T A E Y |
| 46 | T F F Y G G C R G N G N N F K S A E Y |
| 47 | P F F Y G G C L G N K N N F K T A E Y |
| 48 | T F F Y G G C R G N R N N F K T E E Y |
| 49 | T F F Y G G C R G K R N N F K T E E D |
| 50 | P F F Y G G C G G N G N N F V R E K Y |
| 51 | S F F Y G G C M G N G N N F V R E K Y |
| 52 | P F F Y G G C G G N G N N F L R E K Y |
| 53 | T F F Y G G C L G N G N N F V R E K Y |
| 54 | S F F Y G G C L G N G N N Y L R E K Y |
| 55 | T F F Y G G S L G N G N N F V R E K Y |
| 56 | T F F Y G G C R G N G N N F V T A E Y |
| 57 | T F F Y G G C L G K G N N F V S A E Y |
| 58 | T F F Y G G C L G N R N N F D R A E Y |
| 59 | T F F Y G G C L G N R N N F L R E E Y |
| 60 | T F F Y G G C L G N K N N Y L R E E Y |
| 61 | P F F Y G G C G G N R N N Y L R E E Y |
| 62 | P F F Y G G S G G N R N N Y L R E E Y |
| 63 | M R P D F C L E P P Y T G P C V A R I |
| 64 | A R I I R Y F Y N A K A G L C Q T F V Y G |
| 65 | Y G G C R A K R N N Y K S A E D C M R T C G |
| 66 | P D F C L E P P Y T G P C V A R I I R Y F Y |
| 67 | T F F Y G G C R G K R N N F K T E E Y |
| 68 | K F F Y G G C R G K R N N F K T E E Y |
| 69 | T F Y Y G G C R G K R N N Y K T E E Y |
| 70 | T F F Y G G S R G K R N N F K T E E Y |
| 71 | C T F F Y G C C R G K R N N F K T E E Y |
| 72 | T F F Y G G C R G K R N N F K T E E Y C |
| 73 | C T F F Y G S C R G K R N N F K T E E Y |
| 74 | T F F Y G G S R G K R N N F K T E E Y C |
| 75 | P F F Y G G C R G K R N N F K T E E Y |
| 76 | T F F Y G G C R G K R N N F K T K E Y |
| 77 | T F F Y G G K R G K R N N F K T E E Y |
| 78 | T F F Y G G C R G K R N N F K T K R Y |
| 79 | T F F Y G G K R G K R N N F K T A E Y |
| 80 | T F F Y G G K R G K R N N F K T A G Y |
| 81 | T F F Y G G K R G K R N N F K R E K Y |
| 82 | T F F Y G G K R G K R N N F K R A K Y |
| 83 | T F F Y G G C L G N R N N F K T E E Y |
| 84 | T F F Y G C R G K R N N F K T E E Y |
| 85 | T F F Y G G R C G K R N N F K T E E Y |
| 86 | T F F Y G G C L G N G N N F D T E E E |
| 87 | T F Q Y G G C R G K R N N F K T E E Y |
| 88 | Y N K E F G T F N T K G C E R G Y R F |
| 89 | R F K Y G G C L G N M N N F E T L E E |
| 90 | R F K Y G G C L G N K N N F L R L K Y |
| 91 | R F K Y G G C L G N K N N Y L R L K Y |
| 92 | K T K R K R K K Q R V K I A Y E E I F K N Y |
| 93 | K T K R K R K K Q R V K I A Y |
| 94 | R G G R L S Y S R R F S T S T G R |
| 95 | R R L S Y S R R R F |
| 96 | R Q I K I W F Q N R R M K W K K |
| 97 | T F F Y G G S R G K R N N F K T E E Y |
| 98 | M R P D F C L E P P Y T G P C V A R I I R Y F Y N A K A G L C Q T F V Y G G C R A K R N N F K S A E D C M R T C G G A |
| 99 | T F F Y G G C R G K R N N F K T K E Y |
| 100 | R F K Y G G C L G N K N N Y L R L K Y |
| 101 | T F F Y G G C R A K R N N F K R A K Y |
| 102 | N A K A G L C Q T F V Y G G C L A K R N N F E S A E D C M R T C G G A |
| 103 | Y G G C R A K R N N F K S A E D C M R T C G G A |
| 104 | G L C Q T F V Y G G C R A K R N N F K S A E |
| 105 | L C Q T F V Y G G C E A K R N N F K S A |
| 107 | T F F Y G G S R G K R N N F K T E E Y |
| 108 | R F F Y G G S R G K R N N F K T E E Y |
| 109 | R F F Y G G S R G K R N N F K T E E Y |
| 110 | R F F Y G G S R G K R N N F R T E E Y |
| 111 | T F F Y G G S R G K R N N F R T E E Y |
| 112 | T F F Y G G S R G R R N N F R T E E Y |
| 113 | C T F F Y G G S R G K R N N F K T E E Y |

TABLE 1-continued

Exemplary Peptide Vectors

| SEQ ID NO: | |
|---|---|
| 114 | T F F Y G G S R G K R N N F K T E E Y C |
| 115 | C T F F Y G G S R G R R N N F R T E E Y |
| 116 | T F F Y G G S R G R R N N F R T E E Y C |

Polypeptides Nos. 5, 67, 76, and 91, include the sequences of SEQ ID NOS: 5, 67, 76, and 91, respectively, and are amidated at the C-terminus.
Polypeptides Nos. 107, 109, and 110 include the sequences of SEQ ID NOS: 97, 109, and 110, respectively, and are acetylated at the N-terminus.

In any of the above aspects, the peptide vector may include an amino acid sequence having the formula:

X1-X2-X3-X4-X5-X6-X7-X8-X9-X10-X11-X12-X13-X14-X15-X16-X17-X18-X19 where each of X1-X19 (e.g., X1-X6, X8, X9, X11-X14, and X16-X19) is, independently, any amino acid (e.g., a naturally occurring amino acid such as Ala, Arg, Asn, Asp, Cys, Gln, Glu, Gly, His, Ile, Leu, Lys, Met, Phe, Pro, Ser, Thr, Trp, Tyr, and Val) or absent and at least one (e.g., 2 or 3) of X1, X10, and X15 is arginine. In some embodiments, X7 is Ser or Cys; or X10 and X15 each are independently Arg or Lys. In some embodiments, the residues from X1 through X19, inclusive, are substantially identical to any of the amino acid sequences of any one of SEQ ID NOS:1-105 and 107-116 (e.g., Angiopep-1, Angiopep-2, Angiopep-3, Angiopep-4a, Angiopep-4b, Angiopep-5, Angiopep-6, and Angiopep-7). In some embodiments, at least one (e.g., 2, 3, 4, or 5) of the amino acids X1-X19 is Arg. In some embodiments, the polypeptide has one or more additional cysteine residues at the N-terminal of the polypeptide, the C-terminal of the polypeptide, or both.

In certain embodiments of any of the above aspects, the peptide vector or polypeptide therapeutic is modified (e.g., as described herein). The peptide or polypeptide may be amidated, acetylated, or both. Such modifications may be at the amino or carboxy terminus of the polypeptide. The peptide or polypeptide may also include peptidomimetics (e.g., those described herein) of any of the polypeptides described herein. The peptide or polypeptide may be in a multimeric form, for example, dimeric form (e.g., formed by disulfide bonding through cysteine residues).

In certain embodiments, the peptide vector or polypeptide therapeutic (e.g., neurotensin) has an amino acid sequence described herein with at least one amino acid substitution (e.g., 2, 3, 4, 5, 6, 7, 8, 9, 10, 11, or 12 substitutions), insertion, or deletion or is substantially identical to an amino acid sequence described herein. The peptide or polypeptide may contain, for example, 1 to 12, 1 to 10, 1 to 5, or 1 to 3 amino acid substitutions, for example, 1 to 10 (e.g., to 9, 8, 7, 6, 5, 4, 3, 2) amino acid substitutions. The amino acid substitution(s) may be conservative or non-conservative. For example, the peptide vector may have an arginine at one, two, or three of the positions corresponding to positions 1, 10, and 15 of the amino acid sequence of any of SEQ ID NO:1, Angiopep-1, Angiopep-2, Angiopep-3, Angiopep-4a, Angiopep-4b, Angiopep-5, Angiopep-6, and Angiopep-7. In certain embodiments, the polypeptide therapeutic may have a cysteine or lysine substitution or addition at any position (e.g., a lysine substitution at the N- or C-terminal position).

In any of the above aspects, the compound may specifically exclude a polypeptide including or consisting of any of SEQ ID NOS:1-105 and 107-116 (e.g., Angiopep-1, Angiopep-2, Angiopep-3, Angiopep-4a, Angiopep-4b, Angiopep-5, Angiopep-6, and Angiopep-7). In some embodiments, the polypeptides and conjugates of the invention exclude the polypeptides of SEQ ID NOs:102, 103, 104, and 105.

In any of the above aspects, the linker (X) may be any linker known in the art or described herein. In particular embodiments, the linker is a covalent bond (e.g., a peptide bond), a chemical linking agent (e.g., those described herein), an amino acid or a peptide (e.g., 2, 3, 4, 5, 8, 10, or more amino acids). In certain embodiments, the linker has the formula:

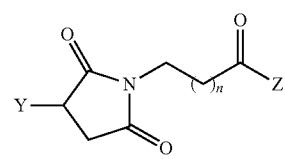

where n is an integer between 2 and 15 (e.g., 2, 3, 4, 5, 6, 7, 8, 9, 10, 11, 12, 13, 14, or 15); and either Y is a thiol on A and Z is a primary amine on B or Y is a thiol on B and Z is a primary amino on A.

By "peptide vector" is meant a compound or molecule such as a polypeptide or a polypeptide mimetic that can be transported into a particular cell type (e.g., liver, lungs, kidney, spleen, or muscle) or across the BBB. The vector may be attached to (covalently or not) or conjugated to an agent and thereby may be able to transport the agent into a particular cell type or across the BBB. In certain embodiments, the vector may bind to receptors present on cancer cells or brain endothelial cells and thereby be transported into the cancer cell or across the BBB by transcytosis. The vector may be a molecule for which high levels of transendothelial transport may be obtained, without affecting the cell or BBB integrity. The vector may be a polypeptide or a peptidomimetic and may be naturally occurring or produced by chemical synthesis or recombinant genetic technology.

By "neurotensin receptor agonist" is meant a compound (e.g., a polypeptide) capable of activating at least one neurotensin receptor as compared to a control compound. Neurotensin receptor activities include production of inositol phosphate.

By "substantially identical" is meant a polypeptide or nucleic acid exhibiting at least 35%, 40%, 50%, 55%, 60%, 65%, 70%, 75%, 85%, 90%, 95%, or even 99% identity to a reference amino acid or nucleic acid sequence. For polypeptides, the length of comparison sequences will generally be at least 4 (e.g., at least 5, 6, 7, 8, 9, 10, 11, 12, 13, 14, 15, 16, 17, 18, 19, 20, 25, 50, or 100) amino acids. For nucleic acids, the length of comparison sequences will generally be at least 60 nucleotides, preferably at least 90 nucleotides, and more preferably at least 120 nucleotides, or full length. It is to be understood herein that gaps may be found between the amino acids of an analogs that are identical or similar to amino acids of the original polypeptide. The gaps may include no amino acids, one or more amino acids that are not identical or similar to the original polypeptide. Biologically active analogs of the vectors (polypeptides) of the invention are encompassed herewith. Percent identity may be determined, for example, with n algorithm GAP, BESTFIT, or FASTA in the Wisconsin Genetics Software Package Release 7.0, using default gap weights.

By "treating" a disease, disorder, or condition in a subject is meant reducing at least one symptom of the disease, disorder, or condition by administrating a therapeutic agent to the subject.

By "treating prophylactically" a disease, disorder, or condition in a subject is meant reducing the frequency of occurrence or severity of (e.g., preventing) a disease, disorder or condition by administering to the subject a therapeutic agent to the subject prior to the appearance of a disease symptom or symptoms.

In one example, a subject who is being treated for a particular condition is one who a medical practitioner has diagnosed as having that condition. Diagnosis may be performed by any suitable means, such as those described herein. A subject in whom the development of the condition is being treated prophylactically may or may not have received such a diagnosis. One in the art will understand that subject of the invention may have been subjected to standard tests or may have been identified, without examination, as one at high risk due to the presence of one or more risk factors.

By "a metabolic disorder" is meant any pathological condition resulting from an alteration in a subject's metabolism. Such disorders include those resulting from an alteration in glucose homeostasis resulting, for example, in hyperglycemia. According to this invention, an alteration in glucose levels is typically an increase in glucose levels by at least 5%, 10%, 20%, 30%, 40%, 50%, 60%, 70%, 80%, 90%, or even 100% relative to such levels in a healthy individual. Metabolic disorders include obesity and diabetes (e.g., diabetes type I, diabetes type II, MODY, and gestational diabetes), satiety, and endocrine deficiencies of aging.

By "subject" is meant a human or non-human animal (e.g., a mammal).

By "equivalent dosage" is meant the amount of a compound of the invention required to achieve the same molar amount of the peptide therapeutic in the compound of the invention, as compared to the unconjugated polypeptide therapeutic. For example, the equivalent dosage of 1.0 µg neurotensin is about 2.5 µg of the neurotensin/Angiopep-2-Cys-NH$_2$ conjugate described herein.

By a polypeptide which is "efficiently transported across the BBB" is meant a polypeptide that is able to cross the BBB at least as efficiently as Angiopep-6 (i.e., greater than 38.5% that of Angiopep-1 (250 nM) in the in situ brain perfusion assay described in U.S. patent application Ser. No. 11/807,597, filed May 29, 2007, hereby incorporated by reference). Accordingly, a polypeptide which is "not efficiently transported across the BBB" is transported to the brain at lower levels (e.g., transported less efficiently than Angiopep-6).

By a polypeptide or compound which is "efficiently transported to a particular cell type" is meant that the polypeptide or compound is able to accumulate (e.g., either due to increased transport into the cell, decreased efflux from the cell, or a combination thereof) in that cell type to at least a 10% (e.g., 25%, 50%, 100%, 200%, 500%, 1,000%, 5,000%, or 10,000%) greater extent than either a control substance, or, in the case of a conjugate, as compared to the unconjugated agent. Such activities are described in detail in International Application Publication No. WO 2007/009229, hereby incorporated by reference.

Other features and advantages of the invention will be apparent from the following Detailed Description, the drawings, and the claims.

DETAILED DESCRIPTION

Figure 1A:
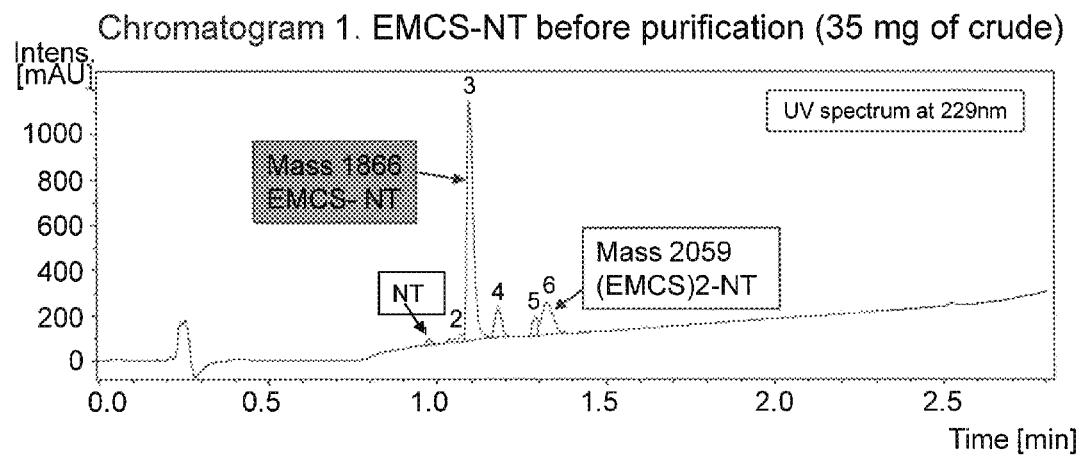
FIGS. 1A and 1B are chromatograms showing the ECMS-Neurotensin compound (ECMS-NT) before (FIG. 1A) and after (FIG. 1B) purification using the analytical method described in the examples.

We have developed neurotensin conjugates having an enhanced ability to cross the blood-brain barrier (BBB) or to enter particular cell type(s) (e.g., liver, lung, kidney, spleen, and muscle). Surprisingly, we have shown that the compounds of the invention, as compared to unconjugated neurotensin peptide, are far more effective in causing a neurotensin response, such as a reduction in body temperature, as compared to unconjugated neurotensin. Because the compounds of the invention exhibit higher response, lower doses of the conjugated peptides can be effectively, and may be used to reduce or eliminate side effects. Alternatively, the observed increased efficacy can result in a greater therapeutic effect using higher doses. Indeed, these compounds, unlike certain prior hypothermic techniques, are capable of rapidly inducing a sustainable hypothermic response (e.g., over a period of at least 3, 4, 5, 6, 8, 10, 12, 15, 18, 21, 24, 30, 36, or 48 hours) without inducing shivering.

Neurotensin

Neurotensin (NT) is a 13 amino acid peptide found in the central nervous system and in the gastrointestinal tract. In brain, NT is associated with dopaminergic receptors and other neurotransmitter system. Peripheral NT acts as a paracrine and endocrine peptide on both the digestive and cardiovascular systems. To exert its biological effects in the brain NT has to be injected or delivered directly to the brain because NT does not cross the BBB and is rapidly degraded by peptidases following systematic administration. Preclinical pharmacological studies, most of which involve direct injection of NT into the brain, strongly suggest that an agonist of NT receptors would be clinically useful for the treatment of neuropsychiatric conditions including psychosis, schizophrenia, Parkinson's disease, pain, and the abuse of psychostimulants. In particular, in various animal studies, intraventricular injection of NT led to hypothermia and analgesia in antinociception experiments.

The peptide therapeutic may be neurotensin or analog thereof. Human neurotensin is a thirteen amino acid peptide having the sequence QLYENKPRRPYIL (SEQ ID NO:162). Exemplary neurotensin analogs include (VIP-neurotensin) hybrid antagonist, acetylneurotensin(8-13), JMV 1193, KK13 peptide, neuromedin N, neuromedin N precursor, neurotensin(1-10), neurotensin(1-11), neurotensin(1-13), neurotensin(1-6), neurotensin(1-8), neurotensin(8-13), Asp (12)-neurotensin(8-13), Asp(13)-neurotensin(8-13), Lys(8)-neurotensin(8-13), N-methyl-Arg(8)-Lys(9)-neo-Trp(11)-neo-Leu(12)-neurotensin(8-13), neurotensin(9-13), neurotensin 69L, Arg(9)-neurotensin, azidobenzoyl-Lys(6)-Trp(11)-neurotensin, Gln(4)-neurotensin, iodo-Tyr(11)-neurotensin, iodo-Tyr(3)-neurotensin, N-α-(fluoresceinylthio-carbamyl)glutamyl(1)-neurotensin, Phe(11)-neurotensin, Ser(7)-neurotensin, Trp(11)-neurotensin, Tyr(11)-neurotensin, rat NT77, PD 149163, proneurotensin, stearyl-Nle (17)-neurotensin(6-11)VIP(7-28), $^{99m}$Tc-NT-XI, TJN 950, and vasoactive intestinal peptide-neurotensin hybrid.

Other neurotensin analogs include NT64L [L-neo-Trp11] NT(8-13), NT72D [D-Lys9,D-neo-Trp11,tert-Leu12]NT(9-13), NT64D [D-neo-Trp11]NT(8-13), NT73L [D-Lys9, L-neo-Trp11]NT(9-13), NT65L [L-neo-Trp11, tert-Leu12] NT(8-13), NT73D [D-Lys9,D-neo-Trp11]NT(9-13), NT65D [D-neo-Trp11, tert-Leu12]NT(8-13), NT74L [DAB9, L-neo-Trp11,tert-Leu12]NT(9-13), NT66L [D-Lys8, L-neo-Trp11, tert-Leu12]NT(8-13), NT74D [DAB9,Pro,D-neo-Trp11, tert-Leu12]NT(9-13), NT66D [D-Lys8, D-neo-Trp11, tert-Leu12]NT(8-13), NT75L [DAB8 L-neo-Trp11] NT(8-13), NT67L [D-Lys8, L-neo-Trp11]NT(8-13), NT75D [DAB8,D-neo-Trp1 1]NT(8-13), NT67D [D-Lys8, D-neo-Trp1 1]NT(8-13), NT76L [D-Orn9, L-neo-Trp11]NT(8-13), NT69L [N-methyl-Arg8, L-Lys9 L-neo-Trp11,tert-Leu12] NT(8-13), NT76D [D-Orn9,D-neo-Trp11]NT(8-13), NT69D [N-methyl-Arg8 L-Lys9,D-neo-Trp11,tert-Leu12] NT(8-13), NT77L [D-Orn9, L-neo-Trp11,tert-Leu12]NT(8-13), NT71L [N-methyl-Arg8,DAB9 L-neo-Trp11,tert-Leu12]NT(8-13), NT77D [D-Orn9,D-neo-Trp11,tert-Leu12]NT(8-13), NT71D [N-methyl-Arg8,DAB9,D-neo-Trp11,tert-Leu12]NT(8-13), NT78L [N-methyl-Arg8,D-Orn9 L-neo-Trp11,tert-Leu12]NT(8-13), NT72L [D-Lys9, L-neo-Trp11,tert-Leu12]NT(9-13), and NT78D [N-methyl-Arg8,D-Orn9,D-neo-Trp11,tert-Leu12]NT(8-13), where neo-Trp is (2-amino-3-[1H-indolyl]propanoic acid). Other neurotensin analogs include Beta-lactotensin (NTR2 selective), JMV-449, and PD-149 or PD-163 (NTR1 selective; reduced amide bond 8-13 fragment of neurotensin).

Still other NT analogs include guinea pig NT, [Gln$^4$]NT, [D-Trp$^{11}$]NT(9-13), frog NT, [Gln$^4$]NT, [D-Phe$^{11}$]NT, [D-Trp$^{11}$]NT, [D-Tyr$^{11}$]NT, Ac-NT(8-13), [Lys$^{8,9}$]NT(8-13), [3,5-diBr-Tyr$^{11}$]NT, Nα-Acetyl-NT(8-13), Nα,Nε-di-Boc-[Lys$^9$]NT(9-13) methyl ester, Boc-[Lys$^9$]NT(9-13)-methyl ester, [Trp$^{11}$]NT, [Dab$^9$]NT (8-13), [Lys$^9$,Trp$^{11}$, Glu$^{12}$]NT(8-13) (Cyclo(-Arg-Lys-Pro-Trp-Glu)-Leu-OH (SEQ ID NO:118)), [Lys$^8$-(®)-Lys$^9$]NT(8-13) (where ® is a CH$_2$NH replacement of the peptide bond), DTPA-DLys-Pro-Gly(PipAm)-Arg-(4-oxo)Pro-Tyr-tBuGly-Leu-OH, DTPA-DLys-Pro-Gly(PipAm)-Arg-Pro-(2,6diMe)Tyr-tBuGly-Leu-OH, DTPA-DLys-Pro-Gly(PipAm)-Arg-Pro-mTyr-tBuGly-Leu-OH, wherein mTyr stands for metatyrosine such that the —OH group of the Tyr is in the meta position, DTPA-DLys-Pro-Gly(PipAm)-PipGly-Pro-Tyr-tBuGly-Leu-OH, DTPA-DLys-Pro-Gly(PipAm)-Arg-AzeCA-Tyr-tBuGly-Leu-OH, DTPA-DLys-AzeCA-Gly(PipAm)-Arg-Pro-Tyr-tBuGly-Leu-OH, DTPA-DLys-Pro-Gly(PipAm)-Arg-Pro-Tyr-Achc-Leu-OH, DTPA-DLys-Pro-Gly(PipAm)-Arg-Pro-Tyr-tBuGly-Cpa-OH, DTPA-DLys-Pro-Gly(PipAm)-Arg-Pro-Tyr-tBuGly-Cha-OH, DTPA-DLys-Pro-Gly(PipAm)-Arg-Pro-Tyr-tBuGly-tBuAla-OH, DTPA-DLys-Pro-Gly(PipAm)-Arg-PipCA-Tyr-tBuGly-Leu-OH, DTPA-DLys-Pro-Gly(PipAm)-Arg-DPipCA-Tyr-tBuGly-Leu-OH, DTPA-DLys-Pro-Gly(PipAm)-Arg-Pro-Tyr-Chg-Leu-OH, DTPA-DLys-Pro-Gly(PipAm)-Arg-Pro-DTyr-tBu-Gly-Leu-OH, and those described in U.S. Patent Application Publication 2009/0062212: D-Lys L-Arg L-Pro L-Tyr L-Ile L-Leu, L-Arg D-Lys L-Pro L-Tyr L-Ile L-Leu, L-Arg D-Arg L-Pro L-Tyr L-Ile L-Leu, L-Arg L-Arg L-Pro L-Tyr L-Ile D-Leu, L-Arg L-Arg Gly L-Tyr L-Ile L-Leu (SEQ ID NO:119), L-Arg L-Arg L-Pro L-Ala L-Ile L-Leu (SEQ ID NO:120), L-Arg L-Arg L-Pro L-Tyr L-Leu L-Leu (SEQ ID NO:121), L-Arg L-Arg L-Pro L-Tyr L-Val L-Leu (SEQ ID NO:122), D-Arg L-Arg L-Pro L-Tyr L-Ile L-Leu, D-Arg D-Arg L-Pro L-Tyr L-Ile L-Leu, D-Arg L-Lys L-Pro L-Tyr L-Ile L-Leu, L-Lys D-Arg L-Pro L-Tyr L-Ile L-Leu, L-Lys L-Arg L-Pro L-Tyr L-Ile L-Leu (SEQ ID NO:123), L-Arg L-Lys L-Pro L-Tyr L-Ile L-Leu (SEQ ID NO:124), L-Lys L-Lys L-Pro L-Tyr L-Ile L-Leu (SEQ ID NO:125), D-Lys D-Lys L-Pro L-Tyr L-Ile L-Leu, L-Orn L-Arg L-Pro L-Tyr L-Ile L-Leu (SEQ ID NO:126), D-Orn L-Arg L-Pro L-Tyr L-Ile L-Leu, L-Arg L-Orn L-Pro L-Tyr L-Ile L-Leu (SEQ ID NO:127), L-Arg D-Orn L-Pro L-Tyr L-Ile L-Leu, L-Orn L-Orn L-Pro L-Tyr L-Ile L-Leu (SEQ ID NO:128), L-Orn D-Orn L-Pro L-Tyr L-Ile L-Leu, D-Orn L-Orn L-Pro L-Tyr L-Ile L-Leu, D-Orn D-Orn L-Pro L-Tyr L-Ile L-Leu, DAB L-Arg L-Pro L-Tyr L-Ile L-Leu (SEQ ID NO:129), L-Arg DAB L-Pro L-Tyr L-Ile L-Leu (SEQ ID NO:130), DAB DAB L-Pro L-Tyr L-Ile L-Leu (SEQ ID NO:131), L-Arg L-Arg L-Pro CHA L-Ile L-Leu (SEQ ID NO:132), L-Arg L-Arg L-Pro L-3,2-Nal-L-Ile L-Leu (SEQ ID NO:133), L-Orn L-Pro L-Tyr L-Ile L-Leu (SEQ ID NO:134), D-Orn L-Pro L-Tyr L-Ile L-Leu, L-Arg L-Orn L-Pro D-Tyr L-Ile L-Leu, L-Arg D-Orn L-Pro D-Tyr L-Ile L-Leu, DAP L-Arg L-Pro L-Tyr L-Ile L-Leu (SEQ ID NO:135), L-Arg DAP L-Pro L-Tyr L-Ile L-Leu (SEQ ID NO:136), DAP DAP L-Pro L-Tyr L-Ile L-Leu (SEQ ID NO:137), L-Arg L-homoArg L-Pro L-Tyr L-Ile L-Leu (SEQ ID NO: 138), L-homoArg L-homoArg L-Pro L-Tyr L-Ile L-Leu (SEQ ID NO:139), L-homoArg L-Arg L-Pro L-Tyr L-Ile L-Leu (SEQ ID NO:140), L-Arg L-Arg L-Pro L-TIC L-Ile L-Leu (SEQ ID NO:141), L-Arg L-Arg L-Pro D-TIC L-Ile L-Leu, L-Arg L-Arg L-Pro L-3,1-Nal L-Ile L-Leu (SEQ ID NO:142), L-Arg L-Arg L-Pro D-3,1-Nal L-Ile L-Leu, L-Arg L-Arg L-Pro D-3,2-Nal L-Ile L-Leu, L-Arg L-Arg L-Pip L-Tyr L-Ile L-Leu (SEQ ID NO:143), p-Glu L-Leu L-Tyr L-Glu L-Asn L-Lys L-Pro BPA L-Arg L-Pro L-Tyr L-Ile L-Leu (SEQ ID NO:144), p-Glu L-Leu L-Tyr L-Glu BPA L-Lys L-Pro L-Arg L-Arg L-Pro L-Tyr L-Ile L-Leu (SEQ ID NO:145), p-Glu L-Leu L-Tyr L-Glu L-Asn L-Lys L-Pro L-Arg BPA L-Pro L-Tyr L-Ile L-Leu (SEQ ID NO:146), L-Arg DAB L-Pro L-3,1-Nal L-Ile L-Leu (SEQ ID NO:147), p-Glu L-Leu L-Tyr L-Glu L-Asn L-Lys L-Pro L-Arg L-Orn L-Pro L-Tyr L-Ile L-Leu (SEQ ID NO:148), p-Glu L-Leu L-Tyr L-Glu L-Asn L-Lys L-Pro L-Arg D-Orn L-Pro L-Tyr L-Ile L-Leu, p-Glu L-Leu L-Tyr L-Glu L-Asn L-Lys L-Pro L-Arg L-Arg L-Pro L-3,1-Nal L-Ile L-Leu (SEQ ID NO:149), L-Arg L-Arg L-Pro L-neo-Trp L-Ile L-Leu (SEQ ID NO:150), L-Arg L-Arg L-Pro L-neo-Trp tert-Leu L-Leu (SEQ ID NO:151), D-Lys L-Arg L-Pro L-neo-Trp tert-Leu L-Leu, D-Lys L-Arg L-Pro L-Trp tert-Leu L-Leu, D-Lys L-Arg L-Pro L-neo-Trp L-Ile L-Leu, D-Lys L-Arg L-Pro L-Trp L-Ile L-Leu, N- methyl-Arg L-Lys L-Pro L-neo-Trp tert-Leu L-Leu (SEQ ID NO:152), p-Glu L-Leu L-iodo-Tyr L-Glu L-Asn L-Lys L-Pro L-Arg L-Arg L-Pro L-Tyr L-Ile L-Leu (SEQ ID NO:153), N-methyl-Arg DAB L-Pro L-neo-Trp tert-Leu L-Leu (SEQ ID NO:154), D-Lys L-Pro L-neo-Trp tert-Leu L-Leu, D-Lys L-Pro L-neo-Trp L-Ile L-Leu, DAB L-Arg L-Pro L-neo-Trp L-Ile L-Leu (SEQ ID NO:155), L-Arg D-Orn L-Pro L-neo-Trp tert-Leu L-Leu, L-Arg D-Orn L-Pro L-Trp tert-Leu L-Leu, N-methyl-Arg D-Orn L-Pro L-neo-Trp tert-Leu L-Leu, N-methyl-Arg D-Orn L-Pro L-Trp tert-Leu L-Leu, N-methyl Arg L-Arg L-Pro D-3,1-Nal tert-Leu L-Leu, and N-methyl-Arg L-Arg L-Pro D-3,1-Nal L-Ile L-Leu. Abbreviations: BPA=benzoylphenylalanine; CHA=cyclohexylalanine; DAB=diaminobutyric acid; DAP=diaminoproprionic acid; homoArg=homoarginine; Orn=ornithine; Nal=naphthyl-alanine; Pip=1-pipecolinic acid; neo-Trp=a regio-isomer of the native tryptophan (Fauq et al., Tetrahedron: Asymmetry 9:4127-34 (1998)); TIC=1,2,3,4-tetrahydroisoquinoline-3-carboxylic acid).

Other neurotensin analogs include those with modified amino acids (e.g., any of those described herein). The neurotensin analog may be selective for NTR1, NTR2, or NTR3 (e.g., may bind to or activate one of NTR1, NTR2, or NTR3 at least 2, 5, 10, 50, 100, 500, 1000, 5000, 10,000, 50,000, or 100,000 greater) as compared to at least one of the other NTR receptors or both.

Modified Forms of Polypeptide Therapeutics

Any of the polypeptide therapeutics described herein (e.g., neurotensin, a neurotensin analog, or neurotensin receptor agonist) may be modified (e.g., as described herein or as known in the art). As described in U.S. Pat. No. 6,924,264, the polypeptide can be bound to a polymer to increase its molecular weight. Exemplary polymers include polyethylene glycol polymers, polyamino acids, albumin, gelatin, succinyl-gelatin, (hydroxypropyl)-methacrylamide, fatty acids, polysaccharides, lipid amino acids, and dextran.

In one case, the polypeptide is modified by addition of albumin (e.g., human albumin), or an analog or fragment thereof, or the Fc portion of an immunoglobulin. Such an approach is described, for example, in U.S. Pat. No. 7,271,149.

In one example, the polypeptide is modified by addition of a lipophilic substituent, as described in PCT Publication WO 98/08871. The lipophilic substituent may include a partially or completely hydrogenated cyclopentanophenathrene skeleton, a straight-chain or branched alkyl group; the acyl group of a straight-chain or branched fatty acid (e.g., a group including $CH_3(CH_2)_nCO-$ or $HOOC(CH_2)_mCO-$, where n or m is 4 to 38); an acyl group of a straight-chain or branched alkane α,ω-dicarboxylic acid; $CH_3(CH_2)_p((CH_2)_q COOH)CHNH-CO(CH_2)_2CO-$, where p and q are integers and p+q is 8 to 33; $CH_3(CH_2)_rCO-NHCH(COOH)(CH_2)_2CO-$, where r is 10 to 24; $CH_3(CH_2)_sCO-NHCH((CH_2)_2COOH)CO-$, where s is 8 to 24; $COOH(CH_2)_tCO-$, where t is 8 to 24; $-NHCH(COOH)(CH_2)_4NH-CO(CH_2)_uCH_3$, where u is 8 to 18; $-NHCH(COOH)(CH_2)_4NH-COCH((CH_2)_2COOH)NH-CO(CH_2)_wCH_3$, where w is 10 to 16; $-NHCH(COOH)(CH_2)_4NH-CO(CH_2)_2CH(COOH)NH-CO(CH_2)_xCH_3$, where x is 10 to 16; or $-NHCH(COOH)(CH_2)_4NH-CO(CH_2)_2CH(COOH)NHCO(CH_2)_yCH_3$, where y is 1 to 22.

In other embodiments, the polypeptide therapeutic is modified by addition of a chemically reactive group such as a maleimide group, as described in U.S. Pat. No. 6,593,295.

These groups can react with available reactive functionalities on blood components to form covalent bonds and can extending the effective therapeutic in vivo half-life of the modified polypeptides. To form covalent bonds with the functional group on a protein, one can use as a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxysulfosuccinimide (sulfo-NHS), maleimide-benzoyl-succinimide (MBS), gamma-maleimido-butyryloxy succinimide ester (GMBS), maleimido propionic acid (MPA) maleimido hexanoic acid (MHA), and maleimido undecanoic acid (MUA).

Primary amines are the principal targets for NHS esters. Accessible α-amine groups present on the N-termini of proteins and the 8-amine of lysine react with NHS esters. An amide bond is formed when the NHS ester conjugation reaction reacts with primary amines releasing N-hydroxysuccinimide. These succinimide containing reactive groups are herein referred to as succinimidyl groups. In certain embodiments of the invention, the functional group on the protein will be a thiol group and the chemically reactive group will be a maleimido-containing group such as gamma-maleimide-butrylamide (GMBA or MPA). Such maleimide containing groups are referred to herein as maleido groups.

The maleimido group is most selective for sulfhydryl groups on peptides when the pH of the reaction mixture is 6.5-7.4. At pH 7.0, the rate of reaction of maleimido groups with sulfhydryls (e.g., thiol groups on proteins such as serum albumin or IgG) is 1000-fold faster than with amines. Thus, a stable thioether linkage between the maleimido group and the sulfhydryl is formed, which cannot be cleaved under physiological conditions.

Peptide Vectors

The compounds of the invention can feature any of polypeptides described herein, for example, any of the peptides described in Table 1 (e.g., Angiopep-1 or Angiopep-2), or a fragment or analog thereof. In certain embodiments, the polypeptide may have at least 35%, 40%, 50%, 60%, 70%, 80%, 90%, 95%, 99%, or even 100% identity to a polypeptide described herein. The polypeptide may have one or more (e.g., 2, 3, 4, 5, 6, 7, 8, 9, 10, 11, 12, 13, 14, or 15) substitutions relative to one of the sequences described herein. Other modifications are described in greater detail below.

The invention also features fragments of these polypeptides (e.g., a functional fragment). In certain embodiments, the fragments are capable of efficiently being transported to or accumulating in a particular cell type (e.g., liver, eye, lung, kidney, or spleen) or are efficiently transported across the BBB. Truncations of the polypeptide may be 1, 2, 3, 4, 5, 6, 7, 8, 9, 10, 11, 12, or more amino acids from either the N-terminus of the polypeptide, the C-terminus of the polypeptide, or a combination thereof. Other fragments include sequences where internal portions of the polypeptide are deleted.

Additional polypeptides may be identified by using one of the assays or methods described herein. For example, a candidate polypeptide may be produced by conventional peptide synthesis, conjugated with paclitaxel and administered to a laboratory animal. A biologically-active polypeptide conjugate may be identified, for example, based on its ability to increase survival of an animal injected with tumor cells and treated with the conjugate as compared to a control which has not been treated with a conjugate (e.g., treated with the unconjugated agent). For example, a biologically active polypeptide may be identified based on its location in the parenchyma in an in situ cerebral perfusion assay.

Assays to determine accumulation in other tissues may be performed as well. Labeled conjugates of a polypeptide can be administered to an animal, and accumulation in different organs can be measured. For example, a polypeptide conjugated to a detectable label (e.g., a near-IR fluorescence spectroscopy label such as Cy5.5) allows live in vivo visualization. Such a polypeptide can be administered to an animal, and the presence of the polypeptide in an organ can be detected, thus allowing determination of the rate and amount of accumulation of the polypeptide in the desired organ. In other embodiments, the polypeptide can be labelled with a radioactive isotope (e.g., $^{125}$I) The polypeptide is then administered to an animal. After a period of time, the animal is sacrificed and the organs are extracted. The amount of radioisotope in each organ can then be measured using any means known in the art. By comparing the amount of a labeled candidate polypeptide in a particular organ relative to the amount of a labeled control polypeptide, the ability of the candidate polypeptide to access and accumulate in a particular tissue can be ascertained. Appropriate negative controls include any peptide or polypeptide known not to be efficiently transported into a particular cell type (e.g., a peptide related to Angiopep that does not cross the BBB, or any other peptide).

Additional sequences are described in U.S. Pat. No. 5,807,980 (e.g., SEQ ID NO:102 herein), U.S. Pat. No. 5,780,265 (e.g., SEQ ID NO:103), U.S. Pat. No. 5,118,668 (e.g., SEQ ID NO:105). An exemplary nucleotide sequence encoding an aprotinin analog atgagaccag atttctgcct cgagccgccg tacactgggc cctgcaaagc tcgtatcatc cgttacttct acaatgcaaa ggcaggcctg tgtcagacct tcgtatacgg cggctgcaga gctaagcgta acaacttcaa atccgcggaa gactgcatgc gtacttgcgg tggtgcttag; SEQ ID NO:156; Genbank accession No. X04666). Other examples of aprotinin analogs may be found by performing a protein BLAST (Genbank: wvvw.ncbi.nlm.nih.gov/BLAST/) using the synthetic aprotinin sequence (or portion thereof) disclosed in International Application No. PCT/CA2004/000011. Exemplary aprotinin analogs are also found under accession Nos. CAA37967 (GI:58005) and 1405218C (GI:3604747).

Modified Polypeptides

The peptide vectors and polypeptide therapeutics used in the invention may have a modified amino acid sequence. In certain embodiments, the modification does not destroy significantly a desired biological activity (e.g., ability to cross the BBB or neurotensin agonist activity). The modification may reduce (e.g., by at least 5%, 10%, 20%, 25%, 35%, 50%, 60%, 70%, 75%, 80%, 90%, or 95%), may have no effect, or may increase (e.g., by at least 5%, 10%, 25%, 50%, 100%, 200%, 500%, or 1000%) the biological activity of the original polypeptide. The modified peptide or polypeptide may have or may optimize a characteristic of a polypeptide, such as in vivo stability, bioavailability, toxicity, immunological activity, immunological identity, and conjugation properties.

Modifications include those by natural processes, such as posttranslational processing, or by chemical modification techniques known in the art. Modifications may occur anywhere in a polypeptide including the polypeptide backbone, the amino acid side chains and the amino- or carboxy-terminus. The same type of modification may be present in the same or varying degrees at several sites in a given polypeptide, and a polypeptide may contain more than one type of modification. Polypeptides may be branched as a result of ubiquitination, and they may be cyclic, with or without branching. Cyclic, branched, and branched cyclic polypeptides may result from posttranslational natural processes or may be made synthetically. Other modifications include pegylation, acetylation, acylation, addition of acetomidomethyl (Acm) group, ADP-ribosylation, alkylation, amidation, biotinylation, carbamoylation, carboxyethylation, esterification, covalent attachment to flavin, covalent attachment to a heme moiety, covalent attachment of a nucleotide or nucleotide derivative, covalent attachment of drug, covalent attachment of a marker (e.g., fluorescent or radioactive), covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination.

A modified polypeptide can also include an amino acid insertion, deletion, or substitution, either conservative or non-conservative (e.g., D-amino acids, desamino acids) in the polypeptide sequence (e.g., where such changes do not substantially alter the biological activity of the polypeptide). In particular, the addition of one or more cysteine residues to the amino or carboxy terminus of any of the polypeptides of the invention can facilitate conjugation of these polypeptides by, e.g., disulfide bonding. For example, Angiopep-1 (SEQ ID NO:67), Angiopep-2 (SEQ ID NO:97), or Angiopep-7 (SEQ ID NO:112) can be modified to include a single cysteine residue at the amino-terminus (SEQ ID NOS: 71, 113, and 115, respectively) or a single cysteine residue at the carboxy-terminus (SEQ ID NOS: 72, 114, and 116, respectively). Amino acid substitutions can be conservative (i.e., wherein a residue is replaced by another of the same general type or group) or non-conservative (i.e., wherein a residue is replaced by an amino acid of another type). In addition, a non-naturally occurring amino acid can be substituted for a naturally occurring amino acid (i.e., non-naturally occurring conservative amino acid substitution or a non-naturally occurring non-conservative amino acid substitution).

Polypeptides made synthetically can include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Analogs may be generated by substitutional mutagenesis and retain the biological activity of the original polypeptide. Examples of substitutions identified as "conservative substitutions" are shown in Table 2. If such substitutions result in a change not desired, then other type of substitutions, denominated "exemplary substitutions" in Table 3, or as further described herein in reference to amino acid classes, are introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile), Histidine (His), Tryptophan (Trp), Tyrosine (Tyr), Phenylalanine (Phe),
(2) neutral hydrophilic: Cysteine (Cys), Serine (Ser), Threonine (Thr)
(3) acidic/negatively charged: Aspartic acid (Asp), Glutamic acid (Glu)
(4) basic: Asparagine (Asn), Glutamine (Gln), Histidine (His), Lysine (Lys), Arginine (Arg)
(5) residues that influence chain orientation: Glycine (Gly), Proline (Pro);
(6) aromatic: Tryptophan (Tip), Tyrosine (Tyr), Phenylalanine (Phe), Histidine (His),
(7) polar: Ser, Thr, Asn, Gln
(8) basic positively charged: Arg, Lys, His, and;
(9) charged: Asp, Glu, Arg, Lys, His Other amino acid substitutions are listed in Table 3.

TABLE 2

Amino acid substitutions

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (I) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

Polypeptide Derivatives and Peptidomimetics

In addition to polypeptides consisting of naturally occurring amino acids, peptidomimetics or polypeptide analogs are also encompassed by the present invention and can form the peptide vectors or peptide therapeutics used in the compounds of the invention. Polypeptide analogs are commonly used in the pharmaceutical industry as non-peptide drugs with properties analogous to those of the template polypeptide. The non-peptide compounds are termed "peptide mimetics" or peptidomimetics (Fauchere et al., *Infect. Immun.* 54:283-287, 1986 and Evans et al., *J. Med. Chem.* 30:1229-1239, 1987). Peptide mimetics that are structurally related to therapeutically useful peptides or polypeptides may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —$CH_2NH$—, —$CH_2S$—, —$CH_2$—$CH_2$—, —CH=CH— (cis and trans), —$CH_2SO$—, —$CH(OH)CH_2$—, —$COCH_2$— etc., by methods well known in the art (Spatola, *Peptide Backbone Modifications, Vega Data*, 1:267, 1983; Spatola et al., *Life Sci.* 38:1243-1249, 1986; Hudson et al., *Int. J. Pept. Res.* 14:177-185, 1979; and Weinstein, 1983, Chemistry and Biochemistry, of Amino Acids, Peptides and Proteins, Weinstein eds, Marcel Dekker, New York). Such polypeptide mimetics may have significant advantages over naturally occurring polypeptides including more economical production, greater chemical stability, enhanced pharmacological properties (e.g., half-life, absorption, potency, efficiency), reduced antigenicity, and others.

While the peptide vectors described herein may efficiently cross the BBB or target particular cell types (e.g., those described herein), their effectiveness may be reduced by the presence of proteases. Likewise, the effectiveness of the polypeptide therapeutics used in the invention may be similarly reduced. Serum proteases have specific substrate requirements, including L-amino acids and peptide bonds for cleavage. Furthermore, exopeptidases, which represent the most prominent component of the protease activity in serum, usually act on the first peptide bond of the polypeptide and require a free N-terminus (Powell et al., *Pharm. Res.* 10:1268-1273, 1993). In light of this, it is often advantageous to use modified versions of polypeptides. The modified polypeptides retain the structural characteristics of the original L-amino acid polypeptides, but advantageously are not readily susceptible to cleavage by protease and/or exopeptidases.

Systematic substitution of one or more amino acids of a consensus sequence with D-amino acid of the same type (e.g., an enantiomer; D-lysine in place of L-lysine) may be used to generate more stable polypeptides. Thus, a polypeptide derivative or peptidomimetic as described herein may be all L-, all D-, or mixed D, L polypeptides. The presence of an N-terminal or C-terminal D-amino acid increases the in vivo stability of a polypeptide because peptidases cannot utilize a D-amino acid as a substrate (Powell et al., *Pharm. Res.* 10:1268-1273, 1993). Reverse-D polypeptides are polypeptides containing D-amino acids, arranged in a reverse sequence relative to a polypeptide containing L-amino acids. Thus, the C-terminal residue of an L-amino acid polypeptide becomes N-terminal for the D-amino acid polypeptide, and so forth. Reverse D-polypeptides retain the same tertiary conformation and therefore the same activity, as the L-amino acid polypeptides, but are more stable to enzymatic degradation in vitro and in vivo, and thus have greater therapeutic efficacy than the original polypeptide (Brady and Dodson, *Nature* 368:692-693, 1994 and Jameson et al., *Nature* 368:744-746, 1994). In addition to reverse-D-polypeptides, constrained polypeptides comprising a consensus sequence or a substantially identical consensus sequence variation may be generated by methods well known in the art (Rizo et al., *Ann. Rev. Biochem.* 61:387-418, 1992). For example, constrained polypeptides may be generated by adding cysteine residues capable of forming disulfide bridges and, thereby, resulting in a cyclic polypeptide. Cyclic polypeptides have no free N- or C-termini Accordingly, they are not susceptible to proteolysis by exopeptidases, although they are, of course, susceptible to endopeptidases, which do not cleave at polypeptide termini. The amino acid sequences of the polypeptides with N-terminal or C-terminal D-amino acids and of the cyclic polypeptides are usually identical to the sequences of the polypeptides to which they correspond, except for the presence of N-terminal or C-terminal D-amino acid residue, or their circular structure, respectively.

A cyclic derivative containing an intramolecular disulfide bond may be prepared by conventional solid phase synthesis while incorporating suitable S-protected cysteine or homocysteine residues at the positions selected for cyclization such as the amino and carboxy termini (Sah et al., *J. Pharm. Pharmacol.* 48:197, 1996). Following completion of the chain assembly, cyclization can be performed either (1) by selective removal of the S-protecting group with a consequent on-support oxidation of the corresponding two free SH-functions, to form a S—S bonds, followed by conventional removal of the product from the support and appropriate purification procedure or (2) by removal of the polypeptide from the support along with complete side chain de-protection, followed by oxidation of the free SH-functions in highly dilute aqueous solution.

The cyclic derivative containing an intramolecular amide bond may be prepared by conventional solid phase synthesis while incorporating suitable amino and carboxyl side chain protected amino acid derivatives, at the position selected for cyclization. The cyclic derivatives containing intramolecular —S-alkyl bonds can be prepared by conventional solid phase chemistry while incorporating an amino acid residue with a suitable amino-protected side chain, and a suitable S-protected cysteine or homocysteine residue at the position selected for cyclization.

Another effective approach to confer resistance to peptidases acting on the N-terminal or C-terminal residues of a polypeptide is to add chemical groups at the polypeptide termini, such that the modified polypeptide is no longer a substrate for the peptidase. One such chemical modification is glycosylation of the polypeptides at either or both termini. Certain chemical modifications, in particular N-terminal glycosylation, have been shown to increase the stability of polypeptides in human serum (Powell et al., *Pharm. Res.* 10:1268-1273, 1993). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified polypeptides consisting of polypeptides bearing an N-terminal acetyl group and/or a C-terminal amide group.

Also included by the present invention are other types of polypeptide derivatives containing additional chemical moieties not normally part of the polypeptide, provided that the derivative retains the desired functional activity of the polypeptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives.

Longer polypeptide sequences which result from the addition of additional amino acid residues to the polypeptides described herein are also encompassed in the present invention. Such longer polypeptide sequences can be expected to have the same biological activity and specificity (e.g., cell tropism) as the polypeptides described above. While polypeptides having a substantial number of additional amino acids are not excluded, it is recognized that some large polypeptides may assume a configuration that masks the effective sequence, thereby preventing binding to a target (e.g., a member of the LRP receptor family such as LRP or LRP2). These derivatives could act as competitive antagonists. Thus, while the present invention encompasses polypeptides or derivatives of the polypeptides described herein having an extension, desirably the extension does not destroy the cell targeting activity of the polypeptides or its derivatives.

Other derivatives included in the present invention are dual polypeptides consisting of two of the same, or two different polypeptides, as described herein, covalently linked to one another either directly or through a spacer, such as by a short stretch of alanine residues or by a putative site for proteolysis (e.g., by cathepsin, see e.g., U.S. Pat. No. 5,126,249 and European Patent No. 495 049). Multimers of the polypeptides described herein consist of a polymer of molecules formed from the same or different polypeptides or derivatives thereof.

The present invention also encompasses polypeptide derivatives that are chimeric or fusion proteins containing a polypeptide described herein, or fragment thereof, linked at its amino- or carboxy-terminal end, or both, to an amino acid sequence of a different protein. Such a chimeric or fusion protein may be produced by recombinant expression of a nucleic acid encoding the protein. For example, a chimeric or fusion protein may contain at least 6 amino acids shared with one of the described polypeptides which desirably results in a chimeric or fusion protein that has an equivalent or greater functional activity.

Assays to Identify Peptidomimetics

As described above, non-peptidyl compounds generated to replicate the backbone geometry and pharmacophore display (peptidomimetics) of the polypeptides described herein often possess attributes of greater metabolic stability, higher potency, longer duration of action, and better bioavailability.

Peptidomimetics compounds can be obtained using any of the numerous approaches in combinatorial library methods known in the art, including biological libraries, spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer, or small molecule libraries of compounds (Lam, *Anticancer Drug Des.* 12:145, 1997). Examples of methods for the synthesis of molecular libraries can be found in the art, for example, in: DeWitt et al. (*Proc. Natl. Acad. Sci. USA* 90:6909, 1993); Erb et al. (*Proc. Natl. Acad. Sci. USA* 91:11422, 1994); Zuckermann et al. (*J. Med. Chem.* 37:2678, 1994); Cho et al. (*Science* 261:1303, 1993); Carell et al. (*Angew. Chem., Int. Ed. Engl.* 33:2059, 1994 and ibid 2061); and in Gallop et al. (*Med. Chem.* 37:1233, 1994). Libraries of compounds may be presented in solution (e.g., Houghten, Biotechniques 13:412-421, 1992) or on beads (Lam, *Nature* 354:82-84, 1991), chips (Fodor, *Nature* 364:555-556, 1993), bacteria or spores (U.S. Pat. No. 5,223,409), plasmids (Cull et al., *Proc. Natl. Acad. Sci. USA* 89:1865-1869, 1992) or on phage (Scott and Smith, *Science* 249:386-390, 1990), or luciferase, and the enzymatic label detected by determination of conversion of an appropriate substrate to product.

Once a polypeptide as described herein is identified, it can be isolated and purified by any number of standard methods including, but not limited to, differential solubility (e.g., precipitation), centrifugation, chromatography (e.g., affinity, ion exchange, and size exclusion), or by any other standard techniques used for the purification of peptides, peptidomimetics, or proteins. The functional properties of an identified polypeptide of interest may be evaluated using any functional assay known in the art. Desirably, assays for evaluating downstream receptor function in intracellular signaling are used (e.g., cell proliferation).

For example, the peptidomimetics compounds of the present invention may be obtained using the following three-phase process: (1) scanning the polypeptides described herein to identify regions of secondary structure necessary for targeting the particular cell types described herein; (2) using conformationally constrained dipeptide surrogates to refine the backbone geometry and provide organic platforms corresponding to these surrogates; and (3) using the best organic platforms to display organic pharmocophores in libraries of candidates designed to mimic the desired activity of the native polypeptide. In more detail the three phases are as follows. In phase 1, the lead candidate polypeptides are scanned and their structure abridged to identify the requirements for their activity. A series of polypeptide analogs of the original are synthesized. In phase 2, the best polypeptide analogs are investigated using the conformationally constrained dipeptide surrogates. Indolizidin-2-one, indolizidin-9-one and quinolizidinone amino acids ($I^2$aa, $I^9$aa and Qaa respectively) are used as platforms for studying backbone geometry of the best peptide candidates. These and related platforms (reviewed in Halab et al., *Biopolymers* 55:101-122, 2000 and Hanessian et al., *Tetrahedron* 53:12789-12854, 1997) may be introduced at specific regions of the polypeptide to orient the pharmacophores in different directions. Biological evaluation of these analogs identifies improved lead polypeptides that mimic the geometric requirements for activity. In phase 3, the platforms from the most active lead polypeptides are used to display organic surrogates of the pharmacophores responsible for activity of the native peptide. The pharmacophores and scaffolds are combined in a parallel synthesis format. Derivation of polypeptides and the above phases can be accomplished by other means using methods known in the art.

Structure function relationships determined from the polypeptides, polypeptide derivatives, peptidomimetics or other small molecules described herein may be used to refine and prepare analogous molecular structures having similar or better properties. Accordingly, the compounds of the present invention also include molecules that share the structure, polarity, charge characteristics and side chain properties of the polypeptides described herein.

In summary, based on the disclosure herein, those skilled in the art can develop peptides and peptidomimetics screening assays which are useful for identifying compounds for targeting an agent to particular cell types (e.g., those described herein). The assays of this invention may be developed for low-throughput, high-throughput, or ultra-high throughput screening formats. Assays of the present invention include assays amenable to automation.

Linkers

The polypeptide therapeutic (e.g., neurotensin) may be bound to the vector peptide either directly (e.g., through a covalent bond such as a peptide bond) or may be bound through a linker. Linkers include chemical linking agents (e.g., cleavable linkers) and peptides.

In some embodiments, the linker is a chemical linking agent. The polypeptide therapeutic and peptide vector may be conjugated through sulfhydryl groups, amino groups (amines), and/or carbohydrates or any appropriate reactive group. Homobifunctional and heterobifunctional cross-linkers (conjugation agents) are available from many commercial sources. Regions available for cross-linking may be found on the polypeptides of the present invention. The cross-linker may comprise a flexible arm, e.g., 2, 3, 4, 5, 6, 7, 8, 9, 10, 11, 12, 13, 14, or 15 carbon atoms. Exemplary cross-linkers include BS3 ([Bis(sulfosuccinimidyl)suberate]; BS3 is a homobifunctional N-hydroxysuccinimide ester that targets accessible primary amines), NHS/EDC(N-hydroxysuccinimide and N-ethyl-'(dimethylaminopropyl) carbodimide; NHS/EDC allows for the conjugation of primary amine groups with carboxyl groups), sulfo-EMCS ([N-e-Maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups).

To form covalent bonds, one can use as a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxysulfosuccinimide (sulfo-NHS), maleimide-benzoyl-succinimide (MBS), gamma-maleimido-butyryloxy succinimide ester (GMBS), maleimido propionic acid (MPA) maleimido hexanoic acid (MHA), and maleimido undecanoic acid (MUA).

Primary amines are the principal targets for NHS esters. Accessible α-amine groups present on the N-termini of proteins and the ε-amine of lysine react with NHS esters. An amide bond is formed when the NHS ester conjugation reaction reacts with primary amines releasing N-hydroxysuccinimide. These succinimide containing reactive groups are herein referred to as succinimidyl groups. In certain embodiments of the invention, the functional group on the protein will be a thiol group and the chemically reactive group will be a maleimido-containing group such as gamma-maleimide-butrylamide (GMBA or MPA). Such maleimide containing groups are referred to herein as maleido groups.

The maleimido group is most selective for sulfhydryl groups on peptides when the pH of the reaction mixture is 6.5-7.4. At pH 7.0, the rate of reaction of maleimido groups with sulfhydryls (e.g., thiol groups on proteins such as serum albumin or IgG) is 1000-fold faster than with amines. Thus, a stable thioether linkage between the maleimido group and the sulfhydryl can be formed.

In other embodiments, the linker includes at least one amino acid (e.g., a peptide of at least 2, 3, 4, 5, 6, 7, 10, 15, 20, 25, 40, or 50 amino acids). In certain embodiments, the linker is a single amino acid (e.g., any naturally occurring amino acid such as Cys). In other embodiments, a glycine-rich peptide such as a peptide having the sequence [Gly-Gly-Gly-Gly-Ser]$_n$ (SEQ ID NO:157) where n is 1, 2, 3, 4, 5 or 6 is used, as described in U.S. Pat. No. 7,271,149. In other embodiments, a serine-rich peptide linker is used, as described in U.S. Pat. No. 5,525,491. Serine rich peptide linkers include those of the formula [X-X-X-X-Gly]$_y$ (SEQ ID NO:158), where up to two of the X are Thr, and the remaining X are Ser, and y is 1 to 5 (e.g., Ser-Ser-Ser-Ser-Gly (SEQ ID NO:159), where y is greater than 1). In some cases, the linker is a single amino acid (e.g., any amino acid, such as Gly or Cys).

Examples of suitable linkers are succinic acid, Lys, Glu, and Asp, or a dipeptide such as Gly-Lys. When the linker is succinic acid, one carboxyl group thereof may form an amide bond with an amino group of the amino acid residue, and the other carboxyl group thereof may, for example, form an amide bond with an amino group of the peptide or substituent. When the linker is Lys, Glu, or Asp, the carboxyl group thereof may form an amide bond with an amino group of the amino acid residue, and the amino group thereof may, for example, form an amide bond with a carboxyl group of the substituent. When Lys is used as the linker, a further linker may be inserted between the ε-amino group of Lys and the substituent. In one particular embodiment, the further linker is succinic acid which, e.g., forms an amide bond with the ε-amino group of Lys and with an amino group present in the substituent. In one embodiment, the further linker is Glu or Asp (e.g., which forms an amide bond with the ε-amino group of Lys and another amide bond with a carboxyl group present in the substituent), that is, the substituent is a $N^\epsilon$-acylated lysine residue.

Neurotensin Agonist Activity Assay

Determination of whether a compound has neurotensin agonist activity can be performed using any method known in the art. Activity at the neurotensin receptor can measured, for example, by release of inositol phosphates. Inositol phosphate production from cells expressing a neurotensin receptor (e.g., a human or rat receptor) can be measured in the presence and in the absence of a compound, where an increase in inositol phosphate production indicates the compound to be a neurotensin receptor agonist.

In one example described in Watson et al., J Neurochem 59:1967-1970, 1992, Chinese hamster ovary (CHO) cells were transformed with the rat neurotensin receptor. Binding of neurotensin agonists can be measured by contacting detectably labeled neurotensin (e.g., labeled with $^3$H), and measuring competition with a test compound. Second messagner synthesis (D-myo-inositol 1-phospate (IP$_1$)) can measured by prelabeling cells with D-myo-[$^3$H]inositol. Production of [$^3$H]Inositol 1-phosphate is isolated by anion exchange chromatorgraphy.

Therapeutic Applications

The compounds of the invention can be used in any appropriate therapeutic application where the activity of neurotensin activity is beneficial. Neurotensin (NT) is a 13 amino acid peptide found in the central nervous system and in the gastrointestinal tract. In brain, NT is associated with dopaminergic receptors and other neurotransmitter systems. Peripheral NT acts as a paracrine and endocrine peptide on both the digestive and cardiovascular systems. Various therapeutic applications have been suggested for neurotensin, including psychiatric disorders, metabolic disorder, and pain. Because neurotensin has been shown to modulate neurotransmission in areas of the brain associated with schizophrenia, neurotensin and neurotensin receptor agonists have been proposed as antipsychotic agents.

Neurological Disease

Because polypeptides described herein are capable of transporting an agent across the BBB, the compounds of the invention are also useful for the treatment of neurological diseases such as neurodegenerative diseases or other conditions of the central nervous system (CNS), the peripheral nervous system, or the autonomous nervous system (e.g., where neurons are lost or deteriorate). Neurotensin has been suggested an antipsychotic therapy, and thus may be useful in the treatment of diseases such as schizophrenia and bipolar disorder. Many neurodegenerative diseases are characterized by ataxia (i.e., uncoordinated muscle movements)

and/or memory loss. Neurodegenerative diseases include Alexander disease, Alper disease, Alzheimer's disease, amyotrophic lateral sclerosis (ALS; i.e., Lou Gehrig's disease), ataxia telangiectasia, Batten disease (Spielmeyer-Vogt-Sjogren-Batten disease), bovine spongiform encephalopathy (BSE), Canavan disease, Cockayne syndrome, corticobasal degeneration, Creutzfeldt-Jakob disease, Huntington's disease, HIV-associated dementia, Kennedy's disease, Krabbé disease, Lewy body dementia, Machado-Joseph disease (Spinocerebellar ataxia type 3), multiple sclerosis, multiple system atrophy, narcolepsy, neuroborreliosis, Parkinson's disease, Pelizaeus-Merzbacher disease, Pick's disease, primary lateral sclerosis, prion diseases, Refsum's disease, Schilder's disease (i.e., adrenoleukodystrophy), schizophrenia, spinocerebellar ataxia, spinal muscular atrophy, Steele-Richardson, Olszewski disease, and tabes dorsalis.

Other neurological and psychiatric diseases that may be treated with the compounds of the invention include Tourette's syndrome and obsessive compulsive disorder.

Inducing Body Temperature Reduction

The compounds of the invention may be used to reduce the body temperature of a subject. Because reduction in body temperature has been shown to be beneficial in subjects who who are in need of neuroprotection, e.g., may be suffering from, or may have recently suffered from, a stroke, cerebral ischemia, cardiac ischemia, or a nerve injury such as a spinal chord injury or head or brain injury (e.g., traumatic brain injury), such a treatment would therefore be useful in reducing complications of these conditions. Reduction of body temperature may also be desired during surgical procedures such as cardiac surgery (e.g., open heart surgery) or other major surgery or where the subject is suffering from malignant hypothermia.

Pain

Neurotensin is also known to have analgesic effects. Thus the compounds of the invention may be used to reduce pain in a subject. The subject may be suffering from an acute pain (e.g., selected from the group consisting of mechanical pain, heat pain, cold pain, ischemic pain, and chemical-induced pain). Other types of pain include peripheral or central neuropathic pain, inflammatory pain, migraine-related pain, headache-related pain, irritable bowel syndrome-related pain, fibromyalgia-related pain, arthritic pain, skeletal pain, joint pain, gastrointestinal pain, muscle pain, angina pain, facial pain, pelvic pain, claudication, postoperative pain, post traumatic pain, tension-type headache, obstetric pain, gynecological pain, or chemotherapy-induced pain.

Metabolic Disorders

There is evidence that neurotensin can be used to treat metabolic disorders; see, e.g., U.S. Patent Application No. 2001/0046956. Thus the compounds of the invention may be used to treat such disorders. The metabolic disorder may be diabetes (e.g., Type I or Type II), obesity, diabetes as a consequence of obesity, hyperglycemia, dyslipidemia, hypertriglyceridemia, syndrome X, insulin resistance, impaired glucose tolerance (IGT), diabetic dyslipidemia, hyperlipidemia, a cardiovascular disease, or hypertension. The subject may be overweight, obese, or bulimic.

Drug Addiction/Abuse

Neurotensin has also been suggested to be able to treat drug addiction or reduce drug abuse in subjects, particularly with psychostimulants. Thus the compounds of the invention may be useful in treating addiction to or abuse of drugs such as amphetamine, methamphetamine, 3,4-methylenedioxymethamphetamine, nicotine, cocaine, methylphenidate, and arecoline. NT may also be used to treat alcohol addiction.

Administration and Dosage

The present invention also features pharmaceutical compositions that contain a therapeutically effective amount of a compound of the invention. The composition can be formulated for use in a variety of drug delivery systems. One or more physiologically acceptable excipients or carriers can also be included in the composition for proper formulation. Suitable formulations for use in the present invention are found in *Remington's Pharmaceutical Sciences*, Mack Publishing Company, Philadelphia, Pa., 17th ed., 1985. For a brief review of methods for drug delivery, see, e.g., Langer (*Science* 249:1527-1533, 1990).

The pharmaceutical compositions are intended for parenteral, intranasal, topical, oral, or local administration, such as by a transdermal means, for prophylactic and/or therapeutic treatment. The pharmaceutical compositions can be administered parenterally (e.g., by intravenous, intramuscular, or subcutaneous injection), or by oral ingestion, or by topical application or intraarticular injection at areas affected by the vascular or cancer condition. Additional routes of administration include intravascular, intra-arterial, intratumor, intraperitoneal, intraventricular, intraepidural, as well as nasal, ophthalmic, intrascleral, intraorbital, rectal, topical, or aerosol inhalation administration. Sustained release administration is also specifically included in the invention, by such means as depot injections or erodible implants or components. Thus, the invention provides compositions for parenteral administration that comprise the above mention agents dissolved or suspended in an acceptable carrier, preferably an aqueous carrier, e.g., water, buffered water, saline, PBS, and the like. The compositions may contain pharmaceutically acceptable auxiliary substances as required to approximate physiological conditions, such as pH adjusting and buffering agents, tonicity adjusting agents, wetting agents, detergents and the like. The invention also provides compositions for oral delivery, which may contain inert ingredients such as binders or fillers for the formulation of a tablet, a capsule, and the like. Furthermore, this invention provides compositions for local administration, which may contain inert ingredients such as solvents or emulsifiers for the formulation of a cream, an ointment, and the like.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

The compositions containing an effective amount can be administered for prophylactic or therapeutic treatments. In prophylactic applications, compositions can be administered to a subject with a clinically determined predisposition or increased susceptibility to a metabolic disorder or neurological disease. Compositions of the invention can be administered to the subject (e.g., a human) in an amount sufficient to delay, reduce, or preferably prevent the onset of clinical disease. In therapeutic applications, compositions are administered to a subject (e.g., a human) already suffering from disease (e.g., a metabolic disorder such as those described herein, or a neurological disease) in an amount sufficient to cure or at least partially arrest the symptoms of the condition and its complications. An amount adequate to accomplish this purpose is defined as a "therapeutically effective amount," an amount of a compound sufficient to substantially improve some symptom associated with a disease or a medical condition. For example, in the treatment of a metabolic disorder (e.g., those described herein), an agent or compound which decreases, prevents, delays, suppresses, or arrests any symptom of the disease or condition would be therapeutically effective. A therapeutically effective amount of an agent or compound is not required to cure a disease or condition but will provide a treatment for a disease or condition such that the onset of the disease or condition is delayed, hindered, or prevented, or the disease or condition symptoms are ameliorated, or the term of the disease or condition is changed or, for example, is less severe or recovery is accelerated in an individual.

Amounts effective for this use may depend on the severity of the disease or condition and the weight and general state of the subject, but generally range from about 0.05 μg to about 1000 μg (e.g., 0.5-100 μg) of an equivalent amount of exendin-4 the agent or agents per dose per subject. Suitable regimes for initial administration and booster administrations are typified by an initial administration followed by repeated doses at one or more hourly, daily, weekly, or monthly intervals by a subsequent administration. The total effective amount of an agent present in the compositions of the invention can be administered to a mammal as a single dose, either as a bolus or by infusion over a relatively short period of time, or can be administered using a fractionated treatment protocol, in which multiple doses are administered over a more prolonged period of time (e.g., a dose every 4-6, 8-12, 14-16, or 18-24 hours, or every 2-4 days, 1-2 weeks, once a month). Alternatively, continuous intravenous infusion sufficient to maintain therapeutically effective concentrations in the blood are contemplated.

The therapeutically effective amount of one or more agents present within the compositions of the invention and used in the methods of this invention applied to mammals (e.g., humans) can be determined by the ordinarily-skilled artisan with consideration of individual differences in age, weight, and the condition of the mammal. Because certain compounds of the invention exhibit an enhanced ability to cross the BBB, the dosage of the compounds of the invention can be lower than (e.g., less than or equal to about 90%, 75%, 50%, 40%, 30%, 20%, 15%, 12%, 10%, 8%, 7%, 6%, 5%, 4%, 3%, 2%, 1%, 0.5%, or 0.1% of) the equivalent dose of required for a therapeutic effect of the unconjugated agonist. The agents of the invention are administered to a subject (e.g. a mammal, such as a human) in an effective amount, which is an amount that produces a desirable result in a treated subject (e.g. reduction in glycemia, reduced weight gain, increased weight loss, and reduced food intake). Therapeutically effective amounts can also be determined empirically by those of skill in the art.

The subject may also receive an agent in the range of about 0.05 to 10,000 μg equivalent dose as compared to neurotensin per dose one or more times per week (e.g., 2, 3, 4, 5, 6, or 7 or more times per week), 0.1 to 2,500 (e.g., 2,000, 1,500, 1,000, 500, 100, 10, 1, 0.5, or 0.1) μg dose per day or week. A subject may also receive an agent of the composition in the range of 0.1 to 3,000 μg per dose once every two or three weeks.

Single or multiple administrations of the compositions of the invention comprising an effective amount can be carried out with dose levels and pattern being selected by the treating physician. The dose and administration schedule can be determined and adjusted based on the severity of the disease or condition in the subject, which may be monitored throughout the course of treatment according to the methods commonly practiced by clinicians or those described herein.

The compounds of the present invention may be used in combination with either conventional methods of treatment or therapy or may be used separately from conventional methods of treatment or therapy.

When the compounds of this invention are administered in combination therapies with other agents, they may be administered sequentially or concurrently to an individual. Alternatively, pharmaceutical compositions according to the present invention may be comprised of a combination of a compound of the present invention in association with a pharmaceutically acceptable excipient, as described herein, and another therapeutic or prophylactic agent known in the art.

EXAMPLE 1

Synthesis of a neurotensin-Angiopep-2 conjugate

An exemplary neurotensin-Angiopep-2 conjugate was synthesized using the scheme described below. As used in these examples, the abbreviation NT refers to the pE-substituted neurotensin peptide described below (i.e., pELYENKPRRPYIL; SEQ ID NO:117).

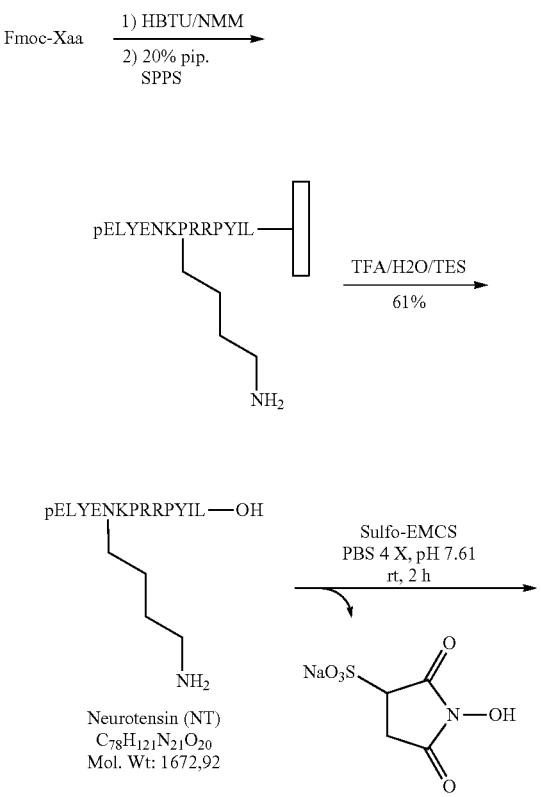

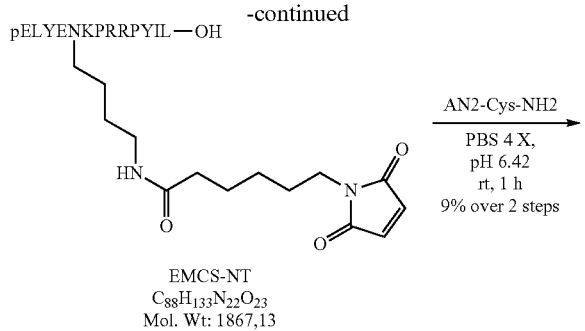

EMCS-NT
C88H133N22O23
Mol. Wt: 1867,13

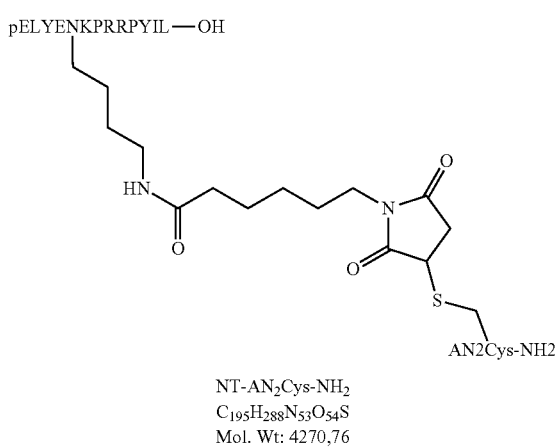

NT-AN2Cys-NH2
C195H288N53O54S
Mol. Wt: 4270,76

Neurotensin Peptide Synthesis pELYENKPRRPYIL-OH (SEQ ID NO:117), where the unusual amino acid L-pyroglutamic acid (pE) is used, was synthesized using SPPS (Solid phase peptide synthesis). SPPS was carried out on a Protein Technologies, Inc. Symphony® peptide synthesizer using Fmoc (9-fluorenyl-methyloxycarbonyl) amino-terminus protection. The peptide was synthesized on a 100 μmol scale using a 5-fold excess of Fmoc-amino acids (200 mM) relative to the resin. Coupling was performed by a pre-loaded Fmoc-Leu-Wang resin (0.48 mmol/g) for carboxyl-terminus acids using 1:1:2 amino acid/activator/NMM in DMF with HBTU (2-(1H-benzotriazol-1-yl)-1,1,3,3-tetramethyluronium hexafluorophosphate) and NMM (N-methylmorpholine). Deprotection was carried out using 20% piperidine/DMF. The resin-bound product was routinely cleaved using a solution comprised of TFA/water/TES: 95/2.5/2.5 for 2 hours at room temperature.

Pre-loaded Fmoc-Leu-Wang resin (0.48 mmol/g) was purchased from ChemPep, Fmoc-amino acids, HBTU from ChemImpex, and the unusual L-pyroglutamic acid from Sigma-Aldrich. Side protecting groups for amino acids were Trt (trityl) for aspargine, tBu (ter-butyl) for glutamic acid and tyrosine, Pbf (pentamethyldihydrobenzofuran-5-sulfonyl) for arginine, and tBoc (tButyloxycarbonyl) for lysine.

The crude peptide was precipitated using ice-cold ether, and purified by RP-HPLC chromatography (Waters Delta Prep 4000). Acetonitrile was evaporated from the collected fractions and lyophilized to give a pure white solid (204 mg, 61%, purity>98%). The mass was confirmed by ESI-TOF MS (Bruker Daltonics; calculated 1672.92, found 1671.90; m/z 558.31 (+3); 836.96 (+2)).

EMCS-NT

Figure 1B:
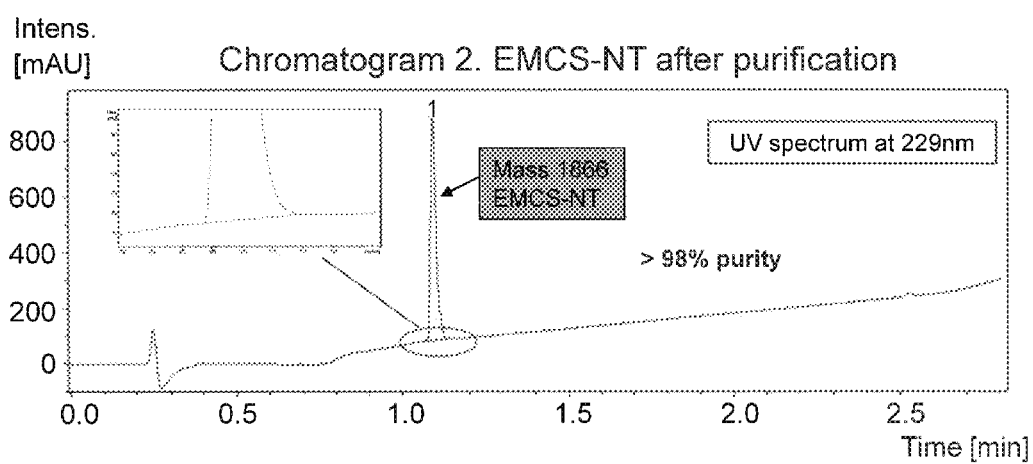
Figure 2:
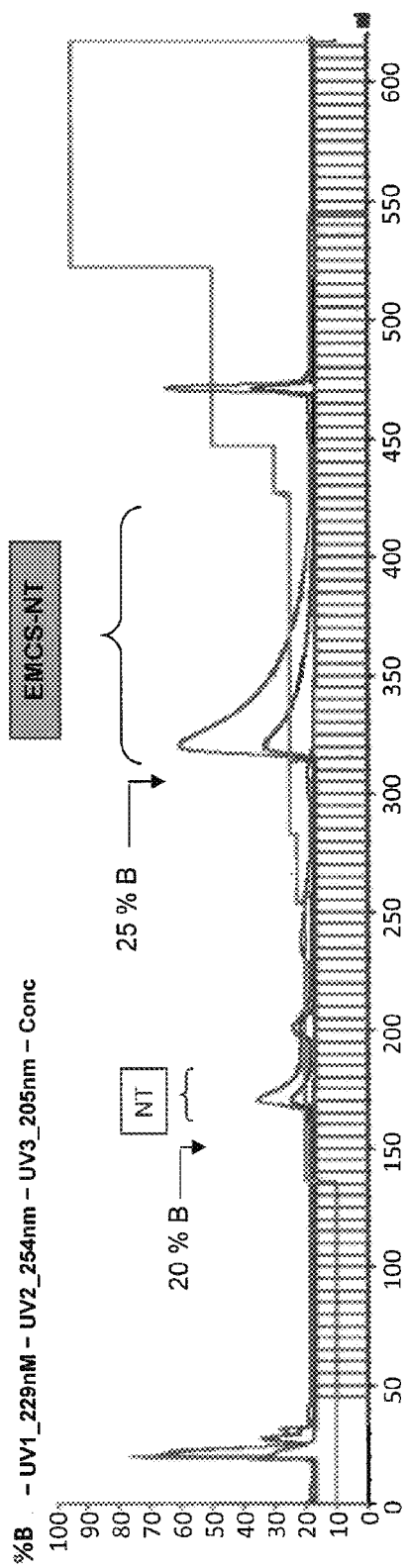
FIG. 2 is a chromatogram showing purification of ECMS-NT on an AKTA-explorer with column filled with 30 ml of 30RPC resin.

The N-lysine primary amine of NT was activated by treating a solution of NT (25 mg, 14.9 μmol, 1 eq. in 3.5 ml of PBS 4×, pH 7.64), with a solution of sulfo-EMCS(N-[ε-maleimidocaproyloxy]sulfosuccinimide ester) (Pierce Biotechnology) (6.1 mg, 14.9 μmol, 1 eq. in 1 ml of PBS 4×). Monitoring of the reaction was done with the analytical method described below (see chromatograms 1-2 in FIGS. 1A and 1B). The reaction (3.32 mM, pH 7.61) allowed proceeding at room temperature for 1 h. The modification was repeated once for 1 h with addition of sulfo-EMCS (4.5 mg, 10.9 μmol, 0.73 eq. in 1 ml of PBS 4×). The mixture was purified by FPLC chromatography (AKTA explorer, see chromatogram 3 in FIG. 2). Purification of EMCS-NT was performed on a column containing 30 RPC resin (polystyrene/divinyl benzene), 30 ml. Sample was loaded as 35 mg in reaction buffer (4 ml), 10% acetonitrile (ACN) in H2O, 0.05% TFA (200 μl). Solution A was H2O, 0.05% TFA, and Solution B was ACN, 0.05 TFA. Flow rate 5-9 ml/min with a gradient of 10-25% of Solution B.

After the acetonitrile was evaporated, the volume of water was reduced to 5 ml for the next step. A colorless solution of the pure EMCS-modified NT (purity>98%) was obtained. The mass was checked by ESI-TOF MS (Bruker Daltonics), was calculated to be 1867.13, and was found to be 1866.00, m/z 623.01 (+3), 934.00 (+2).

NT-AN2Cys-NH2

Figure 3A:
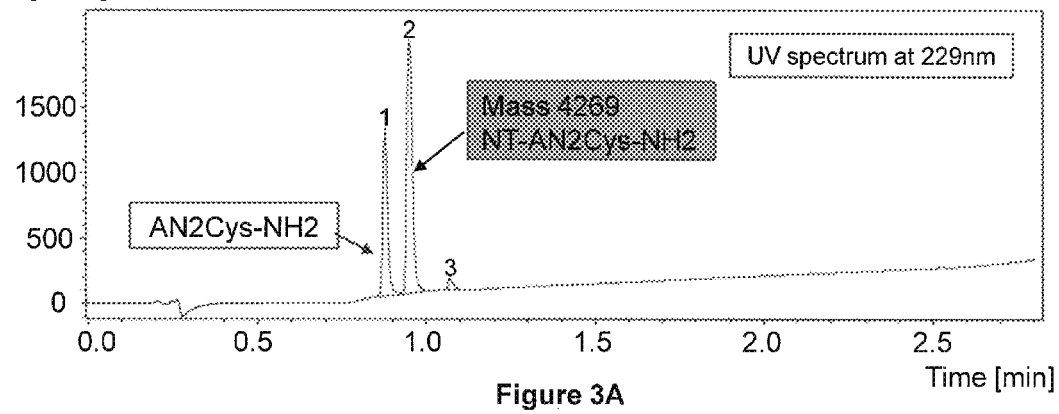
FIGS. 3A and 3B are chromatograms showing a neurotensin-Angiopep-2-Cys amide conjugate (NT-AN2Cys-NH$_2$ or NT-An2) before (FIG. 3A) and after (FIG. 3B) purification. These chromatograms were generated using the analytical method described in the examples.
Figure 3B:
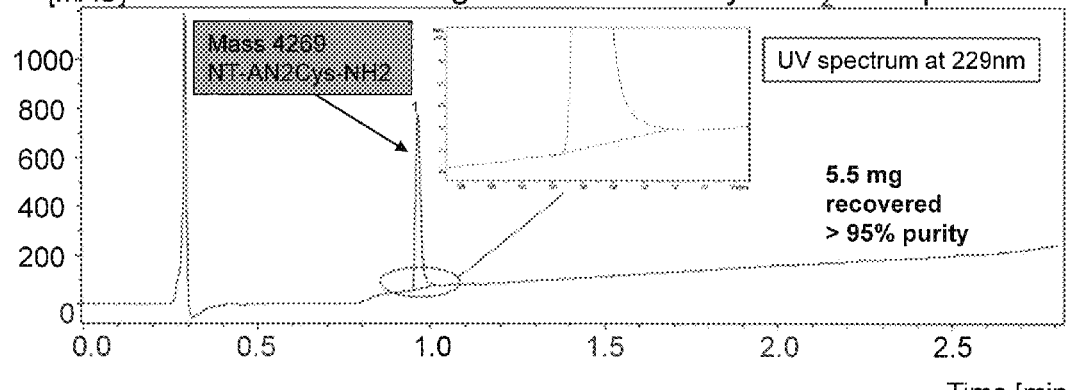
Figure 4:
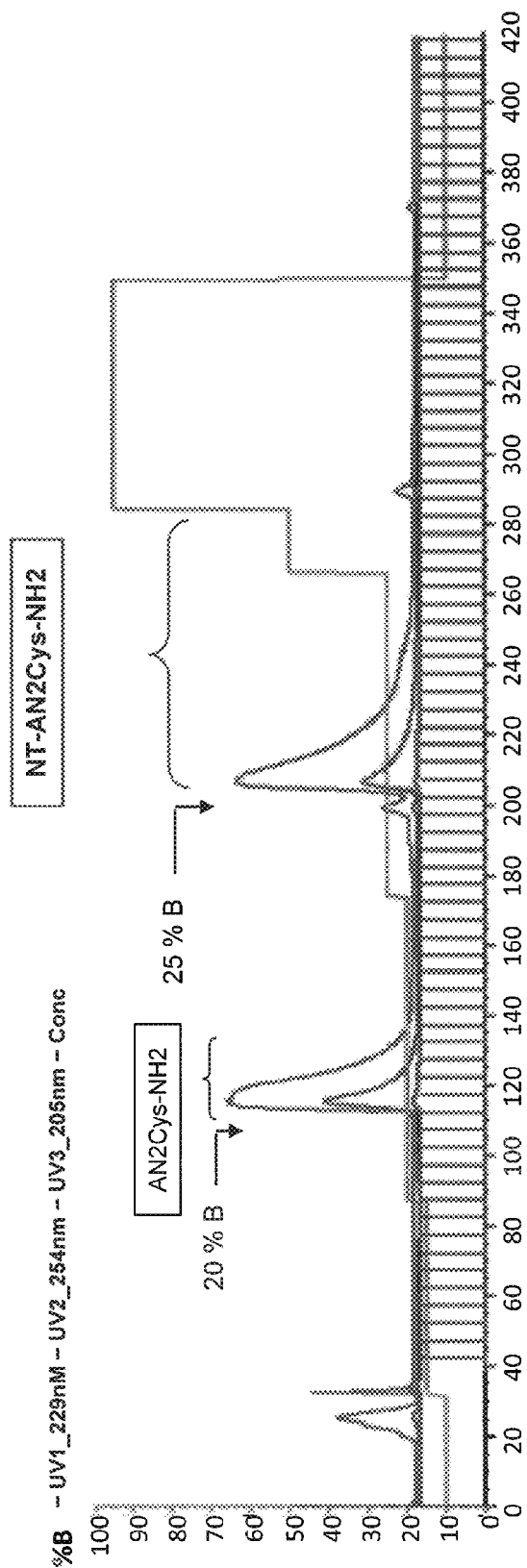
FIG. 4 is a chromatogram showing purification of NT-An2 on an AKTA-explorer with column filled with 30 ml of 30RPC resin.

Conjugation was performed with the maleimido-containing EMCS-NT and the free thiol residue of AN2Cys-NH2. The pH of the solution of EMCS-NT was adjusted from 1.65 to 6.42 by a slow addition of a 0.1N NaOH solution. A hydrolysis side reaction can occur during adjustment of pH (≤5%, hydrolyzed EMCS-NT Mw=1833). A solution of AN2Cys-NH2 (46.4 mg, 14.9 μmol, 1 eq. in 2.5 ml of PBS 4×, pH 7.64) was added to the solution of EMCS-NT. The analytical method below was used to monitoring the reaction (see chromatograms 4-5 in FIGS. 3A and 3B). The reaction (1.9 mM, pH 6.3) was allowed to proceed at room temperature for 30 minutes. The mixture was purified by FPLC chromatography (AKTA explorer, see chromatogram 6 in FIG. 4). Purification of NT-AN2Cys-NH2 was performed using a column (GE Healthcare) containing 30 RPC resin (Polystyrene/divinyl benzene), 30 ml, Sample was loaded in the amount of 74 mg in 4 ml reaction buffer (10% ACN in H2O, 0.05% TFA (200 ul)). Solution A was H2O, 0.05% TFA, and Solution B was ACN, 0.05% TFA. The flow rate was 5-9 ml/min, using a gradient of 10% to 25% of Solution B.

After evaporation of acetonitrile and lyophilization, the conjugated NT-AN2Cys-NH2 was obtained as a pure white solid (5.5 mg, 9% over 2 steps, purity>95%). The mass was confirmed by ESI-TOF MS (Bruker Daltonics); MW was calculated to be 4270.76 and was found to be 4269.17 (m/z 712.54 (+6), 854.84 (+5), 1068.29 (+4), 1424.04 (+3)).

The conjugate was stored under nitrogen atmosphere, below −20° C.

Analytical Method

The following method was used as described above. To analyze samples during purification, a Waters Acquity UPLC system was employed with a BEH phenyl column, 1.7 μm, 2.1×50 mm Detection was performed at 229 nm. Solution A was H2O, 0.1% FA, and Solution B was acetonitrile (ACN), 0.1% FA. Flow rate was 0.5 ml/min with a gradient of 10-90% B, as shown in the table below.

| Time (min) | Flow (mL/min) | % A | % B | Curve |
|---|---|---|---|---|
| | 0.5 | 90 | 10 | |
| 0.40 | 0.5 | 90 | 10 | 6 |
| 0.70 | 0.5 | 70 | 30 | 6 |
| 2.20 | 0.5 | 30 | 70 | 6 |
| 2.40 | 0.5 | 10 | 90 | 6 |
| 2.70 | 0.5 | 10 | 90 | 6 |
| 2.80 | 0.5 | 90 | 10 | 6 |
| 2.81 | 0.5 | 90 | 10 | 6 |

EXAMPLE 2

Characterization of the NT-AN2Cys-NH$_2$ conjugate

Figure 5:
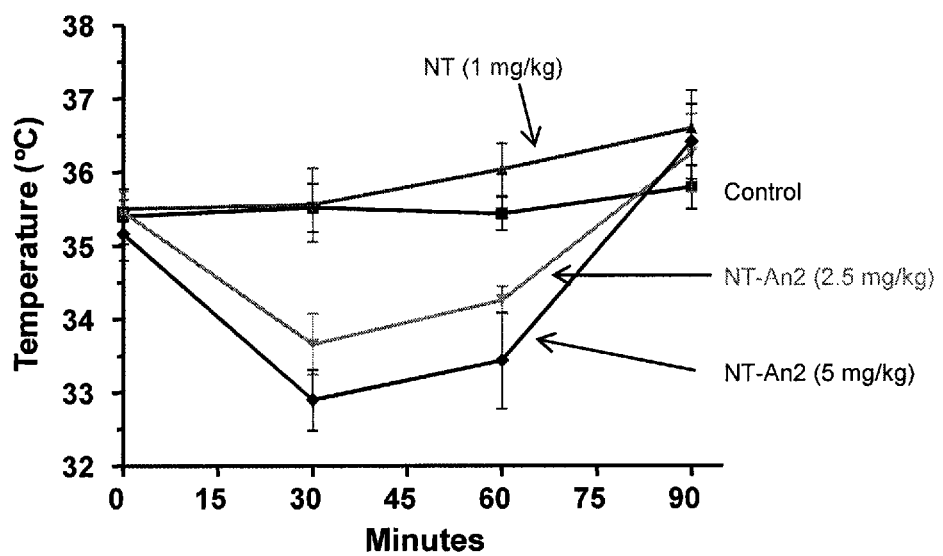
FIG. 5 is a graph showing hypothermia induction by NT-An2. Mice received saline (control), NT (1 mg/kg) or NT-An2 at 2.5 mg/kg or 5.0 mg/kg (equivalent to 1 and 2 mg/kg doses of NT). Rectal temperature was monitored 90 minutes following intravenous injection.

To investigate the pharmacological efficacy and brain penetration of the NT-AN2Cys-NH$_2$ (NT-An2) conjugate, we monitored its effect on the body temperature of mice (FIG. 5). The temperature of mice was unaffected by intravenous administration of 1 mg/kg NT or the saline control. By contrast, intravenous administration of an equivalent dose of the conjugate (2.5 mg/kg) resulted in a rapid decrease in the body temperature, leading to hypothermia. The injection of a higher dose (5 mg/kg) of NT-An2 caused a stronger decrease in body temperature indicating that the effect of NT-An2 is dose dependent.

Figure 6:
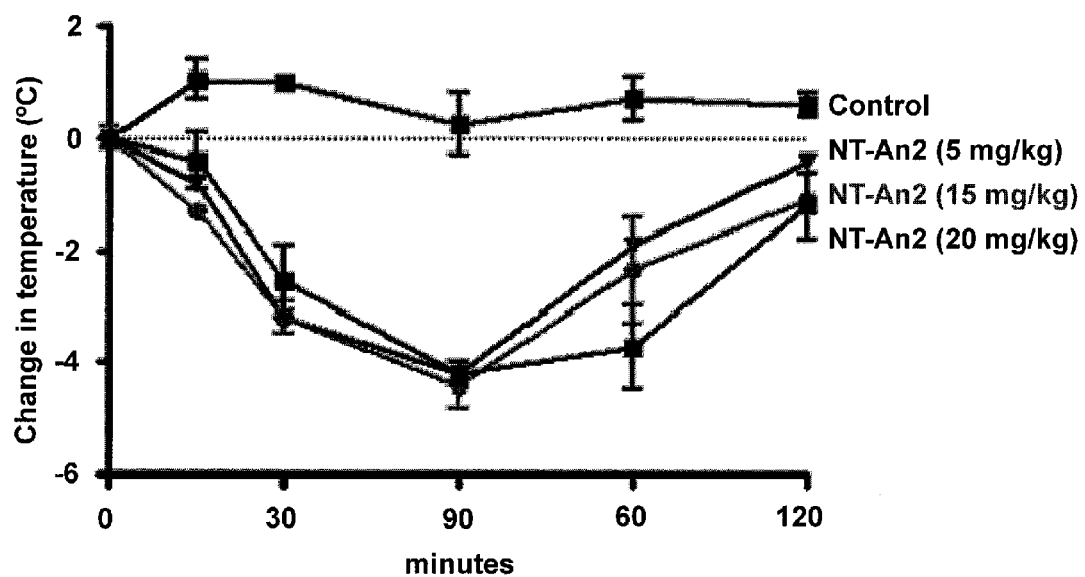
FIG. 6 is a graph showing the effect of body temperature in mice upon administration of 5, 15, or 20 mg/kg of NT-An2.

We also tested whether higher doses of the conjugate would results in greater induction of hypothermia. Mice were administered 5, 15, or 20 mg/kg of the conjugate, and the reduction in body temperature following administration was monitored for 120 minutes following administration. Small differences between these higher doses were observed (FIG. 6).

Figure 7:
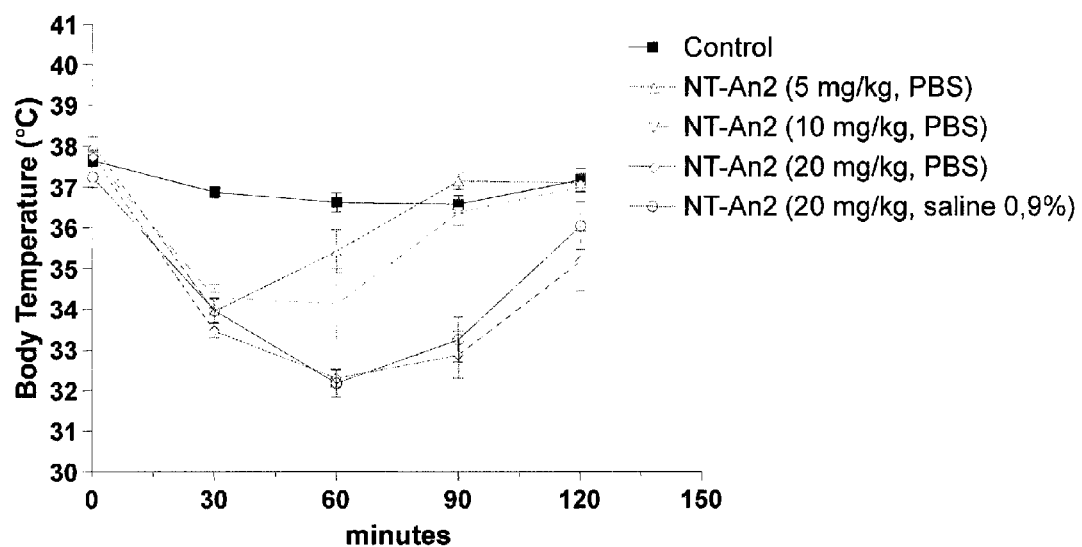
FIG. 7 is a graph showing the effect of body temperature in mice upon administration of 5, 10, or 20 mg/kg of a different preparation of NT-An2.

This experiment was repeated again with a second small batch of the NT-An2 compound, which resulted in similar activity. A third batch, which was produced as a part of an attempt to scale up the production, exhibited similar but somewhat lower activity, as shown in FIG. 7.

Figure 8:
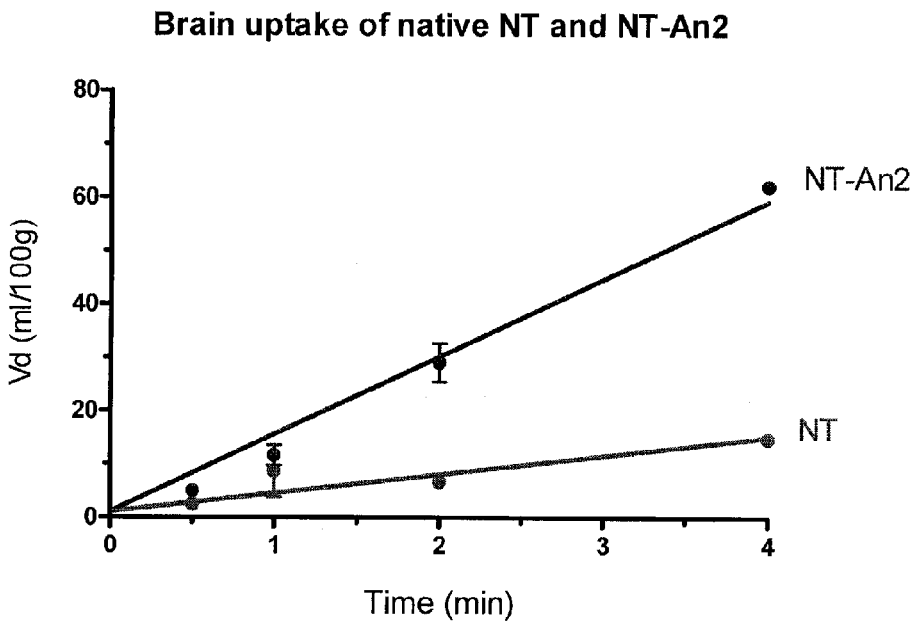
FIG. 8 is a graph showing in situ brain perfusion of NT and NT-An2. Following iodination, mice brains were perfused in the carotid artery with either [$^{125}$I]-NT or the [$^{125}$I]-NT-An2 derivative in Krebs buffer for the indicated times. After the indicated times, brains were further perfused for 30 sec to washout the excess of both compound. Both [$^{125}$I]-NT or [125I]-NT-An2 derivative in brain were quantified using a beta counter. Results are expressed in terms of brain volume of distribution (ml/100 g) as a function of time.
Figure 9:
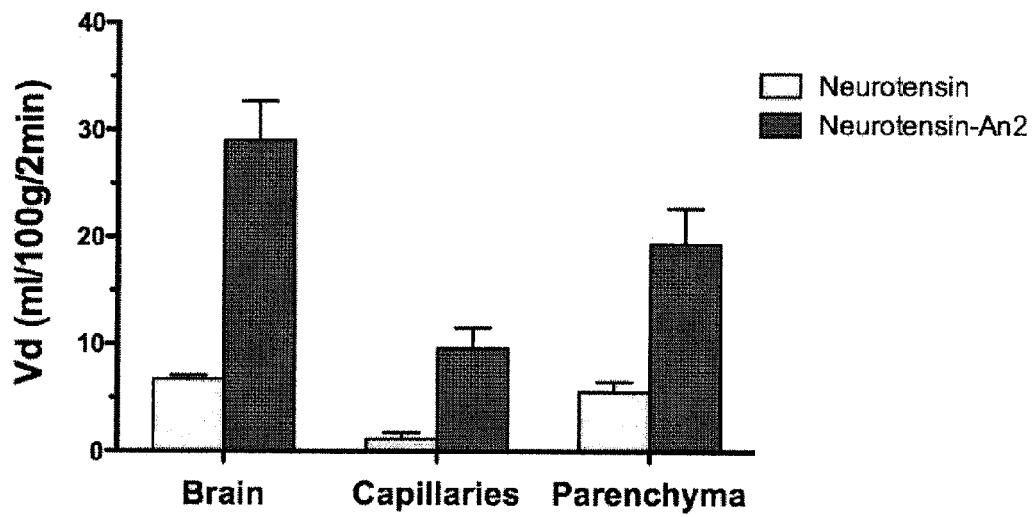
FIG. 9 is a graph showing brain compartmentation of NT and NT-An2 after in situ brain perfusion as described for FIG. 6. Brain capillary depletion was performed using Dextran following standard procedures. Both [$^{125}$I]-NT or [$^{125}$I]NT-An2 derivative present in brain, capillaries, and parenchyma were quantified and volume of distribution (ml/100 g/2 min) is reported.

To confirm that the NT-An2 conjugate crosses the BBB, both NT and the conjugate were iodinated using standard procedures, and in situ brain perfusion was performed using methods standard in the art. The initial transport was measured as a function of time (FIG. 8). Results clearly indicate that the initial brain uptake for the NT-An2 conjugate is higher than for the unconjugated NT. Furthermore, after a 2 min in situ perfusion, capillary depletion was done to quantify the amount of NT-An2 found in the brain parenchyma (FIG. 9). Higher levels of NT-An2 were found in the brain parenchyma when compared to NT. In addition, these results indicate that NT-An2 is not trapped in the brain capillaries. Overall, our results demonstrate that the new NT-An2 derivative crosses the BBB at a sufficient concentration required to activate its receptors involved in the control of the body temperature.

EXAMPLE 3

Induction of Sustained Hypothermia Using Angiopep-NT Conjugates

We performed an additional experiments to test whether the conjugates were able to induce sustained hypothermia in mice and rats.

Figure 10:
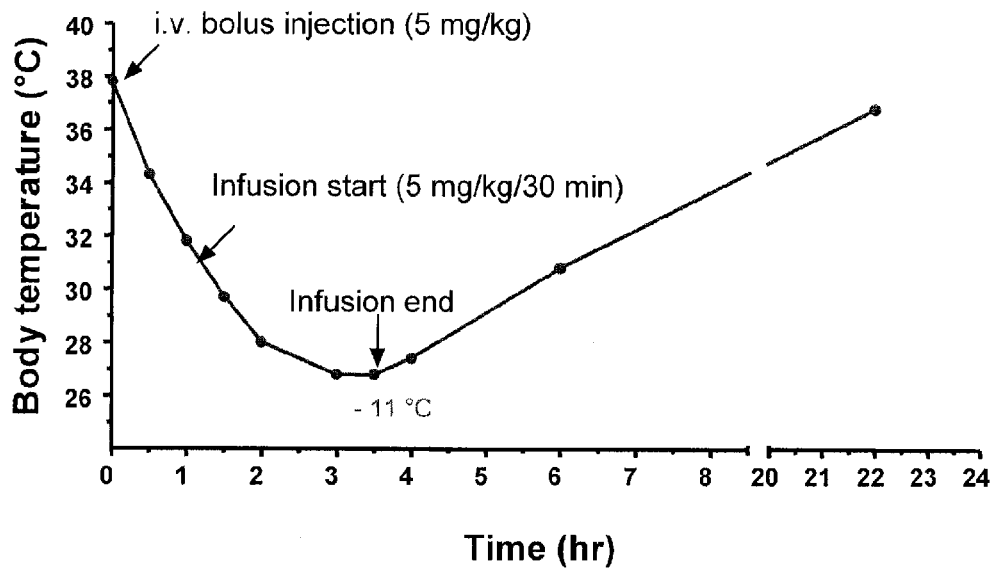
FIG. 10 is a graph showing body temperature of mice receiving a bolus 5 mg/kg injection of the NT-An2, followed one hour later by a 2.5 hour infusion of NT-An2 at a rate of 5 mg/kg/30 min (i.e., 10 mg/kg/hr).

In a first experiment, mice first received an intravenous 5 mg/kg bolus injection of NT-An2, followed by an intravenous infusion (10 mg/kg/hr) 1 hour later for a duration of 2.5 hours. The body temperature continued to decrease during the infusion, reaching a nadir of −11° C. (FIG. 10). After the end of the infusion, body temperature slowly returned to 37° C., and the animals recovered.

Figure 11:
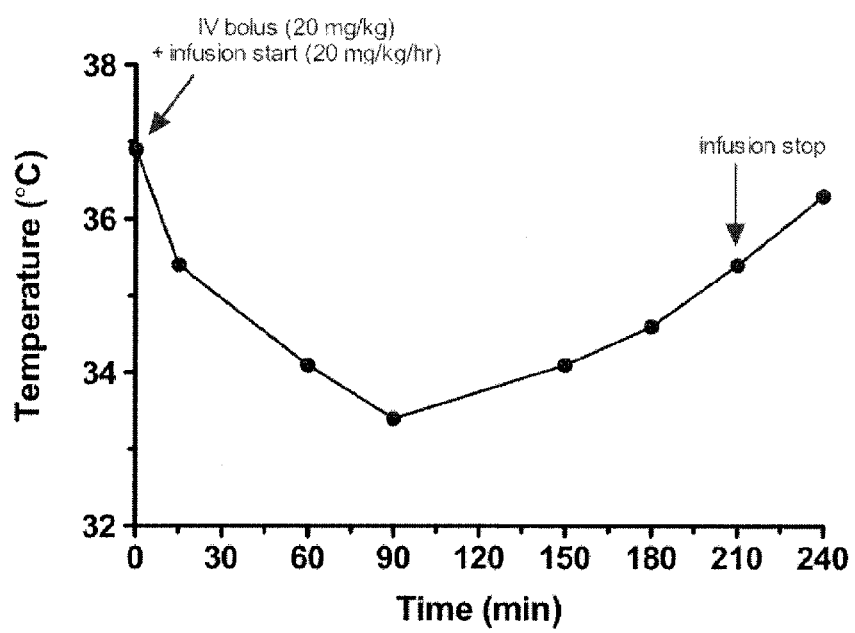
FIG. 11 is a graph showing body temperature of a rat receiving an intravenous bolus injection of 20 mg/kg NT-An2, followed immediately by a 20 mg/kg/hr infusion of NT-An2 for 3.5 hours.

A similar experiment was performed in rats. Here the rats were administered an intravenous bolus injection of 20 mg/kg NT-An2 immediately followed by a 20 mg/kg/hr infusion for 3.5 hours. This resulted in a maximal temperature drop of about 3.5° C. after 90 minutes (FIG. 11).

Figure 12:
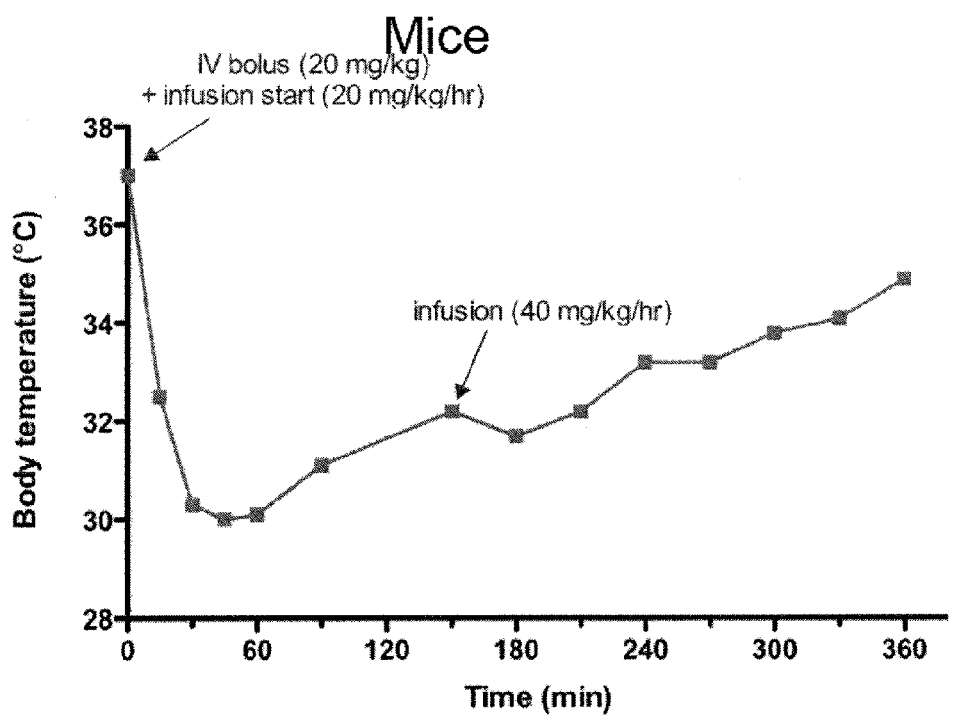
FIG. 12 is a graph showing body temperature of mice receiving an intravenous bolus injection of 20 mg/kg NT-An2, followed immediately by a 20 mg/kg/hr infusion of NT-An2, which was increased to 40 mg/kg/hr after 2.5 hours.

Sustained hypothermia experiments were performed using a intravenous bolus injection of 20 mg/kg of NT-An2 immediately followed by a 20 mg/kg/hr infusion for 2.5 hours. At this time, the infusion was increased to 40 mg/kg/hr. A reduction in body temperature for the initial 37° C. was observed over the 360 minute time course of the experiment (FIG. 12).

Figure 13:
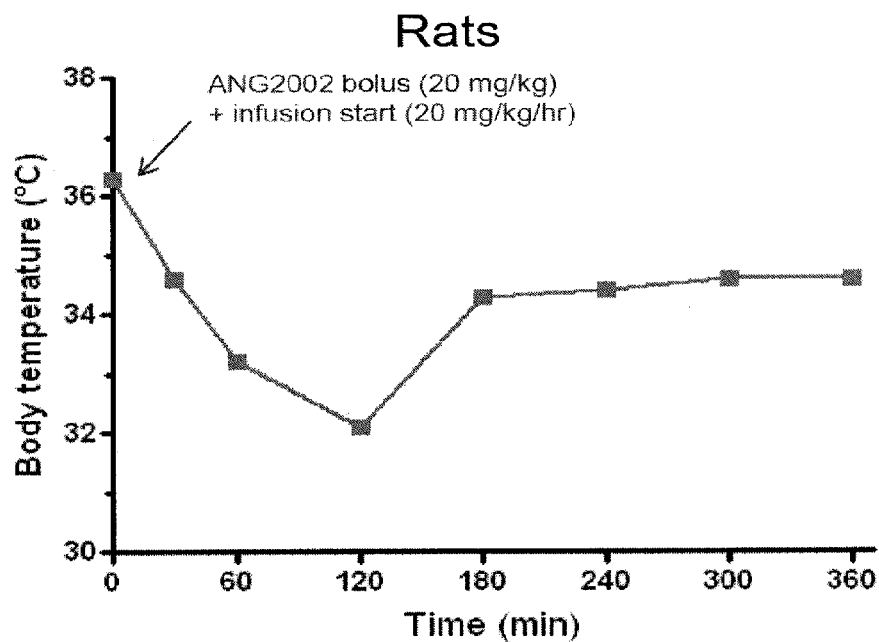
FIG. 13 is a graph showing body temperature of rats receiving an intravenous bolus injection of 20 mg/kg NT-An2, followed immediately by a 20 mg/kg/hr infusion of NT-An2.

A similar experiment was conducted in rats. In this experiment, rats were injected intravenously with 20 mg/kg of NT-An2 immediately followed by a 20 mg/kg/hr infusion. A sustained reduction in body temperature was also observed during the 360-minute time course of this experiment (FIG. 13).

Figure 14:
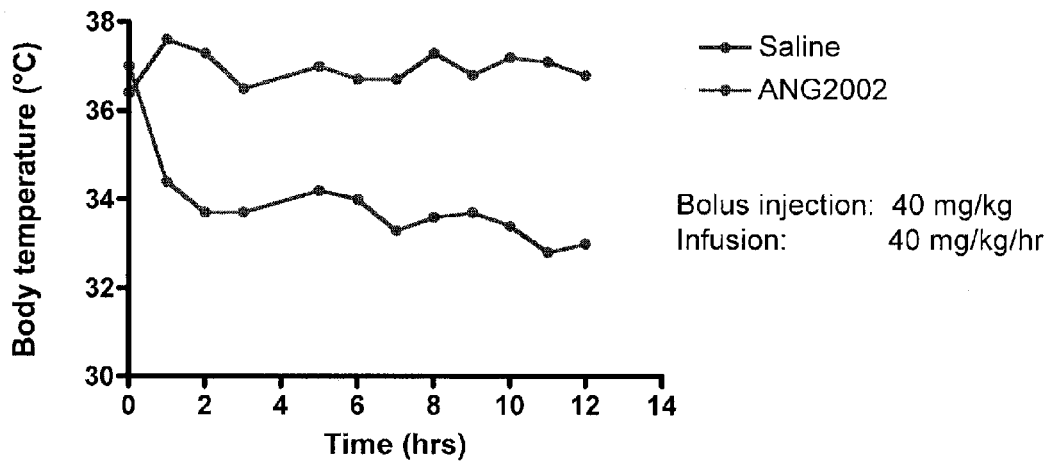
FIG. 14 is a graph showing body temperature of ratings receiving an intravenous bolus injection of 40 mg/kg NT-An2, followed immediately by a 40 mg/kg/hr infusion of NT-An2. This resulted in sustained reduction in body temperature for the 12 hour duration of the experiment.

A further experiment, conducted over a 12-hour period, was also performed in rats. This experiment involved a 40 mg/kg intravenous bolus injection of NT-An2 followed immediately by a 20 mg/kg/hr infusion of NT-An2. As shown in FIG. 14, this resulted in a prolonged reduction of body temperature over the course of the experiment.

EXAMPLE 4

Analgesia Induction by NT-An2

Figure 15:
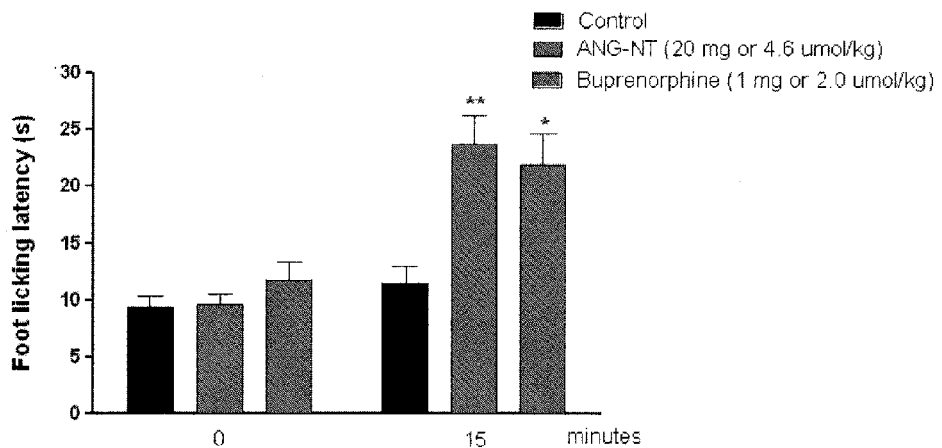
FIG. 15 is a graph showing latency in the hot plate test in mice of the paw licking response in control mice (left), mice receiving 20 mg/kg NT-An2 (center), and mice receiving 1 mg/kg buprenorphine (right) just prior to and 15 minutes following administration of the compound.

We also tested the ability of NT-An2 to induce analgesia in mice. We tested the latency between hot plate foot exposure and foot licking behavior in control mice, mice receiving 20 mg/kg NT-An2, and mice receiving 1 mg/kg of buprenorphine (an opiate analgesic) as a positive control. Both the NT-An2 and the buprenorphine increased the latency of foot licking behavior in a statistically significant manner 15 minutes following injection, thus indicating that NT-An2 can act as an analgesic (FIG. 15).

EXAMPLE 5

Generation of Shorter Neurotensin Analogs

We further generated several shorter neurotensin analogs. These analogs include NT(8-13) (RRPYIL; SEQ ID NO:160), Ac-LysNT(8-13), Ac-Lys-[D-Tyr$^{11}$]NT(8-13), pGlu-LysNT(8-13), MHA-NT(8-13), and β-mercaptoMHA-NT(8-13) (see below).

| Name | Sequence | Mw (g/mol) | Qtty (mg) |
|---|---|---|---|
| NT native | pELYENKPRRPYIL (SEQ ID NO: 117) | 1672.97 | 800, ≥0.95% |
| NT(8-13) | RRPYIL (SEQ ID NO: 160) | 816.99 | 45, ≥95% |
| Ac-LysNT(8-13) | [structure: Ac-NH-CH(RRPYIL)-(CH2)4-NH2] | 987.20 | 78, ≥95% |
| Ac-Lys-[D-Tyr¹¹]NT(8-13) | [structure: Ac-NH-CH(RRPD-YIL)-(CH2)4-NH2] | 987.20 | 55, ≥95% |
| pGlu-LysNT(8-13) | [structure: pGlu-NH-CH(RRPYIL)-(CH2)4-NH2] | 1056.26 | 86, ≥95% |
| MHA-NT(8-13) | [structure: maleimido-hexanoyl-RRPYIL] | 1010.19 | 55, ≥95% |
| β-mercaptoMHA-NT(8-13) (desactive) | [structure: HO-CH2CH2-S-succinimido-hexanoyl-RRPYIL] | 1088.32 | 12, ≥95% |

NT and the NT(8-13) analogs were synthesized by using a SPPS method on a Protein Technologies, Inc. Symphony® peptide synthesizer and Fmoc chemistry. Pre-loaded Fmoc-Leu-Wang resin (0.48 mmol/g) was purchased from ChemPep, Fmoc-amino acids, HBTU from ChemImpex, the unusual pE from Sigma-Aldrich, unnatural D-Tyrosine from ChemImpex, Sulfo-EMCS from Pierce Biotechnology. Side protecting groups for amino acids were Trt for aspargine, tBu for glutamic acid and tyrosine, Pbf for arginine, and tBoc for lysine. Mass was confirmed by ESI-TOF MS (MicroT of, Bruker Daltonics).

General procedure—Synthesis of neurotensin (NT) (pE-LYENKPRRPYIL-OH; SEQ ID NO: 117)). NT was synthesized using the unusual L-pyroglutamic acid (pE) and a 5 fold excess of Fmoc-AA (200 mM) relative to the resin. Coupling was performed from a pre-loaded Fmoc-Leu-Wang resin (0.48 mmol/g) for carboxyl-terminus acids using 1:1:4 AA/HBTU/NMM in DMF. Deprotection was carried out using 20% piperidine/DMF. The resin-bound product was routinely cleaved using a cocktail solution comprised of TFA/water/TES:95/2.5/2.5 for 2 h at room temperature.

The crude peptide was precipitated using ice-cold ether and was purified by RP-HPLC chromatography, Waters Delta Prep 4000, Kromasil 100-10-C18, H₂O/ACN with 0.05% TFA ("Method A"). Acetonitrile was evaporated from the collected fractions and lyophilized. This resulted in the formation of a white and fluffy solid, 800 mg, 80% yield, purity HPLC>98%, calc. 1672.92, found 1671.90; m/z 558.31 (+3); 836.96 (+2).

Synthesis of MHA-NT(8-13) (MHA-RRPYIL-OH; SEQ ID NO: 160). The same procedure was used as for NT. A 100 mM Fmoc-AA solution, and TBTU were used. Prior to cleavage, the N-terminal MHA group was introduced on SPPS by treating the free N-terminal amino peptide bound to the resin with an 18 mM solution of Sulfo-EMCS (1.2 eq. in DMF) for 1.5 h at room temperature. The crude peptide was purified by RP-HPLC chromatography, Waters Delta Prep 4000, Waters BEH Phenyl, H₂O/ACN with 0.05% TFA ("Method B"). This generated 55 mg of product, 73% yield, purity HPLC ≥95%, calc. 1010.19, found 1010.59, m/z 505.81 (+2).

Synthesis of Ac-Lys-[D-Tyr¹¹]NT(8-13) (Ac-KRRPD-YIL-OH). The same procedure was used as for NT. D-Tyrosine, a 100 mM Fmoc-AA solution, and TBTU were used. Before cleavage, a subsequent capping reaction was carried out using a large excess of 1:1:3 v/v/v acetic anhydride/DIEA/DMF for 10 min at room temperature. The peptide was purified by Method A. This resulted in the formation of a white and fluffy solid, 426 mg, 82% yield, purity HPLC≥95%, calc. 987.20, found 987.58; m/z 494.30 (+2).

Synthesis of ANG-Cys-NH2 (H-T¹FFYGG⁶S⁷RGKRNNFKTEEYC-NH2; SEQ ID NO:161). ANG-Cys-NH2 was synthesized using a 5-fold excess of Fmoc-AA (200 mM) relative to the resin. G⁶S⁷ is coupled as the pseudoproline dipeptide GS. Coupling was performed from a Rink amide MBHA resin with Nle (0.40 mmol/g) for carboxyl-terminus amides using 1:1:4 AA/HCTU/NMM in DMF. Cleavage of the resin-bound product was carried out using TFA/water/EDT/TES:94/2.5/2.5/1 for 2 h at room temperature.

The crude peptide was precipitated using ice-cold ether, and purified by RP-HPLC chromatography twice successively, Waters Delta Prep 4000, Kromasil 100-10-C18 and Waters BEH Phenyl, H₂O/ACN with 0.05% TFA ("Method C"). Acetonitrile was evaporated from the collected fractions and lyophilized. This resulted in formation of a white and fluffy solid, 565 mg, 28% yield, purity HPLC>90%, calc. 2403.63, found 2402.05; m/z 1202.53 (+2); 802.04 (+3); 601.78 (+4).

General procedure—Synthesis of MHA-NT NT (1 eq.) was dissolved in PBS 4×(pH 7.3), and the solution pH was adjusted to 7.1 by addition of NaOH 0.1 N solution. To this solution was added a solution of Sulfo-EMCS (1 eq. in PBS 4×). Monitoring of the reaction was done with an analytical method. The reaction (9.0 mM, pH 7.1) allowed proceeding at RT for 2 h. The pH of reaction was adjusted from 5.2 to 7 with addition of NaOH 0.1 N solution.

After a second addition of sulfo-EMCS (0.3 eq. in PBS 4×), the reaction was repeated for 1 h. The mixture was purified by FPLC chromatography, AKTA explorer, 30RPC resin, H₂O/ACN without acid ("Method D"). Before evaporation, the resulting pure pooled fractions were acidified to pH 4 with a solution of water, 0.1% TFA.

After acetonitrile was evaporated, the volume of water was reduced to a minimum volume to be engaged directly in the subsequent conjugation step. This resulted in a colorless solution, estimated to be 278 mg, 83% yield, purity HPLC>98%, calc. 1867.13, found 1866.00; m/z 623.01 (+3); 934.00 (+2).

Synthesis of AcLys(MHA)NT(8-13)(D-Tyr11). The same procedure as MHA-NT from AcLysNT(8-13)(D-Tyr11).

After the first addition of the solution of Sulfo-EMCS (1 eq. in PBS 4×), the reaction (5.0 mM, pH 6.8) allowed proceeding at room temperature for 2 h. This produced a colorless solution, estimated to be 24 mg, 67% yield, purity HPLC≥95, calc. 1180.40, found 1180.64; m/z 590.83 (+2).

The following abbreviations are used in the description of the above synthetic methods.

AA Amino acid
Ac Acetyl group
ANG Angiopep-2
DIEA Diisopropylethylamine
DMF Dimethylformamide
DMSO Dimethylsulfoxide
Fmoc 9-Fluorenylmethyloxycarbonyl
HBTU 2-(1H-Benzotriazol-1-yl)-1,1,3,3-TetramethylUronium Hexafluorophosphate
HCTU 2-(1H-6-Chlorobenzotriazol-1-yl)-1,1,3,3-TetramethylUronium Hexafluorophosphate
MBHA 4-Methylbenzhydrylamine
MHA Maleimidohexanoic acyl group
NMM N-MethylMorpholine
NT Neurotensin
Pbf Pentamethyldihydrobenzofuran-5-sulfonyl
pE L-pyroglutamic acid
SPPS Solid Phase Peptide Synthesis
Sulfo-EMCS N-[ϵ-maleimidocaproyloxy]sulfosuccinimide ester
tBoc tButyloxycarbonyl
TBTU 2-(1H-Benzotriazol-1-yl)-1,1,3,3-TetramethylUronium Tetrafluoroborate
tBu ter-butyl group
TES Triethylsilane
TFA Trifluoroacetic acid
Trt Trityl group

EXAMPLE 6

Characterization of Neurotensin Analogs

Figure 16:
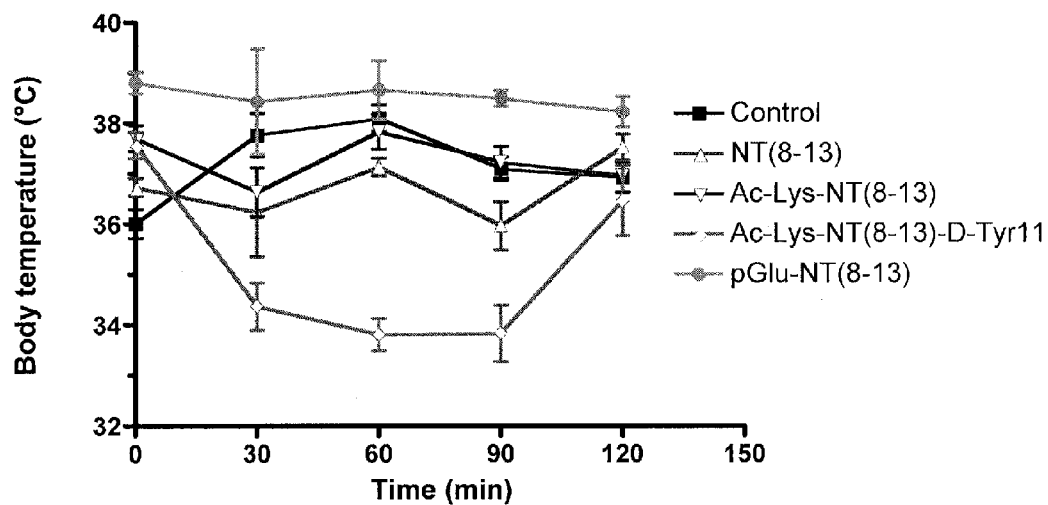
FIG. 16 is a graph showing body temperature of mice receiving a bolus intravenous 7.5 mg/kg injection of NT(8-13), Ac-Lys-NT(8-13), Ac-Lys-[D-Tyr$^{11}$]NT(8-13), pGlu-NT(8-13), or a control. From among these analogs, Ac-Lys-[D-Tyr$^{11}$]NT(8-13) was observed to produce the greatest reduction in body temperature.

To determine which NT analog or analogs would be best suited for conjugation to Angiopep-2, we evaluated the ability of each analog to induce hypothermia in mice. Bolus intravenous injections of 7.5 mg/kg of NT(8-13), Ac-Lys-NT(8-13), Ac-Lys-[D-Tyr¹¹]NT(8-13), pGlu-NT(8-13), and a control were performed (FIG. 16) and body temperature was measured over a period of 120 minutes. Ac-Lys-[D-Tyr¹¹]NT(8-13) exhibited the greatest reduction in body temperature of the analogs tested. This analog was therefore selected for conjugation and further experimentation.

EXAMPLE 7

Generation of Neurotensin Analog Conjugates

Three neurotensin and NT analog conjugates were generated, NT-AN2 (as described above), NT(8-13)-AN², and Ac-Lys-[D-Tyr¹¹]NT(8-13)-AN2. The structure of each of these conjugates is shown in the table below.

| Name | Sequence | Mw (g/mol) | Qtty (mg) |
|---|---|---|---|
| NT-An2 | pELYENKPRRPYIL 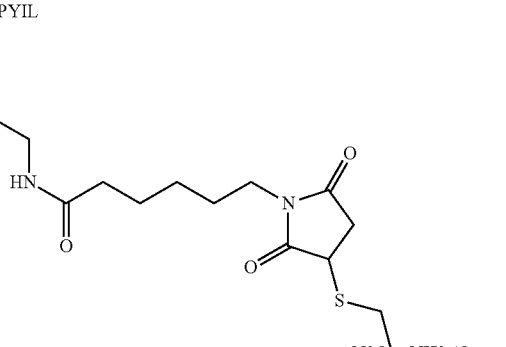 AN2Cys-NH2 (C-term) | 4270.76 | 18, ≥95% |
| NT(8-13)-AN2 | 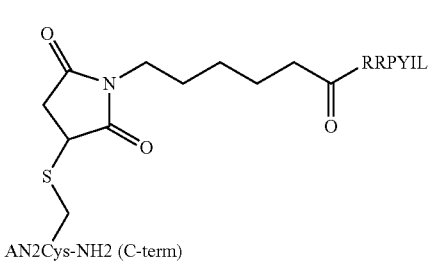 RRPYIL AN2Cys-NH2 (C-term) | 3413.82 | 59, ≥95% |
| Ac-Lys-[D-Tyr¹¹]NT(8-13)-AN2 | 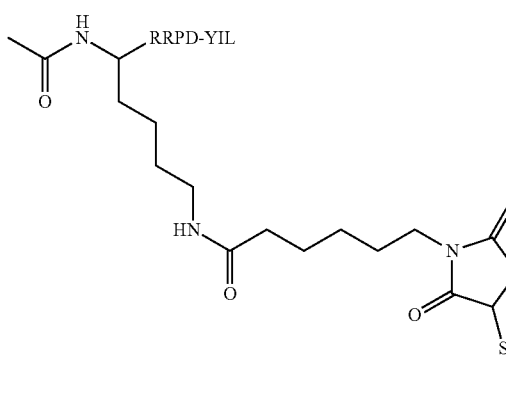 RRPD-YIL AN2Cys-NH2 (C-term) | 3584.03 | 17, ≥95% |

The conjugates analogs were synthesized by using a SPPS method on a Protein Technologies, Inc. Symphony® peptide synthesizer and Fmoc chemistry. Pre-loaded Fmoc-Leu-Wang resin (0.48 mmol/g) was purchased from ChemPep, Fmoc-amino acids, HBTU from ChemImpex, the unusual pE from Sigma-Aldrich, unnatural D-Tyrosine from ChemImpex, Sulfo-EMCS from Pierce Biotechnology. Side protecting groups for amino acids were Trt for aspargine, tBu for glutamic acid and tyrosine, Pbf for arginine, and tBoc for lysine. Mass was confirmed by ESI-TOF MS (MicroT of, Bruker Daltonics). All abbreviations used in the following methods are defined in Example 5 above.

General procedure—Synthesis of ANG-NT. Conjugation was performed with the maleimido-containing MHA-NT and the free thiol residue of ANG-Cys-NH2.

The pH of the previously prepared solution of MHA-NT was adjusted from 4.2 to 5 by slow addition of a 0.1N NaOH solution. To this solution of MHA-NT was added a solution of ANG-Cys-NH$_2$ (1 eq. in PBS 4×, pH 7.3). Monitoring of the reaction was done with an analytical method. The reaction (2.5 mM, pH 5.1) was allowed to proceed at room temperature for 1 h. The mixture was purified by FPLC chromatography, AKTA explorer, 30RPC resin, H$_2$O/ACN with 0.05 TFA ("Method E").

After evaporation of acetonitrile and lyophilization, the conjugated ANG-NT was obtained as a pure white solid, 412 mg, 65% yield, 54% over 2 steps, purity HPLC>95%, calc. 4270.76, found 4269.17; m/z 712.54 (+6); 854.84 (+5); 1068.29 (+4); 1424.04 (+3).

Synthesis of ANG-NT(8-13). The same procedure as ANG-NT was used for MHA-NT(8-13). MHA-NT(8-13) (1 eq.) was dissolved in DMSO (19 mM). The mixture was purified by Method B (see above). This resulted in a white and fluffy solid, 597 mg, 88% yield, purity HPLC≥95%, calc. 3413.82, found 3413.46; m/z 683.75 (+5); 854.19 (+4); 1138.91 (+3).

Synthesis of ANG-AcLys-[D-Tyr¹¹]NT(8-13). The same procedure as ANG-NT was used for AcLys(MHA)-[D-Tyr¹¹]NT(8-13). The peptide was purified by Method E. This resuled in a white solid, 17 mg, 24% yield, purity HPLC≥95%, calc. 3584.03, found 3583.79; m/z 598.30 (+6); 717.76 (+5); 896.70 (+4); 1195 (+3).

EXAMPLE 8

Characterization of Nt Analog Conjugates

Figure 17:
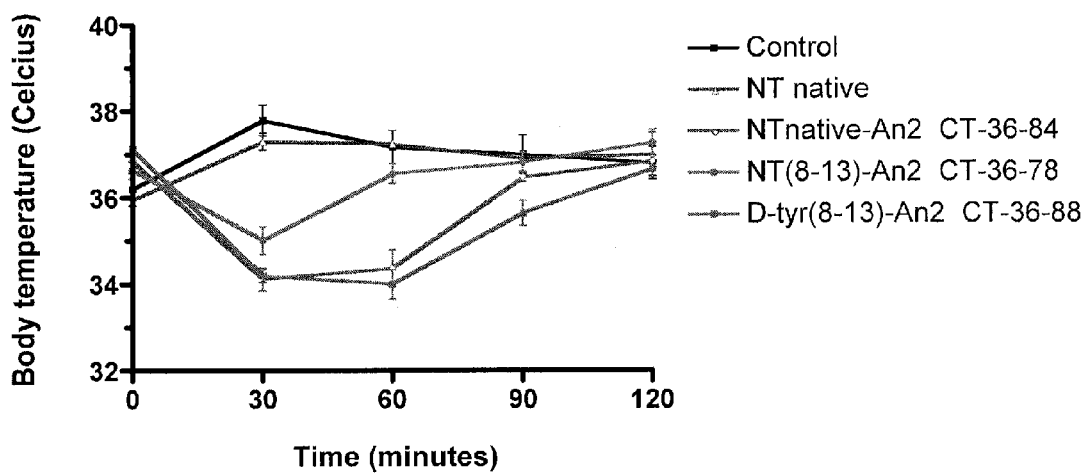
FIG. 17 is a graph showing body temperature of mice receiving a bolus intravenous injection of a control, NT, NT-An2, NT(8-13)-An2, and Ac-Lys[D-Tyr$^{11}$]NT(8-13)-An2. The greatest reduction in body temperature was observed for NT-An2 and Ac-Lys-[D-Tyr$^{11}$]NT(8-13)-An2 conjugates.

To determine the ability of the NT analog conjugates to induce hypothermia, a bolus of a control, unconjugated NT, NT-An2, NT(8-13)-An2, and Ac-Lys-[D-Tyr$^{11}$]NT(8-13)-An2 were each injected intravenously into mice, and body temperature was monitored over a period of 120 minutes. Little difference between the control and the unconjugated NT, some effect was observed with the NT(8-13)-An2 conjugate, and a larger effect was observed with both the NT-An2 and Ac-Lys[D-Tyr$^{11}$]NT(8-13)-An2 conjugates (FIG. 17).

Figure 18:
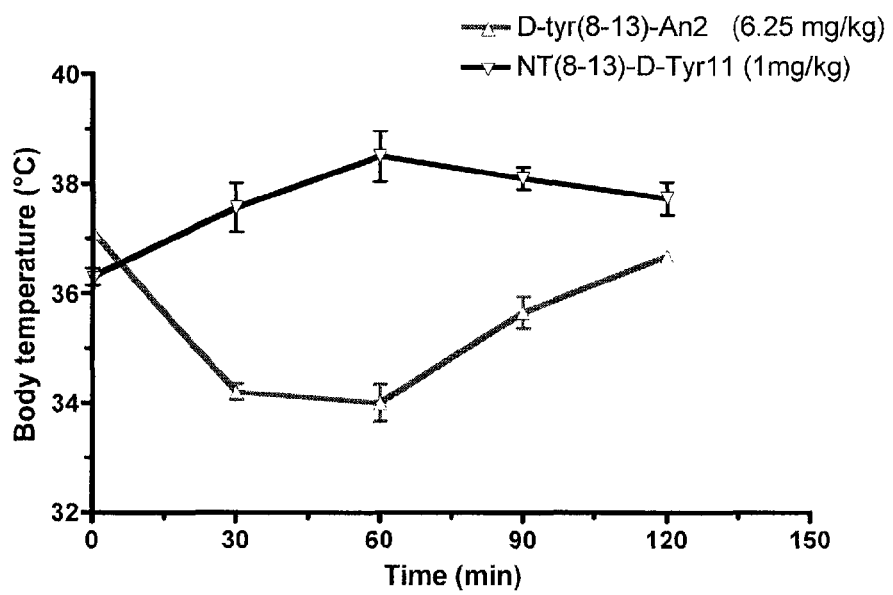
FIG. 18 is a graph showing body temperature of mice receiving a bolus intravenous injection of Ac-Lys-[D-Tyr$^{11}$]NT(8-13) (1 mg/kg) or Ac-Lys[D-Tyr$^{11}$]NT(8-13)-An2 (6.25 mg/kg). The An2 conjugated molecule was observed to reduce body temperature to a greater extent that the unconjugated molecule.

We also compared the ability of unconjugated Ac-Lys[D-Tyr$^{11}$]NT(8-13) at 1 mg/kg to the Ac-Lys-[D-Tyr$^{11}$]NT(8-13)-An2 conjugate at 6.25 mg/kg to reduce body temperature. From these experiments, it was observed that the conjugate reduced body temperature to a greater extent than the unconjugated compound (FIG. 18).

Figure 19:
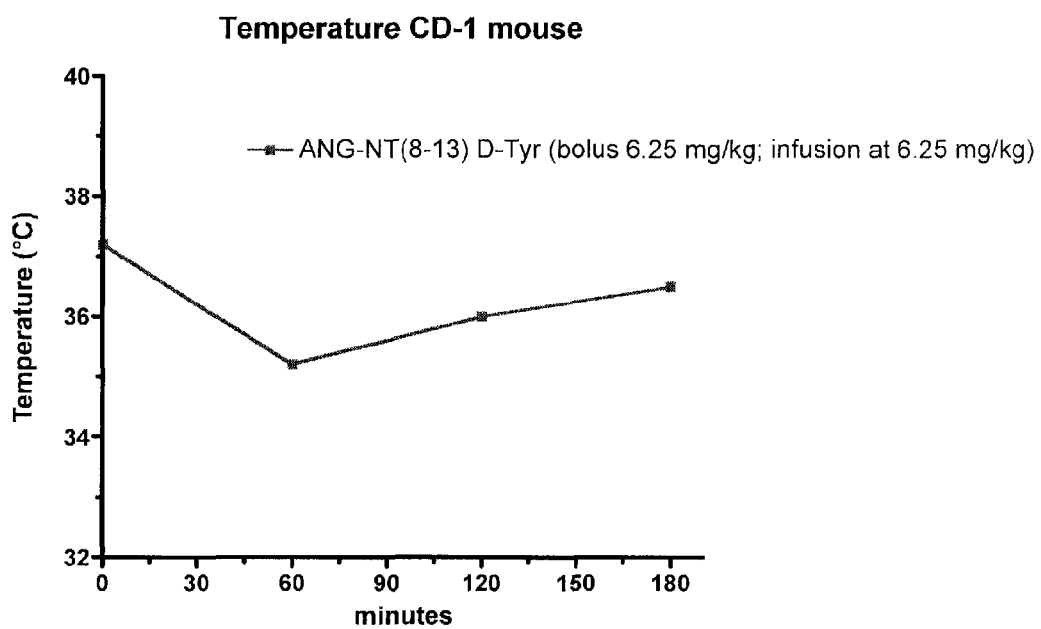
FIG. 19 is a graph showing body temperature of a mouse receiving a 6.25 mg/kg bolus intravenous injection of the Ac-Lys-[D-Tyr$^{11}$]NT(8-13)-An2 conjugate followed 60 minutes later by a 6.25 mg/kg/hr infusion of the conjugate.

A bolus injection (6.25 mg/kg) of the Ac-Lys-[D-Tyr$^{11}$]NT(8-13)-An2 conjugate followed by a 6.25 mg/kg/hr infusion of this conjugate after one hour was also performed (FIG. 19).

EXAMPLE 9

Binding of NT and NT Analogs and Conjugates Thereof to the NT Receptor NTSR1

Figure 20:
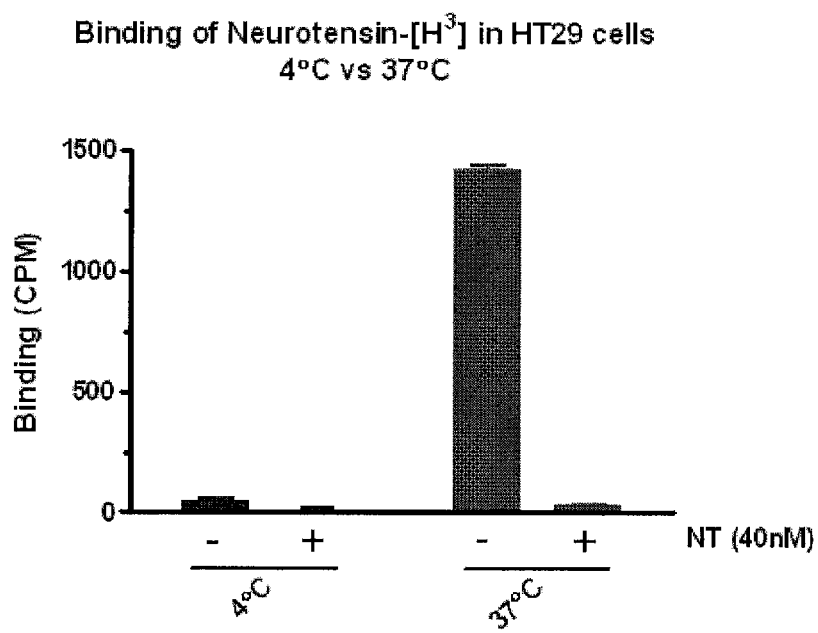
FIG. 20 is a graph showing binding of radiolabeled NT ([$^3$H]-NT) to HT29 cells that express the NTSR1 in the presence or absence of 40 nM of NT at 4° C. or 37° C.
Figure 21:
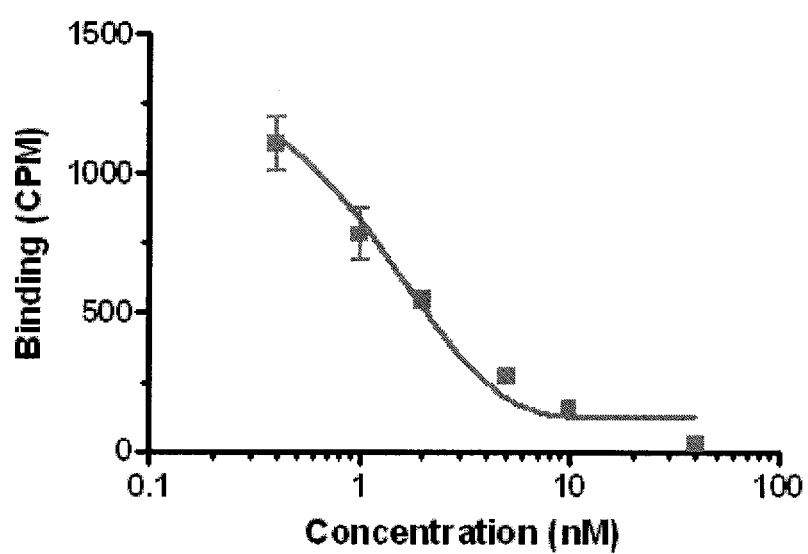
FIG. 21 is a graph showing binding of [$^3$H]-NT to HT29 cells in the presence of NT at concentrations ranging from 0.4 nM to 40 nM.

To further characterize NT, the NT analogs, and conjugates of NT, or NT analogs, a competitive binding assay using HT29 cells (human colon adenocarcinoma grade II cell line) that express the high affinity NTSR1 receptor was employed. As an initial test, we were able to demonstrate that [$^3$H]-neurotensin could be completely displaced from the cells by 40 nM of unlabeled NT (FIG. 20). We then performed a dose response test between 0.4 nM and 40 nM. From these results, we determined that NT has an IC$_{50}$ of 1.4 nM in this system (FIG. 21).

Figure 22:
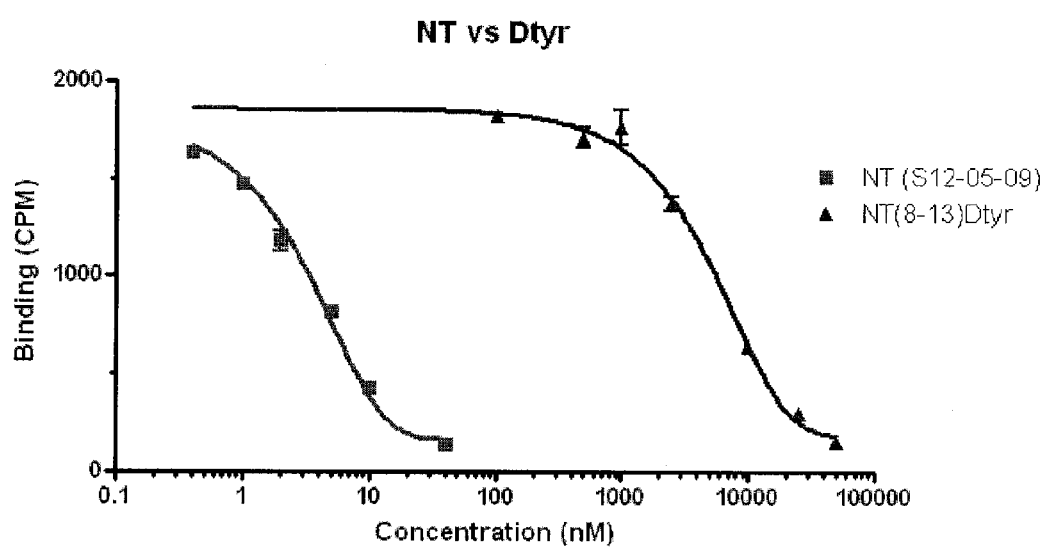
FIG. 22 is graph showing binding of [$^3$H]-NT to HT29 cells in the presence of NT or Ac-Lys-[D-Tyr$^{11}$]NT(8-13).

We then compared the binding of NT to that of Ac-Lys[D-Tyr$^{11}$]NT(8-13)-An2. From this experiment, the binding of this analog was observed to be over 1000-fold weaker than the native NT (IC$_{50}$ of 3.5 nM vs. 5389 nM, as shown in FIG. 22).

Using these methods, we compared both the binding and the induced body temperature reduction between neurotensin, NT analogs, and the conjugates. These results are presented in the table below. The different results for NT and ANG-NT (i.e., NT-An2) represent results from different production batches of each compound.

| Molecules | IC50 (nM) | Δ Max temp (° C.) | Sustained hypothermia |
|---|---|---|---|
| NT | | | |
| prep #1 | 1.6 | 0 | n.d. |
| prep #2 | 1.2-3.5 | 0 | n.d. |
| BACHEM | 4.0 | 0 | n.d. |
| Phoenix Pharmaceutials | 3.1 | 0 | n.d. |
| NT analogs | | | |
| NT(8-13) | <1 | 0 | n.d. |
| AcLysNT(8-13)D-tyr11 | 5389 | −3 (at high dose) | n.d. |
| AcLys-NT(8-13) | 1 | 0 | n.d. |
| pGlu-Lys-NT(8-13) | 1.3 | 0 | n.d. |
| β-mercapto-MHA-NT (8-13) | 5 | 0 | n.d. |
| ANG-NT conjugates | | | |
| ANG-NT (prep #1) | n.a. | −4 to −5 | n.a. |
| ANG-NT (prep #2) | 23.5 (glass) | −4 to −5 | +++ |
| ANG-NT (prep #3) | 10 | −3 to −4 | + |
| ANG-NT (prep #4) | 6.8 | −2 to −4 | − |
| ANG-NT(8-13) | 4 | 0 | n.d. |
| ANG-NT(8-13)(D-Tyr) | >100 | −3 to −4 | + |

Other Embodiments

All patents, patent applications, and publications mentioned in this specification are herein incorporated by reference to the same extent as if each independent patent, patent application, or publication was specifically and individually indicated to be incorporated by reference.

What is claimed is:

1. A compound having the structure:

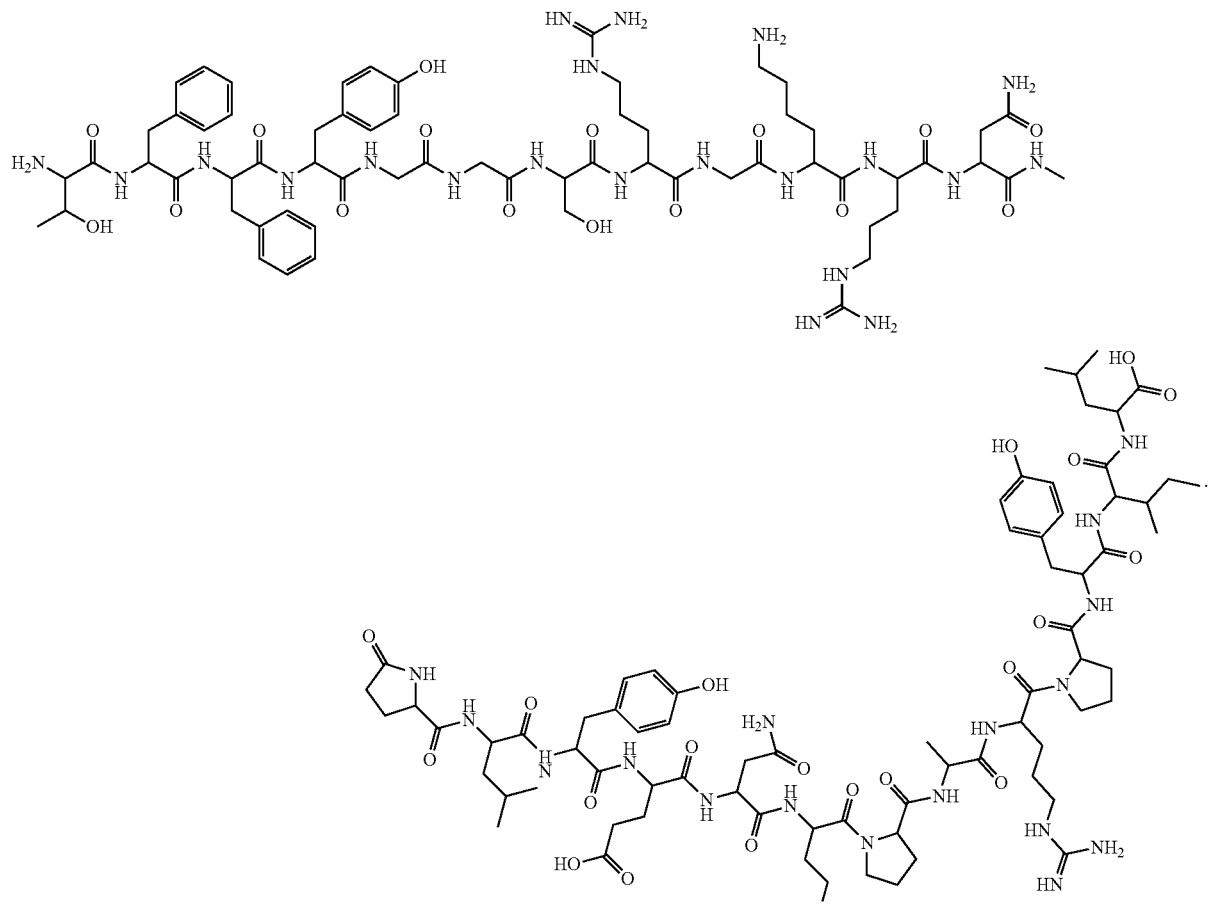

-continued

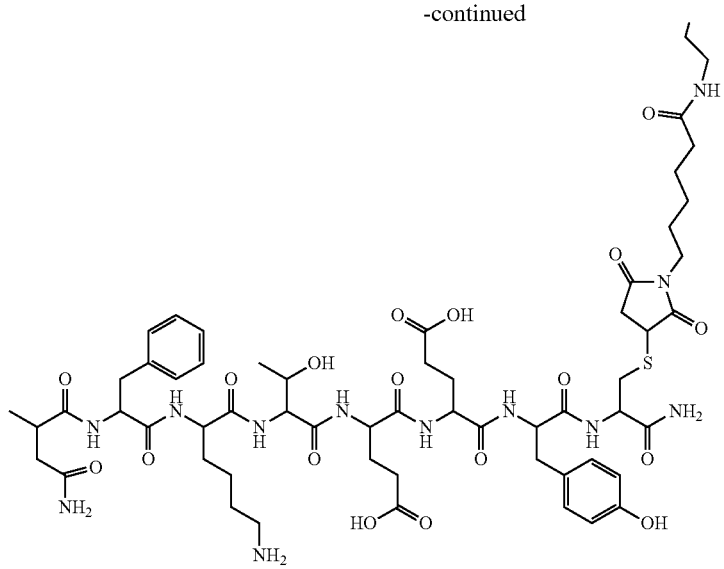

2. A nucleic acid molecule encoding the compound of claim 1.

3. A vector comprising the nucleic acid molecule of claim 2, wherein said nucleic acid is operably linked to a promoter.

4. A method of making a compound, said method comprising expressing a polypeptide encoded by the vector of claim 3 in a cell, and purifying said polypeptide.

5. A method of making a compound of claim 1, said method comprising synthesizing said compound on solid support.

6. A method of reducing body temperature of a subject, said method comprising administering a compound of claim 1 in an amount sufficient to reduce body temperature.

7. The method of claim 6, wherein said subject is suffering from or has suffered from stroke, heart attack, cerebral ischemia, cardiac ischemia, or a nerve injury or is in need of neuroprotection.

8. The method of claim 7, wherein said nerve injury is a brain or spinal cord injury.

9. The method of claim 8, wherein said brain injury is a traumatic head or brain injury.

10. The method of claim 7, wherein said subject is undergoing or is about to undergo a surgical procedure.

11. The method of claim 10, wherein said surgical procedure is cardiac surgery or open heart surgery.

12. The method of claim 6, wherein said subject is suffering from malignant hypothermia.

13. A method of treating pain or prophylactically treating pain in a subject, said method comprising administering a compound of claim 1 in an amount sufficient to treat said pain.

14. The method of claim 13, wherein said pain is an acute pain selected from the group consisting of mechanical pain, heat pain, cold pain, ischemic pain, and chemical-induced pain.

15. The method of claim 13, wherein said pain is peripheral or central neuropathic pain, inflammatory pain, migraine-related pain, headache-related pain, irritable bowel syndrome-related pain, fibromyalgia-related pain, arthritic pain, skeletal pain, joint pain, gastrointestinal pain, muscle pain, angina pain, facial pain, pelvic pain, claudication, postoperative pain, post traumatic pain, tension-type headache, obstetric pain, gynecological pain, or chemotherapy-induced pain.

16. A method of decreasing pain sensitivity in a subject, said method comprising administering an effective amount of a compound of claim 1 to said subject.

17. A method of treating a subject having a psychotic disorder, said method comprising administering a compound of claim 1 in an amount sufficient to treat said disorder, wherein said psychotic disorder is schizophrenia.

18. A method of treating a subject having a metabolic disorder, said method comprising administering a compound of claim 1 in an amount sufficient to treat said disorder.

19. The method of claim 18, wherein said amount sufficient is less than 50% of the amount required for an equivalent dose of the neurotensin agonist when not conjugated to the peptide vector.

20. The method of claim 19, wherein said amount is less than 15%.

21. The method of claim 18, wherein said metabolic disorder is diabetes, obesity, diabetes as a consequence of obesity, hyperglycemia, dyslipidemia, hypertriglyceridemia, syndrome X, insulin resistance, impaired glucose tolerance (IGT), diabetic dyslipidemia, hyperlipidemia, a cardiovascular disease, or hypertension.

22. A method of treating or treating prophylactically a neurological disorder in a subject, said method comprising administering a compound of claim 1 to said subject in an amount sufficient to treat or prevent said disorder, wherein said neurological disorder is schizophrenia, obsessive-compulsive disorder, or Tourette's syndrome.

23. The method of claim 22, wherein the disorder neurological disorder is schizophrenia.

24. The method of claim 22, wherein said neurological disorder is obsessive-compulsive disorder.

25. The method of claim 22, wherein said neurological disorder is Tourette's syndrome.

* * * * *

UNITED STATES PATENT AND TRADEMARK OFFICE
CERTIFICATE OF CORRECTION

PATENT NO. : 9,914,754 B2  
APPLICATION NO. : 12/632557  
DATED : March 13, 2018  
INVENTOR(S) : Castaigne et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1256 days.

Signed and Sealed this  
Seventeenth Day of June, 2025

Coke Morgan Stewart  
*Acting Director of the United States Patent and Trademark Office*

SEQUENCE LISTING

<160> NUMBER OF SEQ ID NOS: 162

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Phe Val Tyr Gly Gly Cys Arg Ala Lys Arg Asn Asn Phe Lys Ser
1               5                   10                  15

Ala Glu Asp

<210> SEQ ID NO 2
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 2

Thr Phe Gln Tyr Gly Gly Cys Met Gly Asn Gly Asn Asn Phe Val Thr
1               5                   10                  15

Glu Lys Glu

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Phe Phe Tyr Gly Gly Cys Gly Gly Asn Arg Asn Asn Phe Asp Thr
1               5                   10                  15

Glu Glu Tyr

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Phe Tyr Tyr Gly Gly Cys Leu Gly Asn Lys Asn Asn Tyr Leu Arg
1               5                   10                  15

Glu Glu Glu

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Phe Phe Tyr Gly Gly Cys Arg Ala Lys Arg Asn Asn Phe Lys Arg
1               5                   10                  15

Ala Lys Tyr

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Phe Phe Tyr Gly Gly Cys Arg Gly Lys Arg Asn Asn Phe Lys Arg
1               5                   10                  15

Ala Lys Tyr

<210> SEQ ID NO 7
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 7

Thr Phe Phe Tyr Gly Gly Cys Arg Ala Lys Lys Asn Asn Tyr Lys Arg
1               5                   10                  15

Ala Lys Tyr

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr Phe Phe Tyr Gly Gly Cys Arg Gly Lys Lys Asn Asn Phe Lys Arg
1               5                   10                  15

Ala Lys Tyr

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Phe Gln Tyr Gly Gly Cys Arg Ala Lys Arg Asn Asn Phe Lys Arg
1               5                   10                  15

Ala Lys Tyr

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Phe Gln Tyr Gly Gly Cys Arg Gly Lys Lys Asn Asn Phe Lys Arg
1               5                   10                  15

Ala Lys Tyr

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Phe Phe Tyr Gly Gly Cys Leu Gly Lys Arg Asn Asn Phe Lys Arg
1               5                   10                  15

Ala Lys Tyr

<210> SEQ ID NO 12
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Phe Phe Tyr Gly Gly Ser Leu Gly Lys Arg Asn Asn Phe Lys Arg
1               5                   10                  15

Ala Lys Tyr

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Phe Phe Tyr Gly Gly Cys Gly Gly Lys Lys Asn Asn Phe Lys Arg
1               5                   10                  15

Ala Lys Tyr

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Phe Phe Tyr Gly Gly Cys Arg Gly Lys Gly Asn Asn Tyr Lys Arg
1               5                   10                  15

Ala Lys Tyr

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Phe Phe Tyr Gly Gly Cys Arg Gly Lys Arg Asn Asn Phe Leu Arg
1               5                   10                  15

Ala Lys Tyr

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Phe Phe Tyr Gly Gly Cys Arg Gly Lys Arg Asn Asn Phe Lys Arg
1               5                   10                  15

Glu Lys Tyr

<210> SEQ ID NO 17
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Phe Phe Tyr Gly Gly Cys Arg Ala Lys Lys Asn Asn Phe Lys Arg
1               5                   10                  15

Ala Lys Glu

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Phe Phe Tyr Gly Gly Cys Arg Gly Lys Arg Asn Asn Phe Lys Arg
1               5                   10                  15

Ala Lys Asp

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Phe Phe Tyr Gly Gly Cys Arg Ala Lys Arg Asn Asn Phe Asp Arg
1               5                   10                  15

Ala Lys Tyr

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Phe Phe Tyr Gly Gly Cys Arg Gly Lys Lys Asn Asn Phe Lys Arg
1               5                   10                  15

Ala Glu Tyr

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Phe Phe Tyr Gly Gly Cys Gly Ala Asn Arg Asn Asn Phe Lys Arg
1               5                   10                  15

Ala Lys Tyr
```

```
<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Phe Phe Tyr Gly Gly Cys Gly Gly Lys Lys Asn Asn Phe Lys Thr
1               5                   10                  15

Ala Lys Tyr

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Phe Phe Tyr Gly Gly Cys Arg Gly Asn Arg Asn Asn Phe Leu Arg
1               5                   10                  15

Ala Lys Tyr

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Phe Phe Tyr Gly Gly Cys Arg Gly Asn Arg Asn Asn Phe Lys Thr
1               5                   10                  15

Ala Lys Tyr

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Phe Phe Tyr Gly Gly Ser Arg Gly Asn Arg Asn Asn Phe Lys Thr
1               5                   10                  15

Ala Lys Tyr

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Phe Phe Tyr Gly Gly Cys Leu Gly Asn Gly Asn Asn Phe Lys Arg
1               5                   10                  15

Ala Lys Tyr
```

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Phe Phe Tyr Gly Gly Cys Leu Gly Asn Arg Asn Asn Phe Leu Arg
1               5                   10                  15

Ala Lys Tyr

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Phe Phe Tyr Gly Gly Cys Leu Gly Asn Arg Asn Asn Phe Lys Thr
1               5                   10                  15

Ala Lys Tyr

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Phe Phe Tyr Gly Gly Cys Arg Gly Asn Gly Asn Asn Phe Lys Ser
1               5                   10                  15

Ala Lys Tyr

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Phe Phe Tyr Gly Gly Cys Arg Gly Lys Lys Asn Asn Phe Asp Arg
1               5                   10                  15

Glu Lys Tyr

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Phe Phe Tyr Gly Gly Cys Arg Gly Lys Arg Asn Asn Phe Leu Arg
1               5                   10                  15

Glu Lys Glu

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Phe Phe Tyr Gly Gly Cys Arg Gly Lys Gly Asn Asn Phe Asp Arg
1               5                   10                  15

Ala Lys Tyr

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Thr Phe Phe Tyr Gly Gly Ser Arg Gly Lys Gly Asn Asn Phe Asp Arg
1               5                   10                  15

Ala Lys Tyr

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Phe Phe Tyr Gly Gly Cys Arg Gly Asn Gly Asn Asn Phe Val Thr
1               5                   10                  15

Ala Lys Tyr

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Phe Phe Tyr Gly Gly Cys Gly Gly Lys Gly Asn Asn Tyr Val Thr
1               5                   10                  15

Ala Lys Tyr

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Thr Phe Phe Tyr Gly Gly Cys Leu Gly Lys Gly Asn Asn Phe Leu Thr
1               5                   10                  15

Ala Lys Tyr

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Phe Phe Tyr Gly Gly Cys Leu Gly Asn Lys Asn Asn Phe Leu Thr
1               5                   10                  15

Ala Lys Tyr

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Phe Phe Tyr Gly Gly Cys Gly Gly Asn Lys Asn Asn Phe Val Arg
1               5                   10                  15

Glu Lys Tyr

<210> SEQ ID NO 39
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Phe Phe Tyr Gly Gly Cys Met Gly Asn Lys Asn Asn Phe Val Arg
1               5                   10                  15

Glu Lys Tyr

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Phe Phe Tyr Gly Gly Ser Met Gly Asn Lys Asn Asn Phe Val Arg
1               5                   10                  15

Glu Lys Tyr

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Phe Phe Tyr Gly Gly Cys Leu Gly Asn Arg Asn Asn Tyr Val Arg
1               5                   10                  15

Glu Lys Tyr

<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Phe Phe Tyr Gly Gly Cys Leu Gly Asn Arg Asn Asn Phe Val Arg
1               5                   10                  15

Glu Lys Tyr

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Thr Phe Phe Tyr Gly Gly Cys Leu Gly Asn Lys Asn Asn Tyr Val Arg
1               5                   10                  15

Glu Lys Tyr

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Thr Phe Phe Tyr Gly Gly Cys Gly Gly Asn Gly Asn Asn Phe Leu Thr
1               5                   10                  15

Ala Lys Tyr

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Thr Phe Phe Tyr Gly Gly Cys Arg Gly Asn Arg Asn Asn Phe Leu Thr
1               5                   10                  15

Ala Glu Tyr

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Phe Phe Tyr Gly Gly Cys Arg Gly Asn Gly Asn Asn Phe Lys Ser

```
1               5                   10                  15

Ala Glu Tyr

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Phe Phe Tyr Gly Gly Cys Leu Gly Asn Lys Asn Asn Phe Lys Thr
1               5                   10                  15

Ala Glu Tyr

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Phe Phe Tyr Gly Gly Cys Arg Gly Asn Arg Asn Asn Phe Lys Thr
1               5                   10                  15

Glu Glu Tyr

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Phe Phe Tyr Gly Gly Cys Arg Gly Lys Arg Asn Asn Phe Lys Thr
1               5                   10                  15

Glu Glu Asp

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Phe Phe Tyr Gly Gly Cys Gly Gly Asn Gly Asn Asn Phe Val Arg
1               5                   10                  15

Glu Lys Tyr

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51
```

Ser Phe Phe Tyr Gly Gly Cys Met Gly Asn Gly Asn Asn Phe Val Arg
1               5                   10                  15

Glu Lys Tyr

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Phe Phe Tyr Gly Gly Cys Gly Gly Asn Gly Asn Asn Phe Leu Arg
1               5                   10                  15

Glu Lys Tyr

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Phe Phe Tyr Gly Gly Cys Leu Gly Asn Gly Asn Asn Phe Val Arg
1               5                   10                  15

Glu Lys Tyr

<210> SEQ ID NO 54
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Phe Phe Tyr Gly Gly Cys Leu Gly Asn Gly Asn Asn Tyr Leu Arg
1               5                   10                  15

Glu Lys Tyr

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Phe Phe Tyr Gly Gly Ser Leu Gly Asn Gly Asn Asn Phe Val Arg
1               5                   10                  15

Glu Lys Tyr

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Phe Phe Tyr Gly Gly Cys Arg Gly Asn Gly Asn Asn Phe Val Thr
1               5                   10                  15

Ala Glu Tyr

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Phe Phe Tyr Gly Gly Cys Leu Gly Lys Gly Asn Asn Phe Val Ser
1               5                   10                  15

Ala Glu Tyr

<210> SEQ ID NO 58
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Thr Phe Phe Tyr Gly Gly Cys Leu Gly Asn Arg Asn Asn Phe Asp Arg
1               5                   10                  15

Ala Glu Tyr

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Phe Phe Tyr Gly Gly Cys Leu Gly Asn Arg Asn Asn Phe Leu Arg
1               5                   10                  15

Glu Glu Tyr

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Phe Phe Tyr Gly Gly Cys Leu Gly Asn Lys Asn Asn Tyr Leu Arg
1               5                   10                  15

Glu Glu Tyr

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 61

Pro Phe Phe Tyr Gly Gly Cys Gly Gly Asn Arg Asn Asn Tyr Leu Arg
1               5                   10                  15

Glu Glu Tyr

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Phe Phe Tyr Gly Gly Ser Gly Gly Asn Arg Asn Asn Tyr Leu Arg
1               5                   10                  15

Glu Glu Tyr

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Arg Pro Asp Phe Cys Leu Glu Pro Pro Tyr Thr Gly Pro Cys Val
1               5                   10                  15

Ala Arg Ile

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Arg Ile Ile Arg Tyr Phe Tyr Asn Ala Lys Ala Gly Leu Cys Gln
1               5                   10                  15

Thr Phe Val Tyr Gly
            20

<210> SEQ ID NO 65
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Tyr Gly Gly Cys Arg Ala Lys Arg Asn Asn Tyr Lys Ser Ala Glu Asp
1               5                   10                  15

Cys Met Arg Thr Cys Gly
            20

<210> SEQ ID NO 66
<211> LENGTH: 22
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 66

Pro Asp Phe Cys Leu Glu Pro Pro Tyr Thr Gly Pro Cys Val Ala Arg
1               5                   10                  15

Ile Ile Arg Tyr Phe Tyr
            20

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Thr Phe Phe Tyr Gly Gly Cys Arg Gly Lys Arg Asn Asn Phe Lys Thr
1               5                   10                  15

Glu Glu Tyr

<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Phe Phe Tyr Gly Gly Cys Arg Gly Lys Arg Asn Asn Phe Lys Thr
1               5                   10                  15

Glu Glu Tyr

<210> SEQ ID NO 69
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Thr Phe Tyr Tyr Gly Gly Cys Arg Gly Lys Arg Asn Asn Tyr Lys Thr
1               5                   10                  15

Glu Glu Tyr

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Phe Phe Tyr Gly Gly Ser Arg Gly Lys Arg Asn Asn Phe Lys Thr
1               5                   10                  15

Glu Glu Tyr

<210> SEQ ID NO 71
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 71

Cys Thr Phe Phe Tyr Gly Cys Cys Arg Gly Lys Arg Asn Asn Phe Lys
1               5                   10                  15

Thr Glu Glu Tyr
            20

<210> SEQ ID NO 72
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Phe Phe Tyr Gly Gly Cys Arg Gly Lys Arg Asn Asn Phe Lys Thr
1               5                   10                  15

Glu Glu Tyr Cys
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Thr Phe Phe Tyr Gly Ser Cys Arg Gly Lys Arg Asn Asn Phe Lys
1               5                   10                  15

Thr Glu Glu Tyr
            20

<210> SEQ ID NO 74
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 75
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Phe Phe Tyr Gly Gly Cys Arg Gly Lys Arg Asn Asn Phe Lys Thr
1               5                   10                  15

Glu Glu Tyr
```

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Phe Phe Tyr Gly Gly Cys Arg Gly Lys Arg Asn Asn Phe Lys Thr
1               5                   10                  15

Lys Glu Tyr

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Phe Phe Tyr Gly Gly Lys Arg Gly Lys Arg Asn Asn Phe Lys Thr
1               5                   10                  15

Glu Glu Tyr

<210> SEQ ID NO 78
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Thr Phe Phe Tyr Gly Gly Cys Arg Gly Lys Arg Asn Asn Phe Lys Thr
1               5                   10                  15

Lys Arg Tyr

<210> SEQ ID NO 79
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Thr Phe Phe Tyr Gly Gly Lys Arg Gly Lys Arg Asn Asn Phe Lys Thr
1               5                   10                  15

Ala Glu Tyr

<210> SEQ ID NO 80
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Phe Phe Tyr Gly Gly Lys Arg Gly Lys Arg Asn Asn Phe Lys Thr
1               5                   10                  15

Ala Gly Tyr

<210> SEQ ID NO 81
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Phe Phe Tyr Gly Gly Lys Arg Gly Lys Arg Asn Asn Phe Lys Arg
1               5                   10                  15

Glu Lys Tyr

<210> SEQ ID NO 82
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Phe Phe Tyr Gly Gly Lys Arg Gly Lys Arg Asn Asn Phe Lys Arg
1               5                   10                  15

Ala Lys Tyr

<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Phe Phe Tyr Gly Gly Cys Leu Gly Asn Arg Asn Asn Phe Lys Thr
1               5                   10                  15

Glu Glu Tyr

<210> SEQ ID NO 84
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Phe Phe Tyr Gly Cys Gly Arg Gly Lys Arg Asn Asn Phe Lys Thr
1               5                   10                  15

Glu Glu Tyr

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Phe Phe Tyr Gly Gly Arg Cys Gly Lys Arg Asn Asn Phe Lys Thr
1               5                   10                  15

Glu Glu Tyr

```
<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86
```

Thr Phe Phe Tyr Gly Gly Cys Leu Gly Asn Gly Asn Asn Phe Asp Thr
1               5                   10                  15

Glu Glu Glu

```
<210> SEQ ID NO 87
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87
```

Thr Phe Gln Tyr Gly Gly Cys Arg Gly Lys Arg Asn Asn Phe Lys Thr
1               5                   10                  15

Glu Glu Tyr

```
<210> SEQ ID NO 88
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88
```

Tyr Asn Lys Glu Phe Gly Thr Phe Asn Thr Lys Gly Cys Glu Arg Gly
1               5                   10                  15

Tyr Arg Phe

```
<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89
```

Arg Phe Lys Tyr Gly Gly Cys Leu Gly Asn Met Asn Asn Phe Glu Thr
1               5                   10                  15

Leu Glu Glu

```
<210> SEQ ID NO 90
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90
```

Arg Phe Lys Tyr Gly Gly Cys Leu Gly Asn Lys Asn Asn Phe Leu Arg

```
1               5                   10                  15
Leu Lys Tyr

<210> SEQ ID NO 91
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Phe Lys Tyr Gly Gly Cys Leu Gly Asn Lys Asn Asn Tyr Leu Arg
1               5                   10                  15

Leu Lys Tyr

<210> SEQ ID NO 92
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Thr Lys Arg Lys Arg Lys Lys Gln Arg Val Lys Ile Ala Tyr Glu
1               5                   10                  15

Glu Ile Phe Lys Asn Tyr
            20

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Thr Lys Arg Lys Arg Lys Lys Gln Arg Val Lys Ile Ala Tyr
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Gly Gly Arg Leu Ser Tyr Ser Arg Arg Phe Ser Thr Ser Thr Gly
1               5                   10                  15

Arg

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Arg Leu Ser Tyr Ser Arg Arg Arg Phe
```

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Gln Ile Lys Ile Trp Phe Gln Asn Arg Arg Met Lys Trp Lys Lys
1               5                   10                  15

<210> SEQ ID NO 97
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Thr Phe Phe Tyr Gly Gly Ser Arg Gly Lys Arg Asn Asn Phe Lys Thr
1               5                   10                  15

Glu Glu Tyr

<210> SEQ ID NO 98
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Arg Pro Asp Phe Cys Leu Glu Pro Pro Tyr Thr Gly Pro Cys Val
1               5                   10                  15

Ala Arg Ile Ile Arg Tyr Phe Tyr Asn Ala Lys Ala Gly Leu Cys Gln
                20                  25                  30

Thr Phe Val Tyr Gly Gly Cys Arg Ala Lys Arg Asn Asn Phe Lys Ser
            35                  40                  45

Ala Glu Asp Cys Met Arg Thr Cys Gly Gly Ala
        50                  55

<210> SEQ ID NO 99
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Phe Phe Tyr Gly Gly Cys Arg Gly Lys Arg Asn Asn Phe Lys Thr
1               5                   10                  15

Lys Glu Tyr

<210> SEQ ID NO 100
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Phe Lys Tyr Gly Gly Cys Leu Gly Asn Lys Asn Asn Tyr Leu Arg
1               5                   10                  15

Leu Lys Tyr

<210> SEQ ID NO 101
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Thr Phe Phe Tyr Gly Gly Cys Arg Ala Lys Arg Asn Asn Phe Lys Arg
1               5                   10                  15

Ala Lys Tyr

<210> SEQ ID NO 102
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asn Ala Lys Ala Gly Leu Cys Gln Thr Phe Val Tyr Gly Gly Cys Leu
1               5                   10                  15

Ala Lys Arg Asn Asn Phe Glu Ser Ala Glu Asp Cys Met Arg Thr Cys
                20                  25                  30

Gly Gly Ala
        35

<210> SEQ ID NO 103
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Gly Gly Cys Arg Ala Lys Arg Asn Asn Phe Lys Ser Ala Glu Asp
1               5                   10                  15

Cys Met Arg Thr Cys Gly Gly Ala
                20

<210> SEQ ID NO 104
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Leu Cys Gln Thr Phe Val Tyr Gly Gly Cys Arg Ala Lys Arg Asn
1               5                   10                  15

Asn Phe Lys Ser Ala Glu
                20

```
<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Leu Cys Gln Thr Phe Val Tyr Gly Gly Cys Glu Ala Lys Arg Asn Asn
1               5                   10                  15

Phe Lys Ser Ala
            20

<210> SEQ ID NO 106

<400> SEQUENCE: 106

000

<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Phe Phe Tyr Gly Gly Ser Arg Gly Lys Arg Asn Asn Phe Lys Thr
1               5                   10                  15

Glu Glu Tyr

<210> SEQ ID NO 108
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Phe Phe Tyr Gly Gly Ser Arg Gly Lys Arg Asn Asn Phe Lys Thr
1               5                   10                  15

Glu Glu Tyr

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Phe Phe Tyr Gly Gly Ser Arg Gly Lys Arg Asn Asn Phe Lys Thr
1               5                   10                  15

Glu Glu Tyr

<210> SEQ ID NO 110
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 110

Arg Phe Phe Tyr Gly Gly Ser Arg Gly Lys Arg Asn Asn Phe Arg Thr
1               5                   10                  15

Glu Glu Tyr

<210> SEQ ID NO 111
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Phe Phe Tyr Gly Gly Ser Arg Gly Lys Arg Asn Asn Phe Arg Thr
1               5                   10                  15

Glu Glu Tyr

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Thr Phe Phe Tyr Gly Gly Ser Arg Gly Arg Arg Asn Asn Phe Arg Thr
1               5                   10                  15

Glu Glu Tyr

<210> SEQ ID NO 113
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Thr Phe Phe Tyr Gly Gly Ser Arg Gly Lys Arg Asn Asn Phe Lys
1               5                   10                  15

Thr Glu Glu Tyr
            20

<210> SEQ ID NO 114
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 115
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 115

Cys Thr Phe Phe Tyr Gly Gly Ser Arg Gly Arg Arg Asn Asn Phe Arg
1               5                   10                  15

Thr Glu Glu Tyr
            20

<210> SEQ ID NO 116
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Thr Phe Phe Tyr Gly Gly Ser Arg Gly Arg Arg Asn Asn Phe Arg Thr
1               5                   10                  15

Glu Glu Tyr Cys
            20

<210> SEQ ID NO 117
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamic acid

<400> SEQUENCE: 117

Xaa Leu Tyr Glu Asn Lys Pro Arg Arg Pro Tyr Ile Leu
1               5                   10

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: Cyclic

<400> SEQUENCE: 118

Arg Lys Pro Trp Glu Leu
1               5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Arg Gly Tyr Ile Leu
1               5
```

```
<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Arg Pro Ala Ile Leu
1               5

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Arg Pro Tyr Leu Leu
1               5

<210> SEQ ID NO 122
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Arg Arg Pro Tyr Val Leu
1               5

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Lys Arg Pro Tyr Ile Leu
1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Lys Pro Tyr Ile Leu
1               5

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 125

Lys Lys Pro Tyr Ile Leu
1               5

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ornithine

<400> SEQUENCE: 126

Xaa Arg Pro Tyr Ile Leu
1               5

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ornithine

<400> SEQUENCE: 127

Arg Xaa Pro Tyr Ile Leu
1               5

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Ornithine

<400> SEQUENCE: 128

Xaa Xaa Pro Tyr Ile Leu
1               5

<210> SEQ ID NO 129
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Diaminobutyric acid

<400> SEQUENCE: 129

Xaa Arg Pro Tyr Ile Leu
1               5

<210> SEQ ID NO 130
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Diaminobutyric acid

<400> SEQUENCE: 130

Arg Xaa Pro Tyr Ile Leu
1               5

<210> SEQ ID NO 131
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Diaminobutyric acid

<400> SEQUENCE: 131

Xaa Xaa Pro Tyr Ile Leu
1               5

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Cyclohexylalanine

<400> SEQUENCE: 132

Arg Arg Pro Xaa Ile Leu
1               5

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 3,2-naphthyl-alanine

<400> SEQUENCE: 133

Arg Arg Pro Xaa Ile Leu
1               5

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Ornithine

<400> SEQUENCE: 134

Xaa Pro Tyr Ile Leu
1               5

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Diaminoproprionic acid

<400> SEQUENCE: 135

Xaa Arg Pro Tyr Ile Leu
1               5

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Diaminoproprionic acid

<400> SEQUENCE: 136

Arg Xaa Pro Tyr Ile Leu
1               5

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Diaminoproprionic acid

<400> SEQUENCE: 137

Xaa Xaa Pro Tyr Ile Leu
1               5

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Homoarginine

<400> SEQUENCE: 138

Arg Xaa Pro Tyr Ile Leu
```

```
1               5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Homoarginine

<400> SEQUENCE: 139

Xaa Xaa Pro Tyr Ile Leu
1               5

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Homoarginine

<400> SEQUENCE: 140

Xaa Arg Pro Tyr Ile Leu
1               5

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 1,2,3,4-tetrahydroisoquinoline-3-carboxylic
      acid

<400> SEQUENCE: 141

Arg Arg Pro Xaa Ile Leu
1               5

<210> SEQ ID NO 142
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 3,1-naphthyl-alanine

<400> SEQUENCE: 142

Arg Arg Pro Xaa Ile Leu
1               5

<210> SEQ ID NO 143
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 1-pipecolinic acid

<400> SEQUENCE: 143

Arg Arg Xaa Tyr Ile Leu
1               5

<210> SEQ ID NO 144
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (8)..(8)
<223> OTHER INFORMATION: Benzoylphenylalanine

<400> SEQUENCE: 144

Xaa Leu Tyr Glu Asn Lys Pro Xaa Arg Pro Tyr Ile Leu
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (5)..(5)
<223> OTHER INFORMATION: Benzoylphenylalanine

<400> SEQUENCE: 145

Xaa Leu Tyr Glu Xaa Lys Pro Arg Arg Pro Tyr Ile Leu
1               5                   10

<210> SEQ ID NO 146
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (9)..(9)
<223> OTHER INFORMATION: Benzoylphenylalanine

<400> SEQUENCE: 146

Xaa Leu Tyr Glu Asn Lys Pro Arg Xaa Pro Tyr Ile Leu
1               5                   10
```

```
<210> SEQ ID NO 147
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Diaminobutyric acid
<220> FEATURE:
<221> NAME/KEY: MOD_RES
<222> LOCATION: (4)..(4)
<223> OTHER INFORMATION: 3,1-naphthyl-alanine

<400> SEQUENCE: 147

Arg Xaa Pro Xaa Ile Leu
1               5

<210> SEQ ID NO 148
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (9)..(9)
<223> OTHER INFORMATION: Ornithine

<400> SEQUENCE: 148

Xaa Leu Tyr Glu Asn Lys Pro Arg Xaa Pro Tyr Ile Leu
1               5                   10

<210> SEQ ID NO 149
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (11)..(11)
<223> OTHER INFORMATION: 3,1-naphthyl-alanine

<400> SEQUENCE: 149

Xaa Leu Tyr Glu Asn Lys Pro Arg Arg Pro Xaa Ile Leu
1               5                   10

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Neo-Trp
```

<400> SEQUENCE: 150

Arg Arg Pro Xaa Ile Leu
1               5

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Neo-Trp
<220> FEATURE:
<221> NAME/KEY: MOD_RES
<222> LOCATION: (5)..(5)
<223> OTHER INFORMATION: Tert-Leu

<400> SEQUENCE: 151

Arg Arg Pro Xaa Xaa Leu
1               5

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-Arg
<220> FEATURE:
<221> NAME/KEY: MOD_RES
<222> LOCATION: (4)..(4)
<223> OTHER INFORMATION: Neo-Trp
<220> FEATURE:
<221> NAME/KEY: MOD_RES
<222> LOCATION: (5)..(5)
<223> OTHER INFORMATION: Tert-Leu

<400> SEQUENCE: 152

Xaa Lys Pro Xaa Xaa Leu
1               5

<210> SEQ ID NO 153
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamic acid
<220> FEATURE:
<221> NAME/KEY: MOD_RES
<222> LOCATION: (3)..(3)
<223> OTHER INFORMATION: Iodo-Tyr

<400> SEQUENCE: 153

Xaa Leu Xaa Glu Asn Lys Pro Arg Arg Pro Tyr Ile Leu
1               5                   10

<210> SEQ ID NO 154
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-methyl-Arg
<220> FEATURE:
<221> NAME/KEY: MOD_RES
<222> LOCATION: (2)..(2)
<223> OTHER INFORMATION: Diaminobutyric acid
<220> FEATURE:
<221> NAME/KEY: MOD_RES
<222> LOCATION: (4)..(4)
<223> OTHER INFORMATION: Neo-Trp
<220> FEATURE:
<221> NAME/KEY: MOD_RES
<222> LOCATION: (5)..(5)
<223> OTHER INFORMATION: Tert-Leu

<400> SEQUENCE: 154

Xaa Xaa Pro Xaa Xaa Leu
1               5

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Diaminobutyric acid
<220> FEATURE:
<221> NAME/KEY: MOD_RES
<222> LOCATION: (4)..(4)
<223> OTHER INFORMATION: Neo-Trp

<400> SEQUENCE: 155

Xaa Arg Pro Xaa Ile Leu
1               5

<210> SEQ ID NO 156
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
atgagaccag atttctgcct cgagccgccg tacactgggc cctgcaaagc tcgtatcatc        60
cgttacttct acaatgcaaa ggcaggcctg tgtcagacct tcgtatacgg cggctgcaga       120
gctaagcgta caacttcaa atccgcggaa gactgcatgc gtacttgcgg tggtgcttag        180

<210> SEQ ID NO 157
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: This sequence may encompass 1-6 'Gly-Gly-Gly-
      Gly-Ser' repeating units

<400> SEQUENCE: 157
```

```
Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20              25              30
```

<210> SEQ ID NO 158
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: This sequence may encompass 1-5 'Xaa-Xaa-Xaa-
      Xaa-Gly' repeating units
<220> FEATURE:
<221> NAME/KEY: MOD_RES
<222> LOCATION: (1)..(4)
<223> OTHER INFORMATION: Thr or Ser
<220> FEATURE:
<221> NAME/KEY: MOD_RES
<222> LOCATION: (6)..(9)
<223> OTHER INFORMATION: Thr or Ser
<220> FEATURE:
<221> NAME/KEY: MOD_RES
<222> LOCATION: (11)..(14)
<223> OTHER INFORMATION: Thr or Ser
<220> FEATURE:
<221> NAME/KEY: MOD_RES
<222> LOCATION: (16)..(19)
<223> OTHER INFORMATION: Thr or Ser
<220> FEATURE:
<221> NAME/KEY: MOD_RES
<222> LOCATION: (21)..(24)
<223> OTHER INFORMATION: Thr or Ser
<220> FEATURE:
<223> OTHER INFORMATION: See specification as filed for detailed
      description of substitutions and preferred embodiments

<400> SEQUENCE: 158

```
Xaa Xaa Xaa Xaa Gly Xaa Xaa Xaa Xaa Gly Xaa Xaa Xaa Xaa Gly Xaa
1               5                   10                  15

Xaa Xaa Xaa Gly Xaa Xaa Xaa Xaa Gly
            20                  25
```

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

```
Ser Ser Ser Ser Gly
1               5
```

<210> SEQ ID NO 160
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

```
Arg Arg Pro Tyr Ile Leu
1               5
```

```
<210> SEQ ID NO 161
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 161

Thr Phe Phe Tyr Gly Gly Ser Arg Gly Lys Arg Asn Asn Phe Lys Thr
1               5                   10                  15

Glu Glu Tyr Cys
            20

<210> SEQ ID NO 162
<211> LENGTH: 13
<212> TYPE: PRT
<213> ORGANISM: Homo sapiens

<400> SEQUENCE: 162

Gln Leu Tyr Glu Asn Lys Pro Arg Arg Pro Tyr Ile Leu
1               5                   10
```